(12) United States Patent
Teitell et al.

(10) Patent No.: US 9,238,041 B2
(45) Date of Patent: Jan. 19, 2016

(54) METHODS AND COMPOSITIONS FOR REGULATING RNA IMPORT INTO MITOCHONDRIA

(75) Inventors: Michael A. Teitell, Tarzana, CA (US); Carla M. Koehler, Los Angeles, CA (US); Geng Wang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 596 days.

(21) Appl. No.: 13/413,842

(22) Filed: Mar. 7, 2012

(65) Prior Publication Data

US 2012/0283317 A1 Nov. 8, 2012

Related U.S. Application Data

(60) Provisional application No. 61/481,890, filed on May 3, 2011, provisional application No. 61/577,300, filed on Dec. 19, 2011.

(51) Int. Cl.
| | |
|---|---|
| *C12N 15/113* | (2010.01) |
| *A61K 31/7088* | (2006.01) |
| *C12N 15/87* | (2006.01) |
| *C12N 15/11* | (2006.01) |

(52) U.S. Cl.
CPC ............ *A61K 31/7088* (2013.01); *C12N 15/11* (2013.01); *C12N 15/1137* (2013.01); *C12N 15/87* (2013.01); *C12Y 207/07008* (2013.01); *C12N 2310/14* (2013.01)

(58) Field of Classification Search
None
See application file for complete search history.

(56) References Cited

U.S. PATENT DOCUMENTS

| 2003/0073623 A1* | 4/2003 | Drmanac et al. ................ 514/12 |
| 2012/0110693 A1* | 5/2012 | Drouard et al. ............... 800/278 |

FOREIGN PATENT DOCUMENTS

FR 2944806 A1 * 10/2010

OTHER PUBLICATIONS

Kohler et al., Molecular Cell Biology, 2007, vol. 8, pp. 761-773.*
Wang et al., Cell, 2010, vol. 142, pp. 1-20.*
Kuwabara et al., Nucleic Acids Research, 2001, vol. 29, pp. 2780-2788.*
"Leading Edge: In This Issue", Aug. 6, 2010, pp. 336-337, vol. 142, Publisher: Cell.
Chen, et al., "Mammalian Polynucleotide Phosphorylase Is an Intermembrane Space RNase That Maintains Mitochondrial Homeostasis", Sep. 11, 2006, pp. 8475-8487, vol. 26, No. 22, Publisher: Molecular and Cellular Biology.
Chen, et al., "Human polynucleotide phosphorylase: location matters", Nov. 5, 2007, pp. 600-608, vol. 17, No. 12, Publisher: TRENDS in Cell Biology.
Endo, et al., "Mitochondrial Matrix Reloaded with RNA", Aug. 6, 2010, pp. 362-363, vol. 142, Publisher: Cell.
French, et al., "The TCL1 oncoprotein binds the RNase PH domains of the PNPase exoribonuclease without affecting its RNA degrading activity", Jul. 13, 2006, pp. 198-210, vol. 248, Publisher: Cancer Letters.
Rainey, et al., "A New Function in Translocation for the Mitochondrial i-AAA Protease Yme1: Import of Polynucleotide Phosphorylase into the Intermembrane Space", Sep. 11, 2006, pp. 8488-8497, vol. 26, No. 22, Publisher: Molecular and Cellular Biology.

* cited by examiner

*Primary Examiner* — Michele K. Joike
*Assistant Examiner* — Mindy G Brown
(74) *Attorney, Agent, or Firm* — Suzannah K. Sundby, Esq.; Canady + Lortz LLP

(57) ABSTRACT

Disclosed herein are methods of manipulating the processing, targeting, and/or internalization of a nucleic acid molecule. Also disclosed are recombinant and/or isolated nucleic acid molecules having a first nucleic acid sequence, which is a wild-type sequence or an altered sequence, directly or indirectly linked to a second nucleic acid sequence which is a mitochondria localization sequence, an RNA import sequence, or a combination thereof, and methods of using thereof.

11 Claims, 28 Drawing Sheets

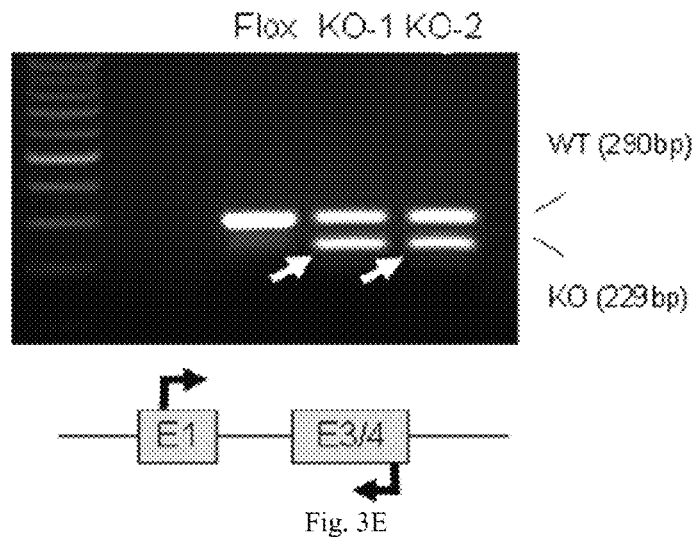
Fig. 3E
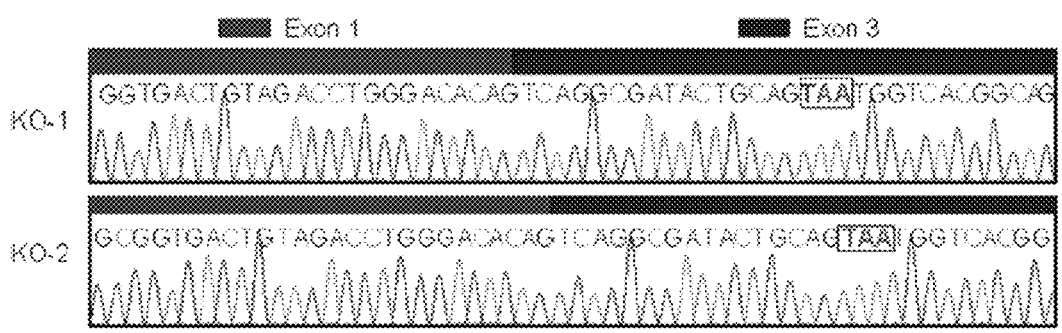
Fig. 3F
$CMV\text{-}CRE \times Pnpt1^{WT/neo\text{-}flox} \rightarrow Pnpt1^{WT/KO}$
$Pnpt1^{WT/KO} \times Pnpt1^{WT/KO}$
| PNPASE Genotype | Observed | Expected |
|---|---|---|
| WT/WT | 24 (36%) | 16.5 (25%) |
| WT/KO | 42 (64%) | 33 (50%) |
| KO/KO | 0 (0%) | 16.5 (25%) |
| total mice: | 66 | 66 |
| chi-square: p<0.00001 | | |
Fig. 4A

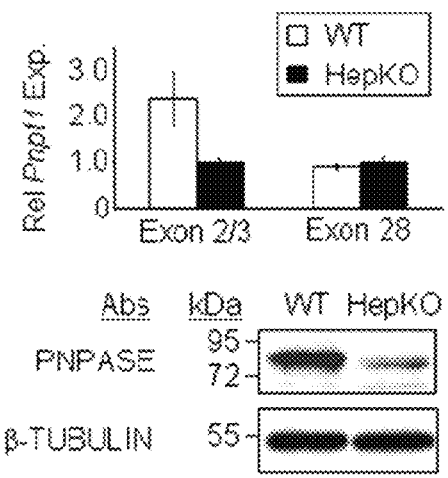
Fig. 4B
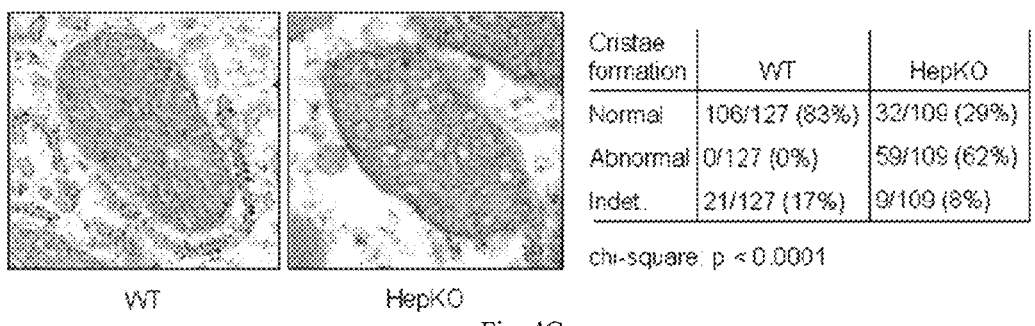
Fig. 4C
Fig. 4D

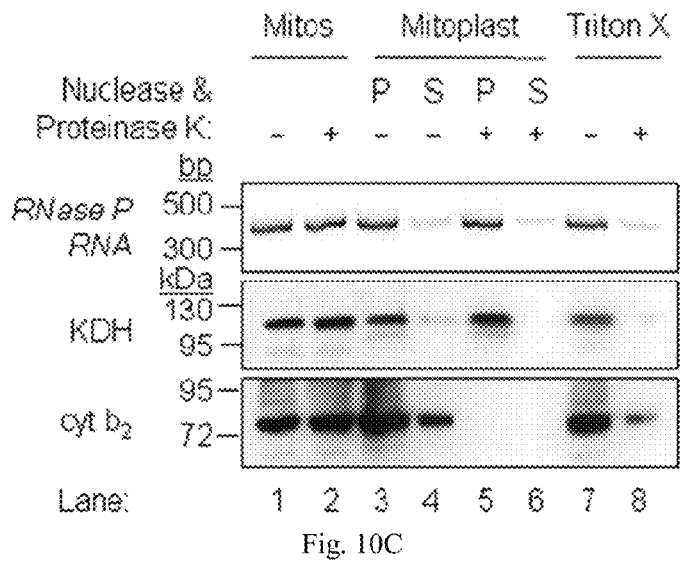
Fig. 10C
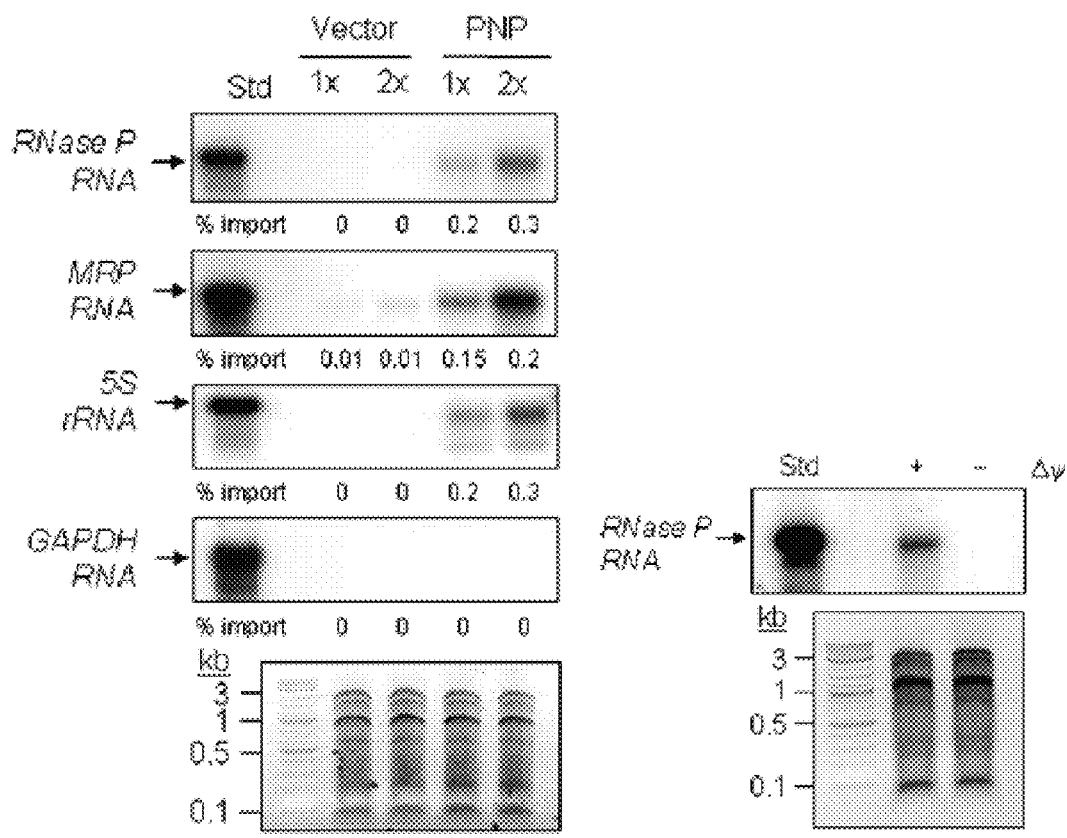
Fig. 10D
Fig. 10E

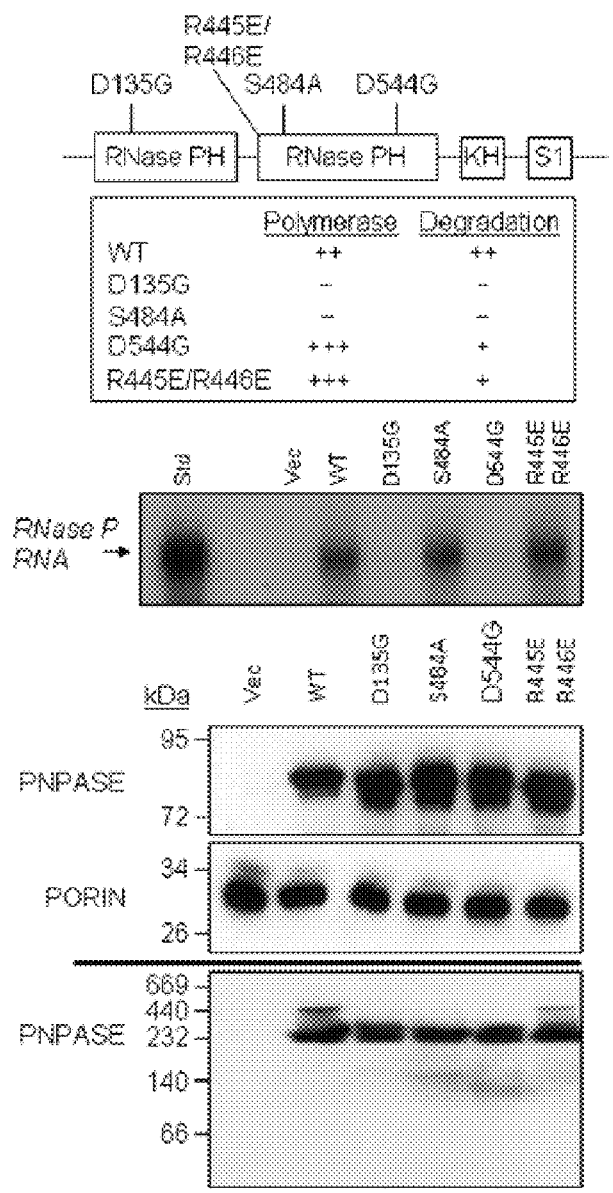
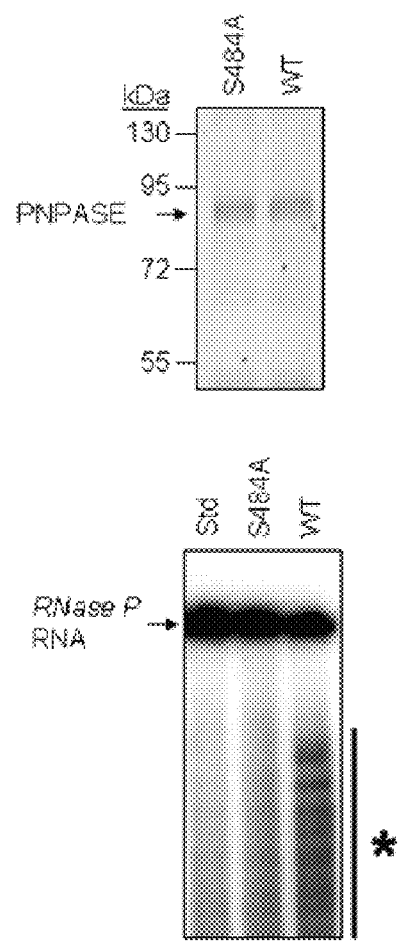
Fig. 11A
Fig. 11B
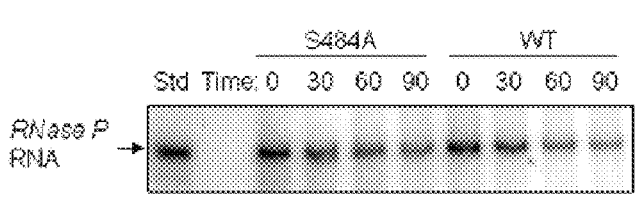
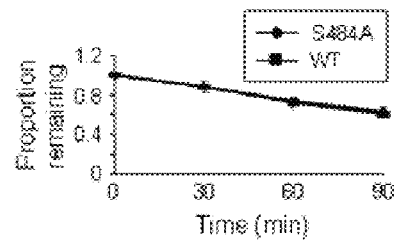
Fig. 11C

SEQUENCE LISTING

```
<160> NUMBER OF SEQ ID NOS: 42

<210> SEQ ID NO 1
<211> LENGTH: 55
<212> TYPE: DNA
<213> ORGANISM: Mus musculus

<400> SEQUENCE: 1
tgactgtaga cctgggacac agtcaggcga tactgcagta atggtcacgg cagtc         55

<210> SEQ ID NO 2
<211> LENGTH: 53
<212> TYPE: DNA
<213> ORGANISM: Mus musculus

<400> SEQUENCE: 2
gtgactgtag acctgggaca cagtcaggcg atactgcagt aatggtcacg gca           53

<210> SEQ ID NO 3
<211> LENGTH: 55
<212> TYPE: DNA
```

```
<213> ORGANISM: Mus musculus

<400> SEQUENCE: 3
ggtgactgta gacctgggac acagtcaggc gatactgcag taatggtcac ggcag         55

<210> SEQ ID NO 4
<211> LENGTH: 54
<212> TYPE: DNA
<213> ORGANISM: Mus musculus

<400> SEQUENCE: 4
gcggtgactg tagacctggg acacagtcag gcgatactgc agtaatggtc acgg          54

<210> SEQ ID NO 5
<211> LENGTH: 20
<212> TYPE: RNA
<213> ORGANISM: Homo sapiens

<400> SEQUENCE: 5
ggcagggccc cccgcucccc                                                 20

<210> SEQ ID NO 6
<211> LENGTH: 20
<212> TYPE: RNA
<213> ORGANISM: Homo sapiens

<400> SEQUENCE: 6
agaagcguau cccgcugagc                                                 20

<210> SEQ ID NO 7
<211> LENGTH: 20
<212> TYPE: RNA
<213> ORGANISM: Homo sapiens

<400> SEQUENCE: 7
ucucccugag cuucagggag                                                 20

<210> SEQ ID NO 8
<211> LENGTH: 59
<212> TYPE: DNA
<213> ORGANISM: Homo sapiens

<400> SEQUENCE: 8
cggggctcat tctcagcgcg gctggatccg cgcaaagtcc gccagaaaag cgtatcccg      59

<210> SEQ ID NO 9
<211> LENGTH: 57
<212> TYPE: DNA
<213> ORGANISM: Homo sapiens

<400> SEQUENCE: 9
ggggcgtcat tctcagcgcg gctggatccg cgcaaagtcc gccagaagc gtatccc         57

<210> SEQ ID NO 10
<211> LENGTH: 265
<212> TYPE: DNA
<213> ORGANISM: Homo sapiens

<400> SEQUENCE: 10
gttcgtgctg aaggcctgta tcctaggcta cacactgagg actctgttcc tccccttcc     60 gcctagggga aagtccccgg acctcgggca gagagtgcca cgtgcatacg cacgtagaca   120
ttccccgctt cccactccaa agtccgccaa gaagcgtatc ccgctgagcg cgtggcgcg   180
```

```
ggggcgtcat ccgtcagctc cctctagtta cgcaggcagt gcgtgtccgc gcaccaacca      240
cacggggctc attctcagcg cggct                                            265

<210> SEQ ID NO 11
<211> LENGTH: 11
<212> TYPE: DNA
<213> ORGANISM: Homo sapiens

<400> SEQUENCE: 11
taaagtgaca t                                                           11

<210> SEQ ID NO 12
<211> LENGTH: 13
<212> TYPE: DNA
<213> ORGANISM: Homo sapiens

<400> SEQUENCE: 12
tctcgggtga cat                                                         13

<210> SEQ ID NO 13
<211> LENGTH: 11
<212> TYPE: DNA
<213> ORGANISM: Homo sapiens

<400> SEQUENCE: 13
atacaacaat t                                                           11

<210> SEQ ID NO 14
<211> LENGTH: 11
<212> TYPE: DNA
<213> ORGANISM: Homo sapiens

<400> SEQUENCE: 14
cccaaacaat t                                                           11

<210> SEQ ID NO 15
<211> LENGTH: 163
<212> TYPE: DNA
<213> ORGANISM: Homo sapiens

<400> SEQUENCE: 15
cagaagaagt gacggctggg ggcacagtgg gctgggcgcc cctgcagaac atgaaccttc      60
cgctcctggc tgccacaggg tcctccgatg ctggcctttg cgcctctaga ggcagccact     120
catggattca agtcctggct ccgcctcttc catcaggacc act                       163

<210> SEQ ID NO 16
<211> LENGTH: 30
<212> TYPE: DNA
<213> ORGANISM: Mus musculus

<400> SEQUENCE: 16
gagaagatct atggcctaac ccattccaac                                       30

<210> SEQ ID NO 17
<211> LENGTH: 54
<212> TYPE: DNA
<213> ORGANISM: Mus musculus

<400> SEQUENCE: 17
gagaagatct atgtctccct gagcttcagg gaggatggcc taacccattc caac            54
```

```
<210> SEQ ID NO 18
<211> LENGTH: 41
<212> TYPE: DNA
<213> ORGANISM: Homo sapiens

<400> SEQUENCE: 18
ccgccgctcg agttaaatta ttgaagcaga tcagttttcg a                 41

<210> SEQ ID NO 19
<211> LENGTH: 29
<212> TYPE: DNA
<213> ORGANISM: Homo sapiens

<400> SEQUENCE: 19
cggccgcacc ggtatggcac atgcagcgc                              29

<210> SEQ ID NO 20
<211> LENGTH: 53
<212> TYPE: DNA
<213> ORGANISM: Homo sapiens

<400> SEQUENCE: 20
cggccgcacc ggtatgtctc cctgagcttc agggaggatg gcacatgcag cgc   53

<210> SEQ ID NO 21
<211> LENGTH: 28
<212> TYPE: DNA
<213> ORGANISM: Homo sapiens

<400> SEQUENCE: 21
cgcggatccc tatagggtaa atacgggc                               28

<210> SEQ ID NO 22
<211> LENGTH: 37
<212> TYPE: DNA
<213> ORGANISM: Homo sapiens

<400> SEQUENCE: 22
cggccgcacc ggtatggaga aataaggcct acttcac                     37

<210> SEQ ID NO 23
<211> LENGTH: 58
<212> TYPE: DNA
<213> ORGANISM: Homo sapiens

<400> SEQUENCE: 23
cggccgcacc ggtatgtctc cctgagcttc agggagggag aaataaggcc tacttcac   58

<210> SEQ ID NO 24
<211> LENGTH: 27
<212> TYPE: DNA
<213> ORGANISM: Homo sapiens

<400> SEQUENCE: 24
cgcggatccc gttcggtaag cattagg                                27

<210> SEQ ID NO 25
<211> LENGTH: 37
<212> TYPE: DNA
<213> ORGANISM: Homo sapiens

<400> SEQUENCE: 25
cggccgcacc ggtatgcatg catgcccatc gtcctag                     37
```

<210> SEQ ID NO 26
<211> LENGTH: 54
<212> TYPE: DNA
<213> ORGANISM: Homo sapiens

<400> SEQUENCE: 26
cggccgcacc ggtatgtctc cctgagcttc agggaggcat gcccatcgtc ctag         54

<210> SEQ ID NO 27
<211> LENGTH: 27
<212> TYPE: DNA
<213> ORGANISM: Homo sapiens

<400> SEQUENCE: 27
cgcggatccg ggtgatgagg aatagtg                                        27

<210> SEQ ID NO 28
<211> LENGTH: 39
<212> TYPE: DNA
<213> ORGANISM: Homo sapiens

<400> SEQUENCE: 28
ccgccgctcg aggggtttgt taagaagagg aattgaacc                           39

<210> SEQ ID NO 29
<211> LENGTH: 36
<212> TYPE: DNA
<213> ORGANISM: Homo sapiens

<400> SEQUENCE: 29
ccgccgctcg agagagccca ctgtaaagag gtgttg                              36

<210> SEQ ID NO 30
<211> LENGTH: 30
<212> TYPE: DNA
<213> ORGANISM: Homo sapiens

<400> SEQUENCE: 30
cgcggatccc atcagaagaa gtgacggctg                                     30

<210> SEQ ID NO 31
<211> LENGTH: 26
<212> TYPE: DNA
<213> ORGANISM: Homo sapiens

<400> SEQUENCE: 31
ccggaattct agtggtcctg atggaa                                         26

<210> SEQ ID NO 32
<211> LENGTH: 20
<212> TYPE: DNA
<213> ORGANISM: Homo sapiens

<400> SEQUENCE: 32
tctccctgag cttcagggag                                                20

<210> SEQ ID NO 33
<211> LENGTH: 20
<212> TYPE: DNA
<213> ORGANISM: Homo sapiens

<400> SEQUENCE: 33
agaagcgtat cccgctgagc                                                20

<210> SEQ ID NO 34
<211> LENGTH: 163
<212> TYPE: DNA
<213> ORGANISM: Homo sapiens

<400> SEQUENCE: 34
cagaagaagt gacggctggg ggcacagtgg gctgggcgcc cctgcagaac atgaaccttc    60
cgctcctggc tgccacaggg tcctccgatg ctggcctttg cgcctctaga ggcagccact   120
catggattca gtcctggct ccgcctcttc catcaggacc act                      163

<210> SEQ ID NO 35
<211> LENGTH: 369
<212> TYPE: DNA
<213> ORGANISM: Homo sapiens

<400> SEQUENCE: 35
atgtctccct gagcttcagg gagggagaaa taaggcctac ttcacaaagc gccttccccc    60
gtaaatgata tcatctcaac ttagtattat acccacaccc acccaagaac agggtttgtt   120
aagatggcag agcccggtaa tcgcataaaa cttaaaactt tacagtcaga ggttcaattc   180
ctcttcttaa caaaccccte ggatcccaga agaagtgacg ctgggggca cagtgggctg    240 ggcgccctg cagaacatga accttccgct cctggctgcc acagggtcct ccgatgctgg    300
cctttgcgcc tctagaggca gccactcatg gattcaagtc ctggctccgc ctcttccatc   360
aggaccact                                                           369

<210> SEQ ID NO 36
<211> LENGTH: 360
<212> TYPE: DNA
<213> ORGANISM: Homo sapiens

<400> SEQUENCE: 36
atgtctccct gagcttcagg gaggcatgcc catcgtccta gaattaattc ccctaaaaat    60
ctttgaaata gggcccgtat ttaccctata gcacccctc taccccctct agagcccact    120
gtaaagctaa cttagcatta acctttaag ttaaagatta agagaaccaa cacctcttta    180
cagtgggctc tggatcccag aagaagtgac ggctgggggc acagtgggct gggcgcccct   240
gcagaacatg aaccttccgc tcctggctgc cacagggtcc tccgatgctg gcctttgcgc   300 tctagaggc agccactcat ggattcaagt cctggctccg cctcttccat caggaccact    360

<210> SEQ ID NO 37
<211> LENGTH: 708
<212> TYPE: DNA
<213> ORGANISM: Homo sapiens

<400> SEQUENCE: 37
atgtctccct gagcttcagg gaggatggca catgcagcgc aagtaggtct acaagacgct    60
acttccccta tcatagaaga gcttatcacc tttcatgatc acgccctcat aatcattttc   120
cttatctgct tcctagtcct gtatgccctt ttcctaacac tcacaacaaa actaactaat   180
actaacatct cagacgctca ggaaatagaa accgtctgaa ctatcctgcc cgccatcatc   240
ctagtcctca tcgccctccc atccctacgc atccttttaca taacagacga ggtcaacgat   300
cccctcctta ccatcaaatc aattggccac caatggtact gaacctacga gtacaccgac   360
tacggcggac taatcttcaa ctcctacata cttcccccat tattcctaga accaggcgac   420

```
ctgcgactcc ttgacgttga caatcgagta gtactcccga ttgaagcccc cattcgtata    480
ataattacat cacaagacgt cttgcactca tgagctgtcc ccacattagg cttaaaaaca    540
gatgcaattc ccggacgtct aaaccaaacc actttcaccg ctacacgacc gggggtatac    600
tacggtcaat gctctgaaat ctgtggagca aaccacagtt tcatgcccat cgtcctagaa    660
ttaattcccc taaaaatctt tgaaataggg cccgtattta ccctatag               708

<210> SEQ ID NO 38
<211> LENGTH: 19
<212> TYPE: RNA
<213> ORGANISM: Homo sapiens

<400> SEQUENCE: 38
gucccugagc uucagggac                                                19

<210> SEQ ID NO 39
<211> LENGTH: 15
<212> TYPE: RNA
<213> ORGANISM: Homo sapiens

<400> SEQUENCE: 39
cccugagcuu caggg                                                    15

<210> SEQ ID NO 40
<211> LENGTH: 11
<212> TYPE: DNA
<213> ORGANISM: Homo sapiens

<400> SEQUENCE: 40
atgtcacccg a                                                        11

<210> SEQ ID NO 41
<211> LENGTH: 13
<212> TYPE: DNA
<213> ORGANISM: Homo sapiens

<400> SEQUENCE: 41
atgtcacccg aga                                                      13

<210> SEQ ID NO 42
<211> LENGTH: 11
<212> TYPE: DNA
<213> ORGANISM: Homo sapiens

<400> SEQUENCE: 42
aattgtttgg g                                                        11
```

US 9,238,041 B2

METHODS AND COMPOSITIONS FOR REGULATING RNA IMPORT INTO MITOCHONDRIA

CROSS-REFERENCE TO RELATED APPLICATIONS

This application claims the benefit of U.S. Patent Application Ser. No. 61/481,890, filed 3 May 2011, and U.S. Patent Application Ser. No. 61/577,300, filed 19 Dec. 2011, both of which are herein incorporated by reference in their entirety.

ACKNOWLEDGEMENT OF GOVERNMENT SUPPORT

This invention was made with Government support of Grant No. CA107300 and GM073981, awarded by the National Institutes of Health. The Government has certain rights in the invention.

REFERENCE TO A SEQUENCE LISTING SUBMITTED VIA EFS-WEB

The content of the ASCII text file of the sequence listing named "20120503_034044_087_ST25" which is 8.6 kb in size was created on 6 Mar. 2012 and electronically submitted via EFS-Web herewith the application is incorporated herein by reference in its entirety.

BACKGROUND OF THE INVENTION

1. Field of the Invention

The present invention relates generally to targeting nucleic acid molecules and mitochondrial diseases and disorders.

2. Description of the Related Art

RNA import into mammalian mitochondria is considered essential for replication, transcription, and translation of the mitochondrial genome and mutations in the human mitochondrial genome are implicated in a plethora of human conditions, such as neurodegenerative and cardiovascular diseases, muscular disorders, and the process of aging. See e.g. Wallace (1994) PNAS USA 91: 8739-8746; and Kyriakouli et al. (2008) Gene Ther 15: 1017-1023. Unfortunately, RNA import pathways and factors that control RNA import are poorly understood. In addition, the in vivo rescue of function in mitochondria with mt-tRNA mutations has proven challenging (Alfonzo & Soll (2009) Biol Chem 390: 717-722). Thus, prior art methods of rescuing mitochondrial function due to defects in mitochondrial genomes have been restricted to correcting the defects by using foreign protein factors or large multi-subunit aggregates to introduce nonnative tRNAs into cells, and these methods have low efficiency and poor reproducibility in disease-relevant settings. See e.g. Kolesnikova et al. (2004) Hum Mol Genet 13: 2519-2534; Mahata et al. (2006) Science 314: 471-474; and Kolesnikova et al. (2000) Science 289: 1931-1933.

Consequently, a need exists for methods and compositions for treating deleterious mitochondrial DNA (mtDNA) alterations.

SUMMARY OF THE INVENTION

The present invention provides a recombinant and/or isolated nucleic acid molecule which comprises, consists essentially of, or consists of a first nucleic acid sequence which may be a wild-type sequence (of a gene or a fragment or complement thereof) or an altered sequence, i.e. a wild-type sequence having one or more mutations, substitutions, and/or deletions (e.g. tRNA with an altered tRNA aminocyl stem) directly or indirectly linked to a second nucleic acid sequence selected from the group consisting of: (1) a mitochondria localization sequence, (2) an RNA import sequence, or (3) a combination thereof. As used herein, the term "recombinant" is used to indicate that the nucleic acid molecule has been engineered using recombinant techniques to combine the first nucleic acid sequence and the second nucleic acid sequence into one contiguous sequence. The first and second nucleic acid sequences may be directly linked (which means that there are no intervening bases between the sequences) or indirectly linked (which means that there may be one or more bases between the sequences). As used herein, the term "isolated" refers to a nucleic acid molecule that is in an environment that is different from its native environment in which the nucleic acid molecule naturally occurs. Isolated nucleic acid molecules include those having nucleotides or other molecules flanking at least one end that is not native to the given nucleic acid molecule. For example, nucleic acid molecule A, as it is found in nature, has sequence B at its 5' end and sequence C at its 3' end. When nucleic acid molecule A does not have sequence B at its 5' end and/or sequence C at its 3' end, it is considered to be "isolated". As used herein, references to nucleic acid molecules, bases and nucleotides include RNA molecules, bases and ribonucleotides. As used herein, an "altered tRNA aminoacyl stem" refers to a tRNA aminoacyl stem that has been elongated and/or modified such that the bases form base pairs rather than a bubble due to unmatched bases. In some embodiments, the RNA import sequence is selected from the group consisting of: (a) SEQ ID NO:6, SEQ ID NO:7, SEQ ID NO:38, SEQ ID NO:39, and complementary sequences thereto; (b) sequences having about 15-30 nucleotides and about 95-99%, preferably 96-99%, more preferably 97-99%, most preferably 98-99%, sequence identity to SEQ ID NO:6, SEQ ID NO:7, SEQ ID NO:38, SEQ ID NO:39, and complementary sequences thereto; and (c) sequences which are about 15-30 nucleotides long and comprise SEQ ID NO:39 or its complement, and wherein the sequences are capable of forming a single stem-loop. In some embodiments, the mitochondrial localization sequence is mammalian. In some embodiments, the mitochondrial localization sequence has 80-100%, preferably 85-100%, more preferably 90-100%, even more preferably 95-100%, or most preferably 97-100%, sequence identity to SEQ ID NO:34 or its complement. A first sequence having a given percent (%) sequence identity with respect to a second sequence is defined as the percentage of amino acid residues (or nucleotide bases) in the first sequence that are identical with the amino acid residues (or nucleotide bases) in the second sequence, after aligning the first and second sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as ALIGN, ALIGN-2, Megalign (DNASTAR) or BLAST (e.g., Blast, Blast-2, WU-Blast-2) software. Those skilled in the art can determine appropriate parameters for measuring alignment, including any algorithms needed to achieve maximal alignment over the full length of the sequences being compared. For example, the % identity values used herein are generated using WU-BLAST-2 (Altschul et al., *Methods in Enzymology* 266: 460-480 (1996). Most of the WU-BLAST-2 search parameters are set to the default values. For purposes herein, the default parameters of the BLAST alignment tools available online at blast.ncbi.nlm.nih.gov/Blast.cgi were used. In some embodiments, the altered tRNA aminoacyl stem has a sequence that is substantially similar to a wild-type aminoacyl stem or its complement but contains nucleotide substitutions and/or additions which result in nucleotide pairing along the tRNA aminoacyl stem. As used herein, the term "wild-type sequence" refers to a gene or fragment thereof that is most frequently observed in a population and is thus arbitrarily designed the "normal" or "wild-type" form. In contrast, the terms "modified", "mutant", or "altered" sequence is one that has one or more substitutions, mutations, alterations, deletions or changes in the sequence and/or its functional characteristics as compared to the corresponding wild-type sequence. It is noted that naturally-occurring mutants can be isolated; these are identified by the fact that they have altered characteristics when compared to the wild-type sequence. As used herein, the term "gene" refers to a nucleic acid (e.g. RNA, DNA) sequence that comprises coding sequences necessary for the downstream production of a product such as a protein. In some embodiments, the first nucleic acid sequence and the second nucleic acid sequence are not natively associated with each other. In other words, the combination of the first and second nucleic acid sequences do not naturally occur operably linked to each other in nature.

In some embodiments, the present invention provides a method of manipulating the processing, targeting, and/or internalization of a nucleic acid molecule which comprises, consists essentially of, or consists of one or more of the following steps: altering its nucleic acid sequence to thereby enable the nucleic acid molecule to escape the nucleus of a cell without being processed, or prevent it from being targeted to a location other than mitochondria; providing a mitochondria localization sequence that is directly or indirectly linked to the nucleic acid molecule to thereby cause the nucleic acid molecule to localize in the proximity of a mitochondrion; and providing an RNA import sequence that is directly or indirectly linked to the nucleic acid molecule to thereby cause the nucleic acid molecule to be internalized by a mitochondrion. In these embodiments, the nucleic acid molecule may be the first nucleic acid sequence as set forth above and the sequence that is linked thereto may be the second sequence as set forth above in paragraph [14]. In some embodiments, the nucleic acid molecule, i.e. first nucleic acid sequence, is a nucleus-encoded non-coding RNA such as micro-RNA and riboenzyme. In some embodiments, the nucleic acid molecule, i.e. first nucleic acid sequence, is a wild-type sequence of a gene (or fragment thereof) or its complement in the mitochondrial genome of a mammalian subject.

In some embodiments, the present invention provides a method of treating a mitochondrial disease caused by a mutation in a gene or its complement in the mitochondrial genome of a mammalian subject which comprises, consists essentially of, or consists of administering to the subject a recombinant and/or isolated nucleic acid molecule of the present invention, i.e. one which comprises, consists essentially of, or consists of a first nucleic acid sequence, which may be a wild-type or an altered sequence, directly or indirectly linked to a second nucleic acid sequence selected from the group consisting of: (1) a mitochondria localization sequence, (2) an RNA import sequence, or (3 a combination thereof, wherein the first nucleic acid sequence is the wild-type sequence of the gene or its complement. In some embodiments, the mitochondrial disease is myoclonic epilepsy with ragged red fibers (MERRF) or mitochondrial encephalomyopathy, lactic acidosis and stroke-like episodes (MELAS).

The present invention also provides vectors and host cells which comprise, consist essentially of, or consist of a recombinant and/or isolated nucleic acid molecule of the present invention.

According to the present invention, the first nucleic acid sequence may be DNA or RNA. Similarly, in some embodiments, the RNA import sequence and/or the mitochondria localization sequence may be in their DNA form, e.g. in the case of the vector form of the recombinant nucleic acid molecule. In some embodiments, the recombinant nucleic acid molecule is a DNA:RNA hybrid.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1A is an immunoblot showing that the PNPASE-HisPC retroviral construct was stably expressed in HEK293 cells. FIG. 1B is a gel showing purified PNPASE-HisPC isolated from HEK293 cell mitochondria. FIG. 1C is an immunoblot showing PNPASE in a complex of about 240 kDa when expressed in yeast. FIG. 1D is an immunoblot showing PNPASE-HisPC assembles into the same complex as endogenous PNPASE in HEK293 cells.

FIG. 2A schematically shows the targeting construct which encodes PNPASE. The targeting construct was generated using two loxP sites (triangles) flanking exon 2 of the mouse Pnpt1 gene. Between exon 2 and the 3' loxP site, a PGK-NEO selection cassette was inserted into intron 2. Exon 2 and the PGK-NEO cassette were deleted by backcrossing the mice with $CMV^{CRE}$ or $Alb^{CRE}$ (Albumin promoter) deleting strains (C57BL/6). Excision of the 35 by exon 2 sequence generates a Pnpt1 mRNA that translates out-of-frame with multiple downstream stop codons in exons 3, 4, and 6. S=SnaB1. FIG. 2B shows a PCR genotyping schematic (left) and a PCR agarose gel (right) of wild type (WT) and loxP flanked Pnpt1 exon 2 (neo-flox) genomic tail DNA. FIG. 2C shows a PCR genotyping schematic (left) and a touch-down PCR agarose gel (right) of liver genomic DNA from $Alb^{CRE/WT}$/$Pnpt1^{neo-flox/neo-flox}$×$Alb^{WT/WT}$/$Pnpt1^{neo-flox/neo-flox}$ breeding to generate hepatocyte-specific $Pnpt1^{HepKO}$ (HepKO) mice.

FIG. 3A-3F evidence that excision of Pnpt1 exon 2 generates truncated PNPASE transcript in HepKO liver cells and mouse embryonic fibroblasts (MEFs). FIG. 3A is an RT-PCR schematic for excision of the Pnpt1 exon 2 by hepatocyte-specific $Alb^{CRE}$. FIG. 3B is an agarose RT-PCR gel showing WT and HepKO Pnpt1 (KO) RNA transcripts. The age of sex matched littermate mice in weeks is listed above the genotype for each lane. FIG. 3C shows the RNA sequences (listed as DNA) isolated from week 15 (SEQ ID NO:1) and week 7.3 (SEQ ID NO:2) HepKO mouse livers (arrows in FIG. 3B) and the first of many predicted stop codons in Pnpt1 exon 3 (boxed). FIG. 3D is an RT-PCR schematic for excision of the Pnpt1 exon 2 by a $CMV^{CRE}$ expressing retrovirus. FIG. 3E is an agarose RT-PCR gel showing MEFs with loxP flanked Pnpt1 exon 2 (Flox) and MEFs infected with $CMV^{CRE}$ retrovirus (KO-1, KO-2) analyzed for Pnpt1 RNA transcripts. FIG. 3F shows the RNA sequences isolated from KO-1 (SEQ ID NO:3) and KO-2 (SEQ ID NO:4) MEFs (the bands with the arrows in FIG. 3E) and the first of many predicted stop codons in Pnpt1 exon 3 (boxed).

FIGS. 4A-4E evidence that deletion of Pnpt1 in hepatocytes impairs mitochondrial function. FIG. 4A shows the breeding strategy and results for generating a PNPASE KO mouse. FIG. 4B shows hepatocyte-specific Pnpt1 KO (HepKO) expression in 4-week old mice. Top: QPCR for liver Pnpt1 expression using an exon 2-exon 3 primer pair versus a primer pair within exon 28. Bottom: PNPASE immunoblot from 4-week old WT and HepKO mouse livers. FIG. 4C shows that HepKO mitochondria have altered cristae. Left: TEM micrographs of 6-week old littermate livers shows circular, smooth HepKO IM cristae in contrast to linear, stacked cristae of WT mitochondria. Right: Analysis of cristae morphology in which a single normal cristae within a mitochondrion was scored as normal. Indet=indeterminate. FIG. 4D shows decreased respiration in isolated HepKO mitochondria. Respiratory activities are shown normalized to citrate synthase (CS) activity. FIG. 4E shows decreased mature mtRNAs in HEK293 cells with RNAi to PNPT1.

FIG. 5A is a gel of proteins translated from mtRNAs of HepKO liver cells in organello. WT and HepKO mitochondria (100 µg) were treated with micrococcal nuclease S7, and in organello translation was performed using [$^{35}$S]-MET. The TOM40 immunoblot shows equivalent mitochondria in each assay. FIG. 5B schematically shows the RT-PCR primers and expected fragments. FIG. 5C shows a Northern blot of mtRNA from WT and HepKO mouse liver mitochondria using a Cox1 or Cox3 DNA probe. * marks larger precursor mtRNAs and the arrow shows the mature mtRNA. FIG. 5D is a blot showing the steady-state expression of nuclear (TOM40, MORTALIN, TIM23, and BAP37) and mitochondrial (COX3 and ND6) encoded proteins in WT and HepKO liver mitochondria.

FIG. 6A (lower) is a gel showing RNA isolated from WT and PNPASE KO MEF mitochondria following DNase I treatment. RT-PCR was performed for Cox1 and Cox2 with primers highlighted in the schematic (upper) and separated on a 1.5% agarose gel. As a control, samples treated with DNase I followed by RT-PCR verified that DNA was not amplified in the PCR reaction (data not shown). FIG. 6B (lower) shows the Atp8/6 and Cox2 mtRNA transcripts using the same approach as in FIG. 6A with distinct primer pairs for Atp8/6. * is a non-specific band.

FIG. 7A (left) is a gel showing RNase P RNA isolated from WT and HepKO liver mitochondria following nuclease treatment. RT-PCR was performed with primers that amplify nuclear-encoded RNase P RNA (212-bp). FIG. 7A (right) shows QPCR analysis of RNase P RNA expression relative to TOM40 protein in isolated mitochondria. FIG. 7B are gels showing PNPASE-HisPC (PNP) or TIM23-HisPC (TIM23) purified from stably-transfected HEK293 cells. Candidate interacting RNAs that co-purified in the final eluate with PNPASE-HisPC and TIM23-HisPC were identified by primer-specific RT-PCR. T is the total lysate (0.3% of the reaction) before mitochondrial purification and B is the bound fraction. Note that only RNase P RNA bound to PNPASE-HisPC (lane 4). FIG. 7C shows RNA dependent RNase P RNase activity is involved in processing of abutted tRNA precursors. Single tRNA precursors or abutted tRNA precursors were incubated with mitoplast extract (10 µg) of WT liver mitochondria treated with Nuclease or without the treatment. A MORTALIN immunoblot shows equivalent mitoplast extract in each assay. FIG. 7D shows the processing of abutted tRNA precursors is less efficient by mitoplast extract of HepKO liver mitochondria. The enzymatic assay was performed as described for FIG. 7C.

FIG. 8A are gels showing that PNPASE-HisPC, but not TIM23-HisPC, bound in vitro transcribed and imported RNase P and MRP RNAs, but not control mitochondrial RNA, in cross-linking IP assays. Briefly, radiolabeled RNA substrates were incubated with mitochondria containing PNPASE-HisPC. The samples were UV-crosslinked and PNPASE-HisPC purified using Ni-NTA bead (Qiagen, Valencia, Calif.). FIG. 8B are gels showing that the in vivo processing and separation of an endogenous paired tRNA$^{his}$tRNA$^{ser}$ substrate was inhibited in HepKO compared to WT liver mitochondria, whereas a linked 12s rRNA-tRNA$^{val}$ substrate was processed equivalently.

FIG. 9A is an immunoblot showing human PNPT1 encoding PNPASE was expressed in S. cerevisiae under the control of the CUP1 promoter (PNP) using methods known in the art. See Rainey et al. (2006) Mol Cell Biol 26:8488-8497. Yeast were also transduced with an empty vector control (Vec). Anti-PNPASE antibody and an anti-PORIN antibody were used show the expression of PNPASE and equal loading of mitochondria. FIG. 9B are pictures showing that the mitochondrial morphology of control and PNPASE-expressing yeast strains was visually equivalent, as determined by MitoTracker Red staining (Invitrogen brand of Life Technologies, Carlsbad, Calif.). FIG. 9C is a graph showing the growth kinetics, determined over a 10-hr time period, of PNPASE-expressing and control yeast strains diluted to an $OD_{600}$ of 0.1. FIG. 9D graphically shows the viability, by a standard colony survival assay, over 5 days of PNPASE-expressing and control yeast strains.

FIGS. 10A-10D show that PNPASE augments RNase P, 5S rRNA, and MRP RNA import into yeast mitochondria. FIG. 10A (upper) is a gel showing in vitro transcribed human RNase P RNA incubated with yeast mitochondria expressing human PNPT1 (PNP) or an empty vector (Vec) control. Non-imported RNA was digested with nuclease and the imported RNA was detected by RT-PCR. PNPT1-expressing mitochondria without added RNase P RNA was included as a specificity control for import and RT-PCR (lane 2—Std, 1% of the reaction). FIG. 10A (lower) is an immunoblot showing a control having equivalent total mitochondrial nucleic acid in each reaction. FIG. 10B (upper) is a gel showing, as in FIG. 9A, cytosolic human GAPDH RNA used as a substrate, (middle) is an immunoblot showing a control having equivalent total mitochondrial nucleic acid in each reaction, and (lower) is a Western blot showing PNPASE and PORIN expression having equivalent mitochondria in each import assay. FIG. 10C shows RNase P RNA is imported into mitochondrial matrix. Mitochondria were subjected to osmotic shock, fractionated by centrifugation into soluble (S) and pellet (P) fractions, followed by proteinase K and nuclease additions where indicated. The pellet fraction was solubilized with Triton X-100 to expose the matrix. Localization was determined by RT-PCR for RNase P RNA and immunoblot for KDH (matrix) and cyt $b_2$ (IMS) proteins. FIG. 10D (upper) shows radiolabeled RNase P, MRP, 5S rRNA, and GAPDH human RNAs which were in vitro transcribed and then incubated with yeast mitochondria expressing PNPASE or an empty vector control. Non-imported RNA was digested with nuclease, followed by RNA isolation, separation on a urea acrylamide gel, and autoradiography. Import reactions were repeated with 1× and 2× amounts of RNA, and (lower) a control showing equivalent total mitochondrial nucleic acid in each reaction. FIG. 10E (upper) is an immunoblot showing, as in FIG. 10A, RNase P RNA except that the mitochondrial membrane potential (Δψ) was dissipated prior to import, and (lower) a control showing equivalent total mitochondrial nucleic acid in each reaction.

FIGS. 11A-11C show that PNPASE mutations that inactivate RNA processing do not affect RNA import or stability. FIG. 11A (upper) shows a schematic for the positions of point mutations made in the PNPASE protein. Listed are the in vitro effects of mutations on 3' polymerase and RNA degrading activities as reported by Portnoy et al. (2008) RNA 14: 297-309. FIG. 11A (middle) shows an immunoblot of import reactions performed as in FIG. 10A. Radiolabeled RNase P RNA was incubated with isolated yeast mitochondria expressing an empty vector or the listed PNPASE constructs. FIG. 11A (lower) shows the PNPASE mutants were expressed at the similar level as the wild-type PNPASE and also assembled into same size complex in yeast. A PORIN immunoblot confirms the co-localization of PNPASE WT and mutants in yeast mitochondria. The assembly state of WT and point mutant PNPASE was determined by solubilization with 1% digitonin and separation on a 6-16% BN gel, followed by PNPASE immunoblot. FIG. 11B (upper) show gels of WT and S484A PNPASE purified from yeast mitochondria using immunoprecipitation. FIG. 11B (lower) show gels of WT or S484A mutant PNPASE was incubated with radiolabeled RNase P RNA for 10 min at 25° C. to assess degradation activity. The asterisk marks degradation products. FIG. 11 C (left) is a gel showing the stability of RNase P RNA imported into mitochondria. FIG. 11C (right) graphically shows the amount of remaining RNase P RNA corresponding to the time after import; n=3.

FIG. 12A is a schematic depiction of human RNase P RNA and deletion fragments. FIG. 12B is a gel showing the import of full length RNase P RNA into yeast mitochondria expressing PNPASE (PNP) or control (Vec) vectors. FIG. 12C is a gel showing the import of the indicated RNase P RNA fragments. FIG. 12D is a gel showing the import of RNase P RNA fragments RPf3 and RPf4. FIG. 12E is a gel showing the import of human GAPDH mRNA or GAPDH mRNA with control (CR), MRP RNA, or RNase P (RP) RNA 20 nt sequences (as set forth in FIG. 12F) fused to the 5' end. FIG. 12F shows the secondary structures and sequences of mitochondrial RNA targeting signals in RNase P (RP) and MRP (MRP) RNAs. A random sequence (CR) was used as a control (SEQ ID NO:5). As shown, MRP is SEQ ID NO:6 and RNase P (RP) is SEQ ID NO:7. FIG. 12G is a gel showing the tRNA with the RP import sequence interacts with PNPASE during import. Upper panel is a control showing equal amount of RNAs were used. Isolated mitochondria from HEK293 cells stably expressing IMS-localized PNPASE-HisPC or TIM23-HisPC (control) were subjected to incubation with [$^{32}$P]-CTP labeled CR-tRNA$^{trp}$ or RP-tRNA$^{trp}$, followed by UV-cross linking, tag-IP, separation by SDS-PAGE, and autoradiography.

FIG. 13A (upper) shows a human RNase P RNA yeast expression construct driven by the RPM1 RNA promoter, NME1. FIG. 13A (lower) is a gel showing the levels of RNAs in yeast mitochondria. Mitochondria from yeast expressing human RNase P RNA and either PNPASE (PNP) or an empty vector (Vec) were isolated and treated with nuclease. RNA was then isolated from the total cell lysate or from nuclease-treated mitochondria (Mito) and analyzed by primer-specific RT-PCR. FIG. 13B graphically shows the abundance from QPCR for Cox1 and RNase P RNAs isolated from mitochondria in FIG. 13A, normalized to the total mitochondrial RNA obtained. FIG. 13C are immunoblots showing radiolabeled, in vitro transcribed RNase P RNA was imported into mitochondria from MEF cell lines WT (expressing mouse PNPASE, mPNP), Pnpt1 knockout (KO), PNPT1 over-expression (expressing mPNP and hPNP), or Pnpt1 knockout plus PNPT1 over-expression (expressing hPNP). FIG. 13C (upper) is an immunoblot for mouse and human PNPASE expression. FIG. 13C (middle) is an immunoblot of β-ACTIN, a loading control. FIG. 13C (lower) is an autoradiogram of RNase P RNA import into isolated MEF mitochondria. FIG. 13D shows gels of radiolabeled, in vitro transcribed RNAs that were incubated with WT or HepKO liver mitochondria for 10 min at 25° C. Non-imported RNA was removed with nuclease, followed by RNA isolation and separation on a urea-acrylamide gel. Import reactions were repeated with 1× and 2× amounts of synthesized RNAs. The TOM40 immunoblot served as a mitochondrial loading control.

FIG. 14A is a schematic of intact human RNase P RNA (SEQ ID NO:7) and RNase P RNA with its stem-loop replaced by the control random 20 nt RNA sequence, CR (SEQ ID NO:5). Mitochondria from yeast expressing human RNase P RNA (FIG. 14B) or CR-RNase P RNA (FIG. 14C) and either PNPT1 (PNP) or an empty vector control (Vec) were isolated and treated with nuclease. RNA was then isolated from the total cell lysate or from nuclease-treated mitochondria (Mito) and analyzed by RT-PCR using primers for RNase P, HOT13, or RPM1 RNAs. FIG. 14D is a graph showing the amount of RNase P or CR-RNase P RNAs isolated from mitochondria in FIG. 14B, normalized to the total mitochondrial RNA obtained. FIG. 14E schematically shows how MRP RNA was engineered to contain a BamH1 site and 3 nt (GAG) sequence on its 3'-terminus to differentiate exogenous from endogenous MRP RNA. Following PNPASE-dependent import into isolated MEF mitochondria, the RNA was isolated, cloned and sequenced, revealing that the tagged exogenous and imported MRP RNA was processed at the correct site (FIG. 14E the sequencing data). The sequences shown from top to bottom are SEQ ID NO:8, SEQ ID NO:9, and SEQ ID NO:10.

FIG. 15A is an immunoblot from 6-week old WT and HepKO mouse livers showing about a 50% reduction in PNPASE expression. FIG. 15B are gels of radiolabeled mt-tRNA precursors with (top) or without (middle) a 5' H1 20-ribonucleotide predicted stem-loop sequence (designated RP) that were in vitro transcribed and incubated with WT or HepKO liver mitochondria. Non-imported RNA was digested with added nuclease, followed by RNA isolation, separation on a urea acrylamide gel, and autoradiography. Import reactions were repeated with 1× and 2× amounts of mt-tRNA. FIG. 15B (lower) are control gels showing equivalent amounts of mitochondria as used in the imports as revealed by separation of total mitochondrial nucleic acids.

FIG. 17A are diagrams of mCOX2 expression vectors. FIG. 17B is a gel showing mitochondria RNA isolated from HeLa cells expressing mCOX2 or RP-mCOX2. Mitoplasts were made with digitonin, followed by treatment with nuclease. RNA was then isolated from total cell lysates (Input) or from nuclease-treated mitoplasts (Mito) and analyzed by primer-specific RT-PCR. hCOX1 is a control for total and mitochondria-isolated RNAs. FIG. 17C is a Western blot showing that mitochondria isolated from mouse embryonic fibroblasts stably express hCOX2 or RP-hCOX2.

FIG. 19A is a schematic of the mt-tRNA precursors generated for the in vivo rescue assay. The single stem-loop is the H1 RNA import sequence, RP import sequence. The grey box indicates ribonucleotides that were changed to make tRNA precursors less susceptible to processing in the nucleus. The black box is the 3'-UTR of MRPS12 that localizes RNA to the vicinity of mitochondria. The stem-loop sequences shown are, from left to right, SEQ ID NO:40, SEQ ID NO:11, SEQ ID NO:41, SEQ ID NO:12, SEQ ID NO:42, SEQ ID NO:13, SEQ ID NO:42, and SEQ ID NO:14. The 3'-UTR of MRPS12sequence below the stem-loops is SEQ ID NO:15. FIG. 19B shows that tRNALys precursors lacking one or two of the three elements do not rescue the MERRF respiratory defect. FIG. 19C shows that tRNALys or tRNALeu precursors with all three elements rescue respiration in MERRF and MELAS cells.

FIG. 20C shows isolated tRNAs that were modified with the addition of several ribonucleotides adjacent to the aminoacyl stem (see the schematic in FIG. 19A), designated LeuA, LysA, Pre-RPLeuA, and Pre-RPLysA. Export was analyzed as in FIGS. 20A and 20B.

FIG. 21A is a gel showing in vivo mitochondrial translated proteins by the indicated stable cell lines. Mitochondrial translated proteins were separated by SDS-PAGE and visualized by autoradiography. FIG. 21B graphically shows the quantification of specific bands on gels from FIG. 21A. FIG. 21C are gels showing the steady-state levels of nuclear-encoded and mitochondrial-encoded proteins in WT, MERRF, and MELAS cells. TOMM40 and PNPASE served as loading controls.

DETAILED DESCRIPTION OF THE INVENTION

Figure 1A:
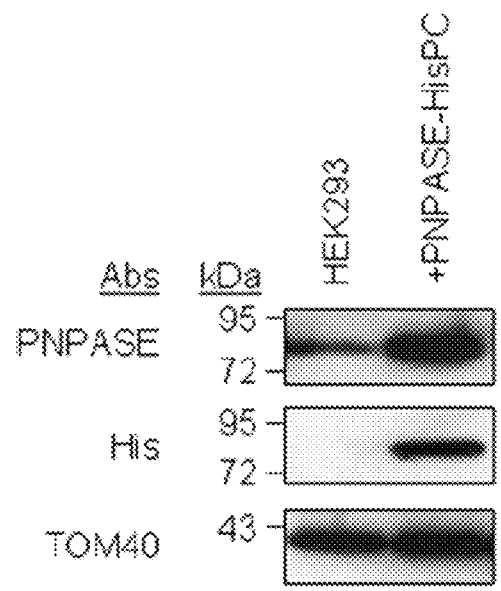
FIGS. 1A-1D show that PNPASE assembles into a trimeric complex.

The present invention is directed to methods and compositions for localizing and/or importing nucleic acid molecules, such as RNA and DNA, into mammalian mitochondria.

The results herein indicate that PNPASE is the first RNA import factor that mediates the translocation of specific RNAs into the mammalian mitochondrial matrix. As provided herein, PNPASE KO disrupts mitochondrial morphology and respiration in mouse liver cells, at least partially by inhibiting the import of RNAs that control the transcription and translation of the ETC proteins. The results herein also indicate that a nucleic acid component of the RNase P RNA processing complex is imported in vivo to process linked tRNAs in long mitochondrial transcripts. PNPASE mediated RNA delivery into the mitochondrial matrix and this import was augmented over background. Strikingly, PNPASE RNA import and RNA processing functions were separable and predicted stem-loop structures were identified in two imported RNAs that could transfer PNPASE-dependent import potential to non-imported RNAs.

A. PNPASE

Mammalian polynucleotide phosphorylase (PNPASE), a 3'→5' exoribonuclease and poly-A polymerase that uses phosphorolysis to degrade RNA, localizes in the mitochondrial intermembrane space (IMS). See Chen et al. (2007) Trends Cell Biol 17:600-608; Chen et al. (2006) Mol Cell Biol 26:8475-8487; and Rainey et al. (2006) Mol Cell Biol 26:8488-8497. The following experiments show that PNPASE plays an important role in importing RNA components into the mitochondrial matrix of mammalian mitochondria.

Methods and Materials

Protein and RNA Purification

For protein-RNA interactions, mitochondria (1 mg/ml) were solubilized in lysis buffer (300 mM NaCl, 10 mM imidazole, 10% glycerol, 0.25% Triton X-100, 2 mM DTT, 20 mM HEPES pH 6.6) containing protease inhibitor (Roche Applied Science, Indianapolis, Ind.) and RNase inhibitor (Invitrogen brand of Life Technologies, Carlsbad, Calif.). Insoluble material was removed by spinning and extracts transferred to microcentrifuge tubes. 50 µl of $Ni^{2+}$NTA resin (Qiagen Inc., Valencia, Calif.) was incubated in 1 ml lysis buffer with 100 µg/ml ssDNA for 1 h at 4° C. The resin was then mixed with the mitochondrial lysates in the presence of 100 µg/ml ssDNA for 1 h at 4° C. After incubation, the resin was washed 10× with lysis buffer containing RNase inhibitor. The protein-RNA complex was eluted with elution buffer (300 mM NaCl, 10 mM imidazole, 10% glycerol, 0.25% Triton X-100, 20 mM citrate pH 5.5) containing RNase inhibitor. RNA was isolated from the eluate using TRIzol reagent (Invitrogen).

Isolation of Mitochondrial RNA and DNA.

Mitochondria (1 mg/ml) were treated with 25 mg/ml of micrococcal nuclease S7 in nuclease buffer (0.6 M Sorbitol, 20 mM $MgCl_2$, 5 mM $CaCl_2$, 20 mM Tris pH 8.0) for 30 min at 27° C. The reaction was stopped by addition of 20 mM EGTA. Mitochondria were collected and solubilized in SDS buffer (100 mM NaCl, 1% SDS, 20 mM Tris pH 7.4) at 65° C. for 5 min. RNA was purified using TRIzol reagent, and treated with RNase-free DNase I (Roche Applied Science) for 1 h at 37° C. DNase I was inactivated by heating at 65° C. for 10 min. Phenol-chloroform (EM Science, division of EM Industries, Inc., Gibbstown, N.J.) extractions were used for DNA purification from the mitochondrial lysates.

In Vitro Transcription

RNAs were synthesized as previously described (Portnoy et al. (2008) RNA 14: 297-309). For radiolabeled RNA synthesis, [$^{32}$P]-CTP (MP Biomedicals, Solon, Ohio) was incorporated. The RNAs were purified using TRIzol reagent.

RNA Import Assay

Yeast mitochondria were isolated from cells grown in selection medium until stationary phase and mammalian mitochondria were isolated as previously described (Chen et al. (2006) Mol Cell Biol 26:8475-8487; and Rainey et al. (2006) Mol Cell Biol 26:8488-8497). In vitro RNA import assays were performed in a 200-μl volume containing 0.5 μg of RNA, 100 μg of mitochondria, 0.6 M sorbitol, 2 mM $KH_2PO_4$, 50 mM KCl, 10 mM $MgCl_2$, 2.5 mM EDTA, 5 mM L-methionine, 1 mg/ml BSA, 5 mM ATP, 2 mM DTT, 5 mM NADH, 50 mM HEPES, pH 7.1, at room temperature for 10 min. Mitochondria were spun at 11,000×g for 5 min and washed once with wash buffer (0.6 M sorbitol, 20 mM Tris, pH 8.0). Mitochondria were spun again and resuspended in 200 μl nuclease buffer containing 25 μg/ml of micrococcal nuclease S7 and incubated for 30 min at 27° C. Mitochondria were collected and solubilized in SDS buffer at 65° C. for 5 min. RNA was purified using TRIzol reagent. For import into mammalian mitochondria, 0.25 M sucrose instead of 0.6 M sorbitol, and 20 mM succinate instead of 5 mM NADH, were used. For import with radiolabeled RNA, the purified RNAs were analyzed by SDS-PAGE and autoradiography.

RNA Degradation Assay

The RNA processing activity of wild-type (WT) and mutant PNPASE was done as before (Portnoy et al. (2008) RNA 14: 297-309). [$^{32}$P]-RNA was incubated with the corresponding proteins in buffer E (20 mM HEPES, pH 7.9, 60 mM KCl, 12.5 mM $MgCl_2$, 0.1 mM EDTA, 2 mM DTT, and 17% glycerol, 0.1 mM $P_i$) at 25° C. for 5 min. Following incubation, the RNA was isolated and analyzed by SDS-PAGE and autoradiography.

Additional Procedures

Osmotic shock was performed by incubating mitochondria for 30 min on ice in 0.03 M sorbitol and 20 mM Hepes-KOH, pH 7.4 (Claypool et al. (2006) J Cell Biol 182: 937-950). Blue native gel electrophoresis was performed on a 6-16% linear polyacrylamide gradient using 50 μg of digitonin solubilized material (Chen et al. (2006) Mol Cell Biol 26:8475-8487). Northern blotting was performed as previously described (Tollervey at al. (1987) EMBO J 6:4169-4175). Total mtRNA was separated on a 12% agarose-formaldehyde gel and transferred to a nylon membrane. Hybridization was carried out with [$^{32}$P]-dCTP (MP Biomedicals) labeled DNA probes. In organello protein synthesis assays were performed as before (Stuart & Koehler (2007) Curr Protc Cell Biol Ch. 11, Unit 11.19) with minor changes on the composition of translation buffer. Specifically, 100 μg mouse liver mitochondria were incubated in 100 μl translation buffer (250 mM sucrose, 100 mM KCl, 1 mM $MgCl_2$, 10 mM Tris pH 7.4, 10 mM $K_2HPO_4$ pH 7.4, 10 mM glutamate, 10 mM malate, 5 mM NADH, 1 mM ADP, 1 mg/ml BSA, 100 μg/ml emetine, 100 μg/ml cycloheximide, and 30 μM of amino acid mix without methionine) with 5 μl of L-[$^{35}$S] methionine (MP Biomedicals) at 37° C. for 30 min. The mitochondria were then precipitated and proteins resolved by 12% SDS PAGE.

Results

PNPASE Forms a Trimer in Yeast and Mammalian Mitochondria

Figure 1B:
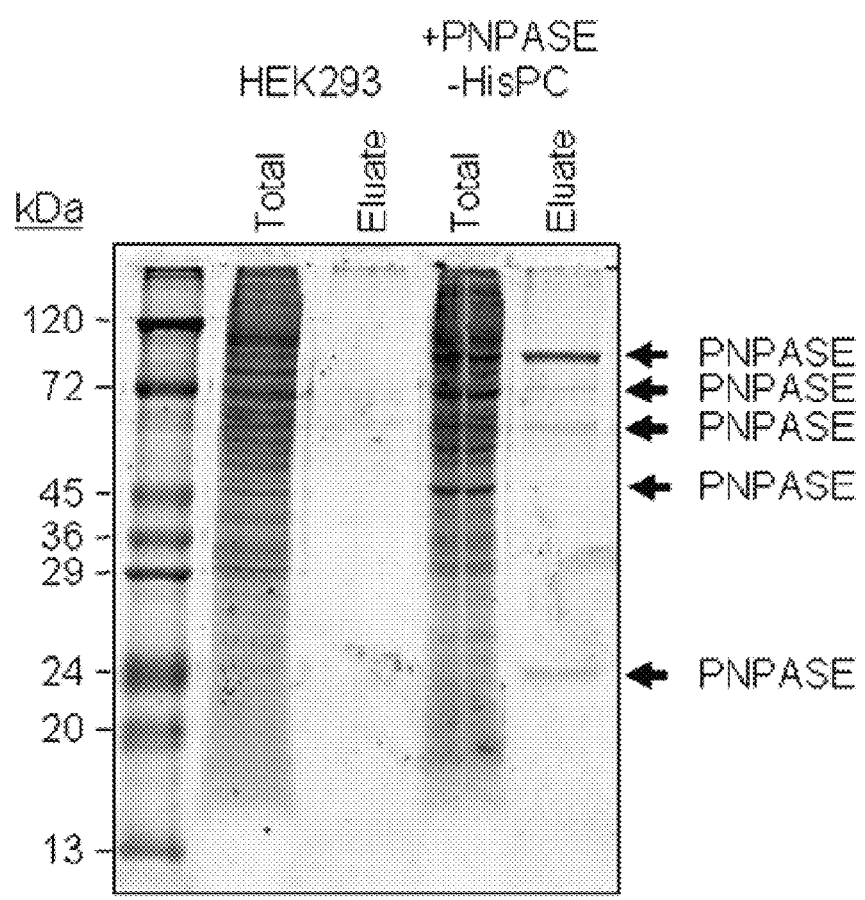

To examine PNPASE in the IMS, a co-immunoprecipitation (IP) assay was performed to identify potential binding partners. A 6×His-Protein-C (HisPC) tag was added to the C-terminus of PNPASE and stable PNPASE-HisPC expressing HEK293 cells were generated using methods known in the art. FIG. 1A is an immunoblot showing that the PNPASE-HisPC retroviral construct was stably expressed in HEK293 cells. Mitochondria were purified from WT (HEK293) and PNPASE-HisPC infected cells, followed by immunoblot detection with antibodies against PNPASE and the His-tag. TOM40 was used as a mitochondrial loading control. Purification of the PNPASE-HisPC protein complex was performed as previously described. See Claypool et al. (2008) J Cell Biol 182:937-950. FIG. 1B is a gel showing purified PNPASE-HisPC isolated from HEK293 cell mitochondria. PNPASE-HisPC isolated from HEK293 cell mitochondria were purified sequentially using $Ni^{2+}$ and Protein-C columns. Bound proteins were eluted, separated by SDS-PAGE, and visualized with Sypro® Ruby Protein stain (Invitrogen, Eugene, Oreg.). Proteins were identified by liquid chromatography-tandem mass spectrometry (LC-MS/MS) (data not shown). All of the identified bands originated from PNPASE, thereby indicating that PNPASE lacks partner proteins in vivo. Bands of molecular weights lower than the PNPASE monomers of about 85 kDa were likely degradation products.

Figures 1C, 1D:
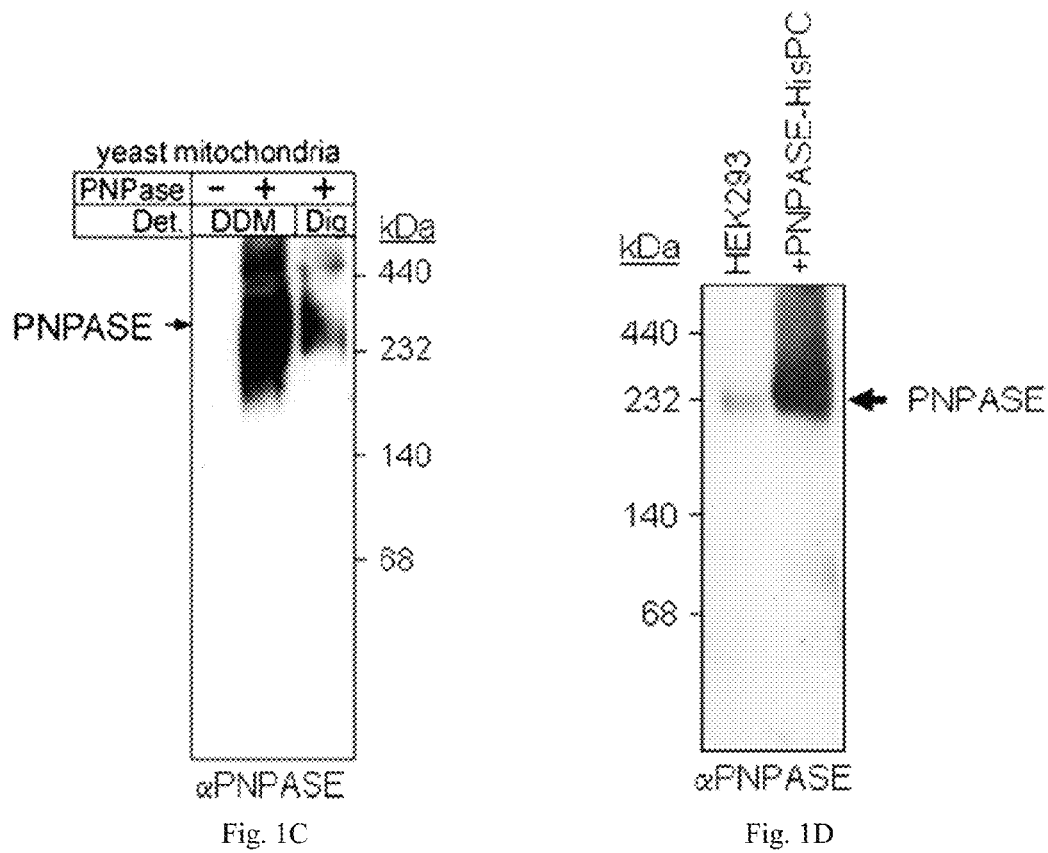

The assembly state of PNPASE was also investigated. Mitochondria from yeast expressing human PNPASE (Rainey et al. (2006) Mol Cell Biol 26:8488-8497) were detergent solubilized and separated on blue-native (BN) gels. FIG. 1C is an immunoblot showing PNPASE in a complex of about 240 kDa similar to the trimeric complex of endogenous mouse hepatocyte PNPASE (Chen et al. (2006) Mol Cell Biol 26:8475-8487) and bacterially-expressed human PNPASE (French et al. (2007) Cancer Lett 248:198-210). Mitochondria were purified from yeast cells expressing human PNPASE and solubilized with 1% digitonin (Dig) or 0.5% dodecylmaltoside (DDM). Soluble proteins were separated on a 6-16% BN gel and PNPASE was detected by immunoblot. The PNPASE antibody did not cross-react with WT yeast mitochondria (first lane). FIG. 1D is an immunoblot showing PNPASE-HisPC from HEK293 mitochondria also migrated in a similarly-sized complex. The PNPASE-HisPC were solubilized with 1% digitonin (Dig) or 0.5% dodecylmaltoside (DDM) and the soluble proteins were separated on a 6-16% BN gel and detected by immunoblot. These results show that PNPASE assembles identically in yeast and mammalian mitochondria into a homo-oligomeric complex, a trimer or a "dimer of trimers" (Symmons et al. (2002) Trends Biochem Sci 27:11-18) and indicate that PNPASE may function similarly in yeast and mammalian mitochondria.

Figure 2A:
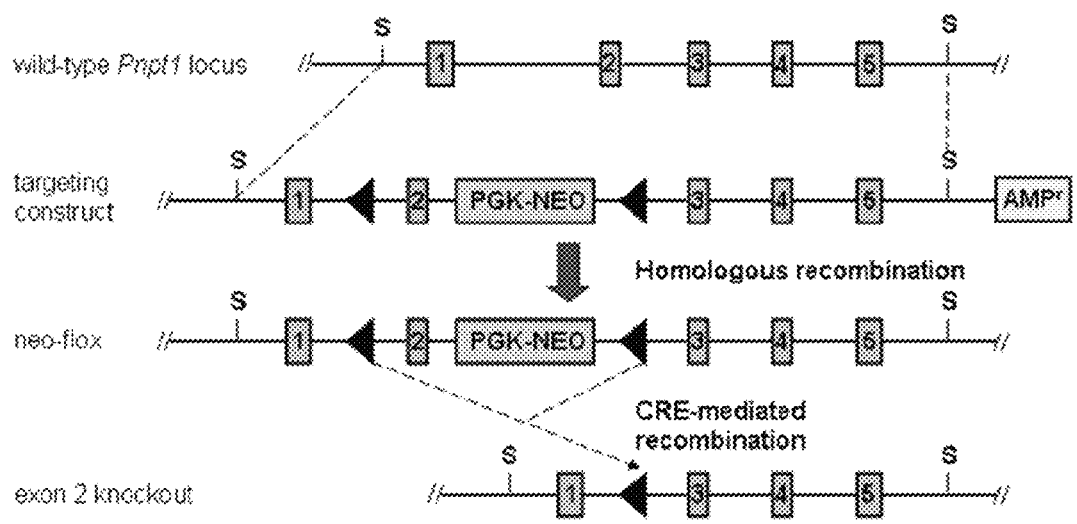
FIGS. 2A-2C schematically show the recombinant strategy for disrupting the Pnpt1 gene.
Figure 2B:
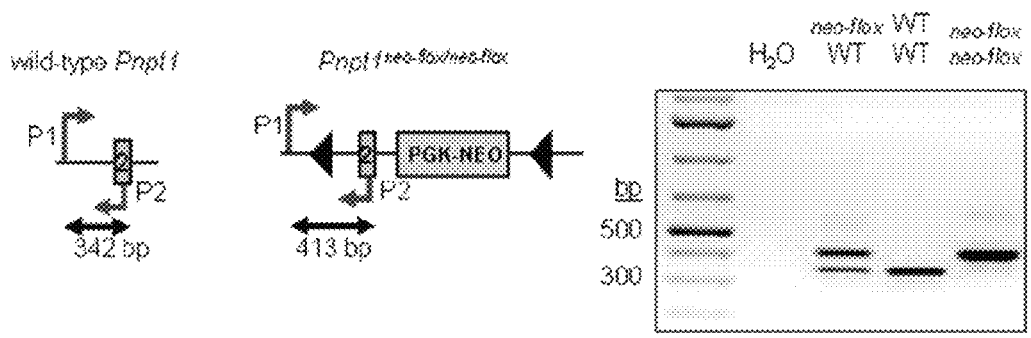
Figure 2C:
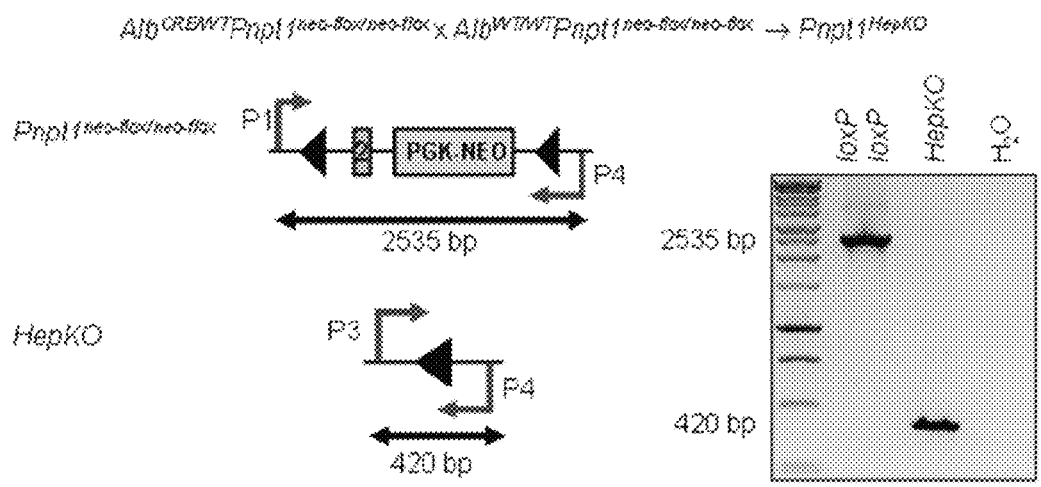
Figure 3A:
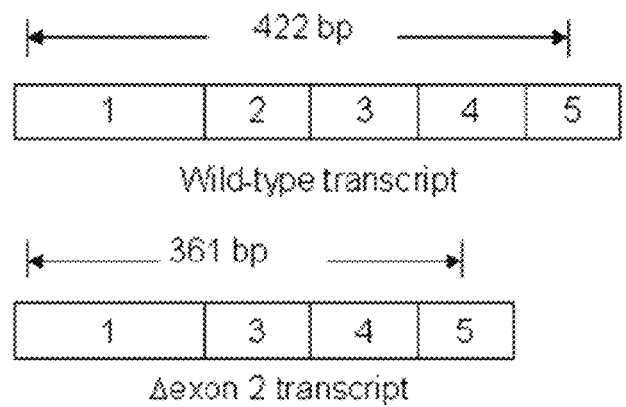
Figure 3B:
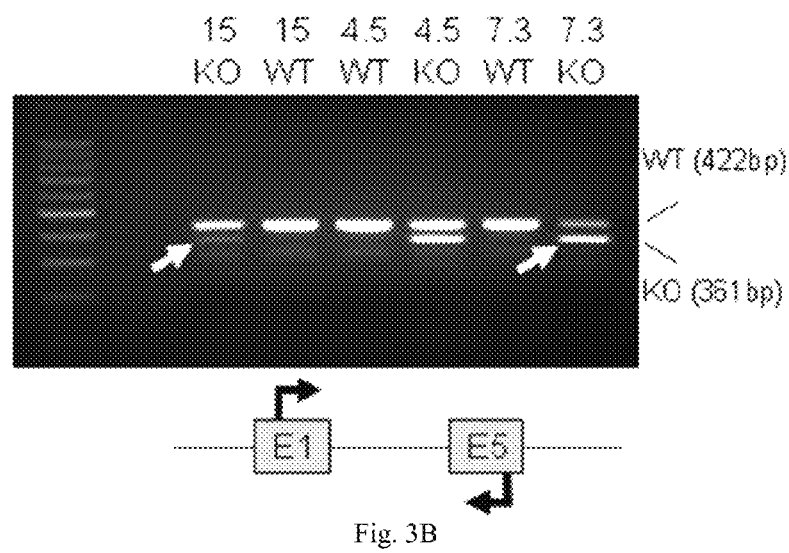
Figure 3C:
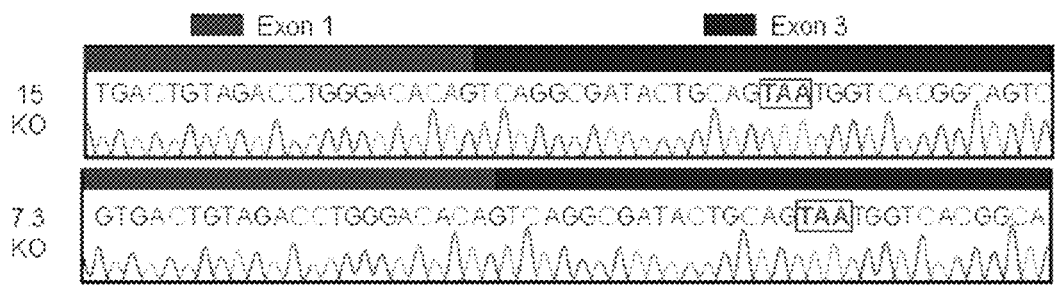
Figure 3D:
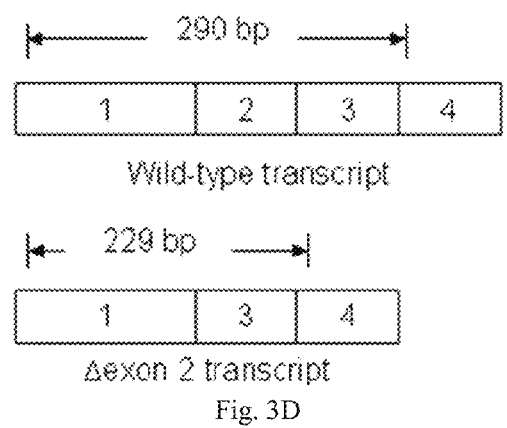

PNPT1 Knockout Cells Show Altered Mitochondrial Morphology and Impaired Respiration Several approaches were used to determine the function of PNPASE in mitochondria. First, the gene encoding PNPASE (Pnpt1) was knocked out (KO) in C57BL/6 mice using methods known in the art. FIGS. 2A-2C show the recombinant strategy for disrupting the Pnpt1 gene and FIG. 3A-3E evidence that excision of Pnpt1 exon 2 generates truncated PNPASE in HepKO liver cells and MEFs.

Figure 4E:
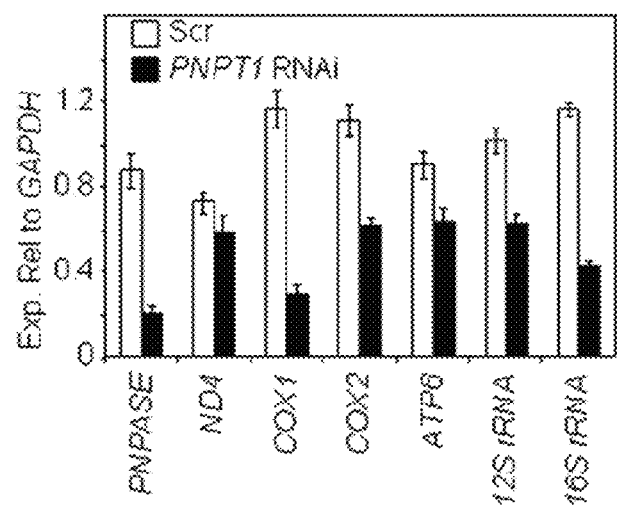

FIGS. 4A-4E evidence that deletion of Pnpt1 in hepatocytes impairs mitochondrial function. As shown in FIG. 4A, (1) homozygous $Pnpt1^{neo-flox}$ mice, in which exon 2 was flanked by loxP recombination sites, were viable and fertile, (2) a complete KO of Pnpt1 exon 2 was generated by crossing $CMV^{CRE}$ expressing mice with $Pnpt1^{WT/neo-flox}$ heterozygotes followed by inter-crossing the $Pnpt1^{WT/KO}$ progeny, and (3) $Pnpt1^{KO/KO}$ mice were embryonic lethal. A liver-specific KO (HepKO) of Pnpt1 was generated by the cross $Alb^{CRE/WT}/Pnpt1^{neo-flox/neo-flox} \times Alb^{WT/WT}/Pnpt1^{neo-flox/neo-flox}$, which produced fertile progeny at the expected frequency. FIG. 4B shows hepatocyte-specific Pnpt1 KO (HepKO) expression in 4-week old mice. Quantitative real-time PCR (QPCR) from HepKO liver showed reduced Pnpt1 transcripts containing targeted exon 2 compared with those containing untargeted exon 28. PNPASE protein expression was also markedly reduced in HepKO liver compared with sex-matched littermate WT liver. FIG. 4C shows that HepKO mitochondria have altered cristae. The ultrastructure of HepKO liver mitochondria was investigated by transmission electron microscopy (TEM). Rather than displaying ordered, linear cristae with convolutions as in WT mitochondria, the HepKO mitochondria showed disordered circular and smooth IM cristae, similar to mitochondria that are impaired for OXPHOS (Mandel et al. (2001) Hepatology 34:776-784) and to Pnpt1 RNAi mammalian cell lines (Chen et al. (2006) Mol Cell Biol 26:8475-8487). Thus, reduced PNPASE may cause a decrease in ATP production prompted the evaluation of $O_2$ consumption from HepKO liver mitochondria. FIG. 4D shows decreased respiration in isolated HepKO mitochondria. Specifically, oxygen consumption (nmol/min/mg protein) for ETC complexes IV and II+III+IV was measured using an $O_2$ electrode, mitochondrial mass was determined by citrate synthase (CS) activity using a spectrophotometer, and respiratory activities were normalized to CS activity. These oxygen electrode studies showed about a 1.5-2 fold decrease in the activity of Complex IV and Complexes II+III+IV when normalized to citrate synthase activity in HepKO compared to WT mitochondria.

Combined, these data establish an in vivo role for PNPASE in mitochondrial morphogenesis and respiration.

PNPASE is Required for the Processing of Mitochondrial RNA Transcripts

Figure 5A:
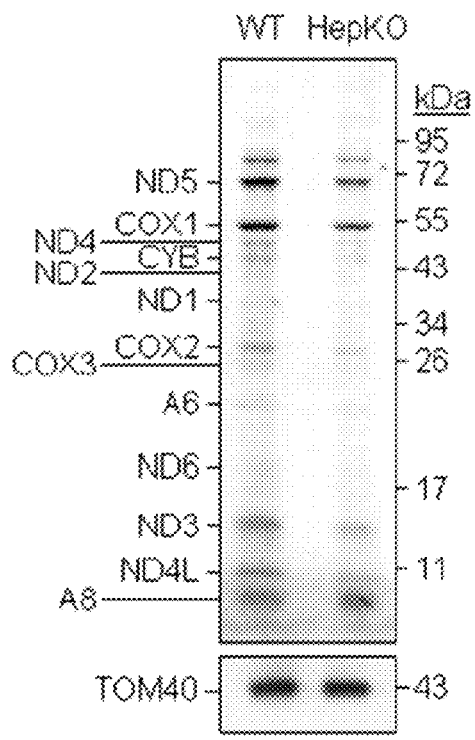
FIGS. 5A-5D show that HepKO liver mitochondria do not efficiently process mtRNA precursors.

The data showing decreased respiration in HepKO mitochondria indicates a reduction in functional ETC complexes. Therefore, RNA processing and translation were examined in cells with decreased PNPASE. HEK293 cells with >75% reduced PNPASE expression were generated by RNAi, followed by mitochondrial RNA (mtRNA) transcript quantification using QPCR normalized to cytosolic GAPDH RNA. FIG. 4E shows decreased mature mtRNAs in HEK293 cells with RNAi to PNPT1. All mtRNAs tested were reduced in Pnpt1 RNAi cells compared to WT cells. Transcripts were quantified relative to cytosolic GAPDH expression by QPCR from HEK293 cells 7d post-infection (nadir) with scramble (Scr) or PNPT1 RNAi retroviral constructs. Proteins translated from mtRNAs were decreased in HEK293 Pnpt1 RNAi cells (data not shown) and HepKO liver cells (FIG. 5A). Thus, a decrease in functional ETC complexes is likely responsible for the decreased respiration.

Figure 5B:
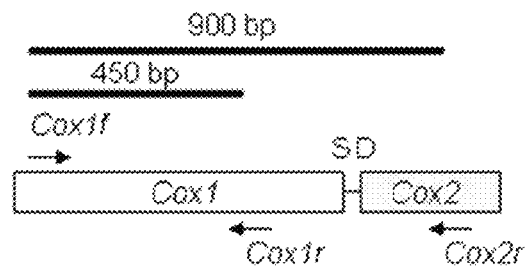
Figure 5C:
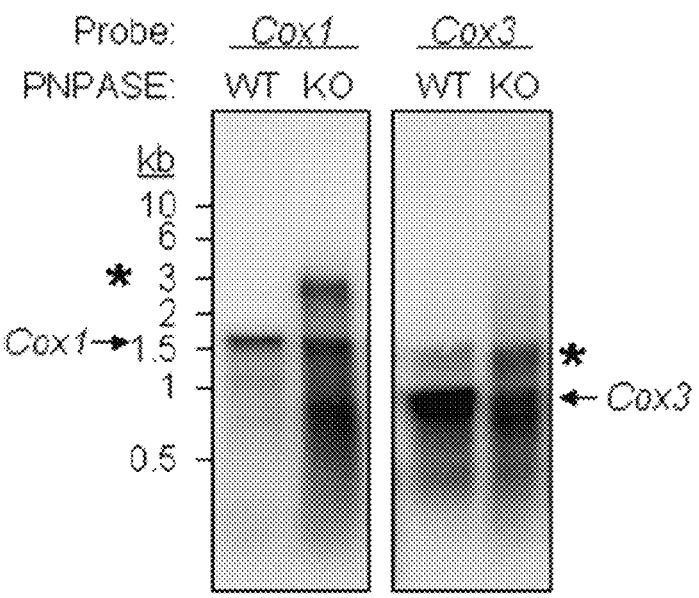
Figure 5D:
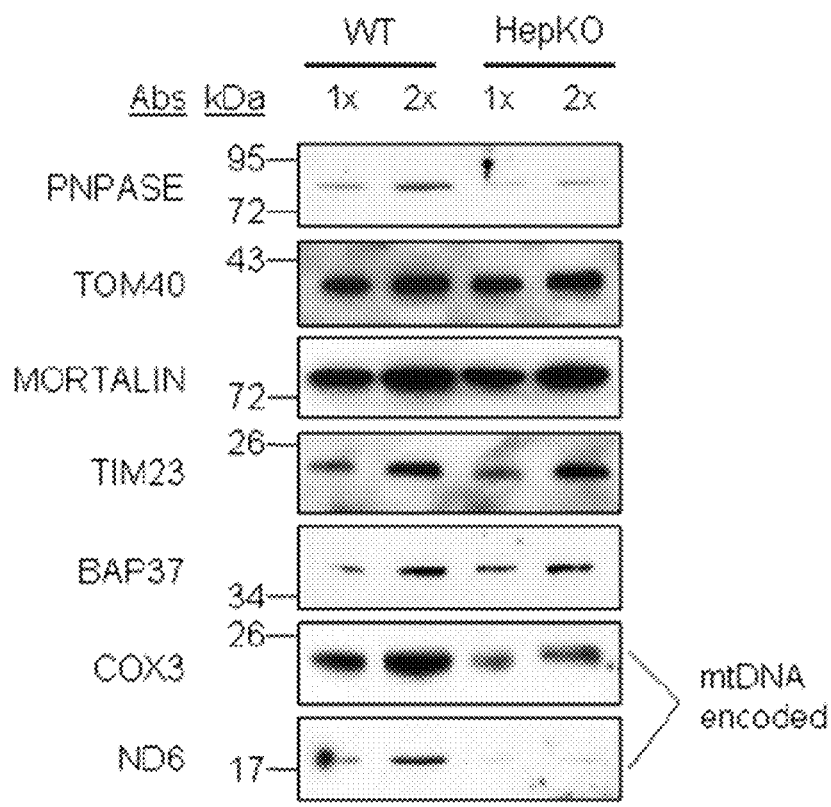
Figure 6A:
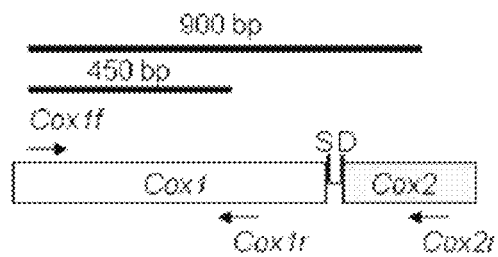
FIG. 6A-6B show mtRNA processing is impaired in PNPASE KO MEFs.
Figure 6A:
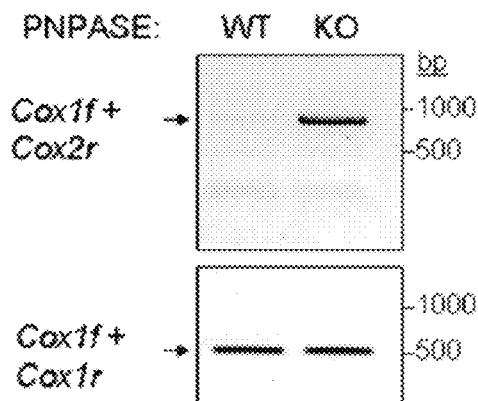
Figure 6B:
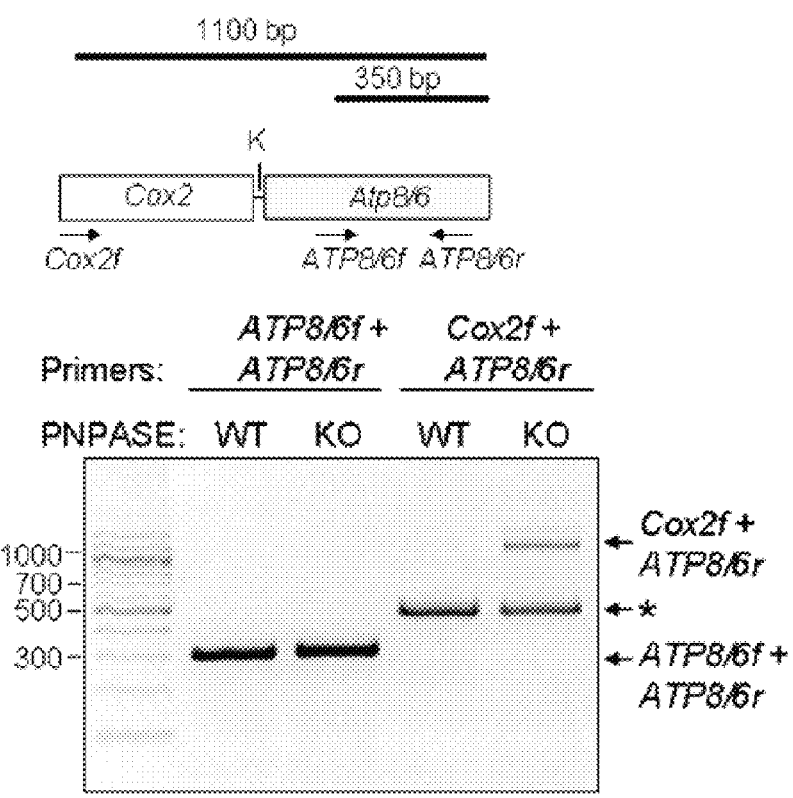

The processing of polycistronic mtRNAs was investigated because reduced PNPASE could cause an accumulation of large precursor transcripts, resulting in reduced ETC proteins. Transcript processing requires RNase P excision of the tRNAs between ETC gene coding regions. RNA was isolated from WT and HepKO liver mitochondria followed by DNase I treatment to remove contaminating DNA. RT-PCR was performed using primers designed to test processing between adjacent Cox1 and Cox2 transcripts that are separated by $tRNA^{ser}$ and $tRNA^{asp}$. As schematically shown in FIG. 5B, the primer set Cox1f and Cox1r generates a 450-bp fragment, whereas the primer pair Cox1f and Cox2r generates a 900-bp fragment when $tRNA^{ser}$ and $tRNA^{asp}$ are not excised from large precursor transcripts. The sequences were separated on a 1.5% agarose gel. A 900-bp fragment was detected from HepKO but not from WT liver mitochondria. Similar results were obtained using the same primers in PNPASE KO mouse embryonic fibroblasts (MEFs) (FIGS. 3A-3E, 6A). To query RNA processing at a second site, primers were generated for adjacent Cox2 and Atp8/6 loci, separated by $tRNA^{lys}$. Again, polycistronic transcripts accumulated in the PNPASE KO MEFs (FIG. 6B). The sizes of Cox1 and Cox3 transcripts were investigated using specific probes and Northern blot. As shown in FIG. 5C, in addition to the mature Cox1 and Cox3 transcripts, a range of larger precursor transcripts was seen in HepKO liver cells. Also, the mature 0.9-kb Cox3 transcript was more abundant in WT than HepKO liver. FIG. 5D is a blot showing the steady-state expression of nuclear (TOM40, MORTALIN, TIM23, and BAP37) and mitochondrial (COX3, and DN6) encoded proteins in WT and HepKO liver mitochondria. In HepKO liver mitochondria, the steady-state abundance of PNPASE was decreased by about 2-fold compared to the WT, similar to about a 2-fold decrease for COX3 and ND6 proteins. Equivalent nuclear-encoded protein expression shows that HepKO reduced mitochondria-encoded protein expression was not due to differing mitochondrial content between WT and HepKO liver cells. Controls TOM40, MORTALIN, TIM23, and BAP37 showed that the amount of nuclear-encoded mitochondrial proteins, and therefore the mitochondrial mass, was similar between HepKO and sex-matched WT littermate liver cells. Thus, the processing of polycistronic mtRNAs was impaired in mitochondria with reduced PNPASE, resulting in fewer mature mtRNAs and reduced ETC complexes.

Figure 7A:
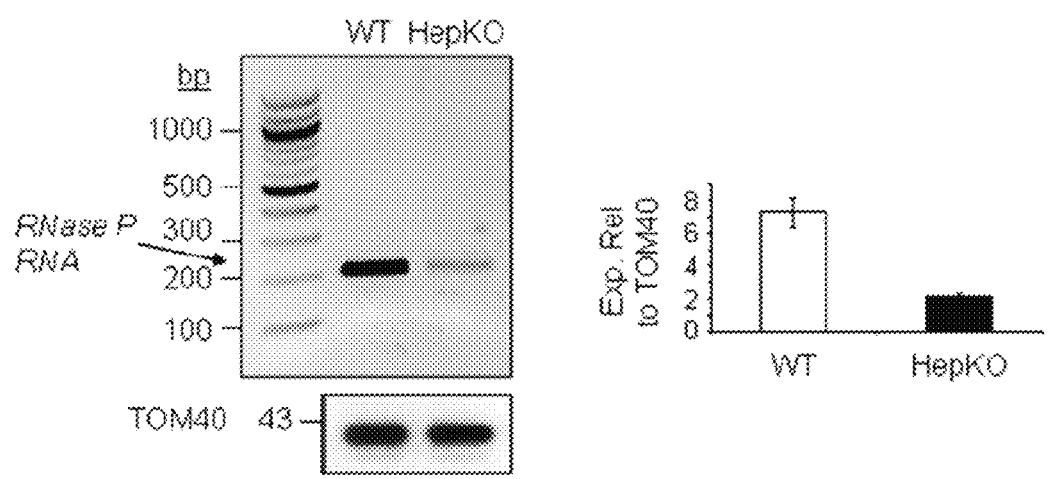
FIGS. 7A-7D show that RNase P RNA binds to PNPASE and may function in PNPASE-dependent tRNA processing.

RNase P RNA Binds to Pnpase and May Function in PNPASE-Dependent mtRNA Processing The abundance of RNase P RNA in HepKO liver mitochondria was determined by RT-PCR and QPCR. FIG. 7A (left) is a gel showing RNase P RNA isolated from WT and HepKO liver mitochondria following nuclease treatment. RT-PCR was performed with primers that amplify nuclear-encoded RNase P RNA (212-bp). FIG. 7A (right) is a gel showing the QPCR analysis of RNase P RNA expression relative to TOM40 protein in isolated mitochondria. Reproducibly, RNase P RNA was decreased by about 75% in HepKO versus WT liver mitochondria. Thus, PNPASE may help import and/or stabilize RNase P RNA.

Figure 7B:
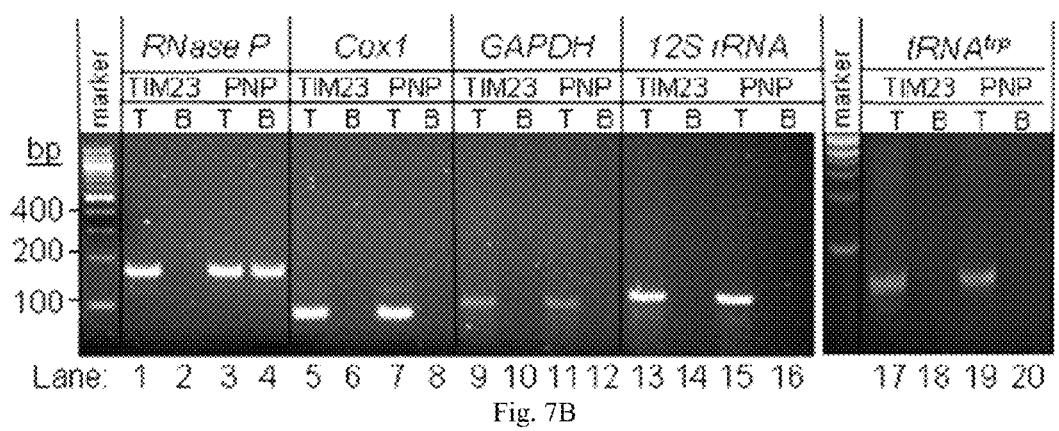

Therefore, whether RNase P RNA directly binds PNPASE in HEK293 cells stably expressing dual-tagged PNPASE-HisPC was determined. Isolated mitochondria were treated with nuclease and tagged PNPASE was purified. RNase P RNA was amplified by RT-PCR and co-purified with PNPASE (FIG. 7B, lane 4). Importantly, control IM-localized TIM23-HisPC in stably-expressing HEK293 cells did not bind RNase P RNA (FIG. 7B, lane 2). PNPASE also did not adventitiously bind RNA because the RNA transcripts for Cox1, GAPDH, mitochondrial 12S rRNA and mitochondrial $tRNA^{trp}$ were not bound to PNPASE (FIG. 7B). Thus, RNase P RNA bound specifically to PNPASE.

Figure 7C:
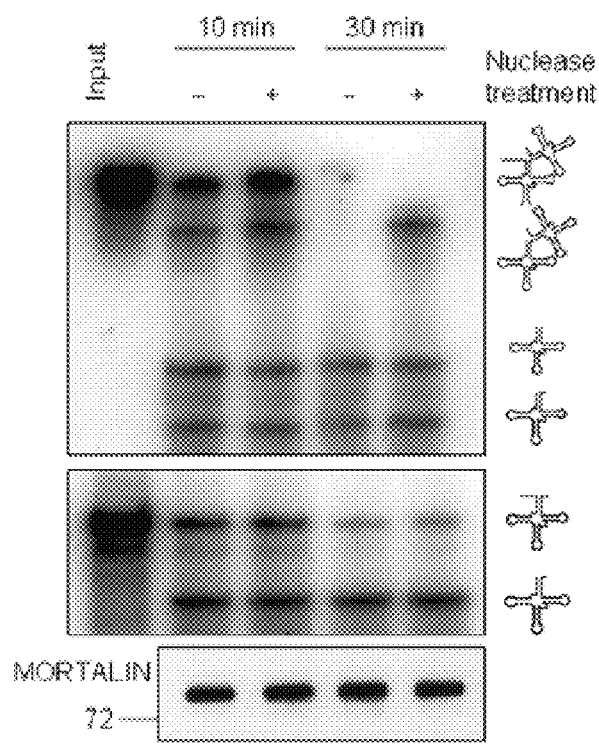
Figure 7D:
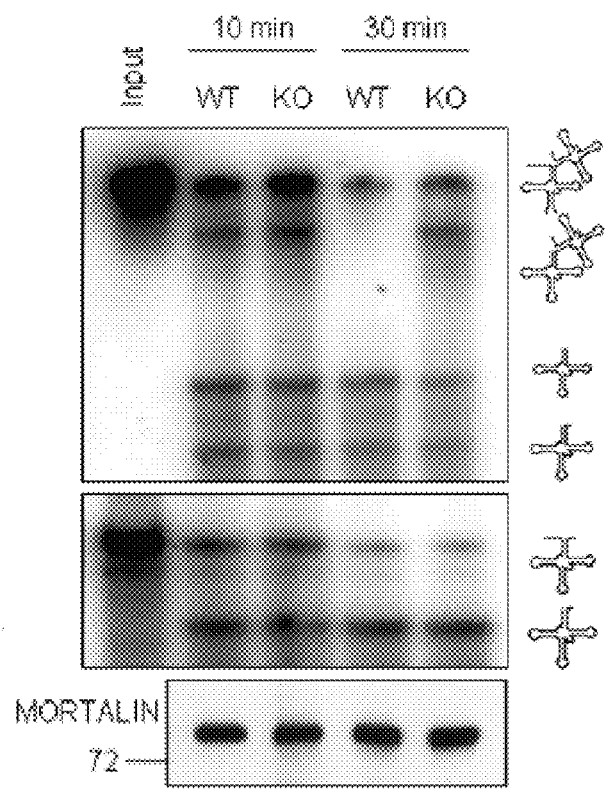

Whether protein-only RNase P can efficiently process paired mitochondrial tRNAs, as must occur in vivo, was examined using methods known in the art. See e.g. Holzmann et al. (2008) Cell 135:462-474. FIG. 7C shows the processing of single tRNA or paired tRNA precursors by mitoplast extract pre-treated with nuclease or without the treatment. A MORTALIN immunoblot shows equivalent mitoplast extract in each assay. Specifically, the mitoplast extract (10 µg) was treated with nuclease (+), as indicated, and then inactivated with EDTA and EGTA. The nuclease-treated or untreated extract was incubated with abutted tRNAs (tRNA$^{His}$tRNA$^{Ser}$) or a single tRNA (tRNA$^{Lys}$) at 25° C. for 10 or 30 min. RNA was separated on an urea-acrylamide gel and detected by autoradiography. By contrast, nuclease-treated lysates were impaired in cleaving the two abutting tRNAs into individual tRNAs, thereby indicating that an additional nucleic acid component is required for efficient processing. Interestingly, mitoplast lysates from HepKO liver showed the same defect on abutting tRNA maturation as the nuclease-treated WT mitoplast lysates (FIG. 7D).

Figure 8A:
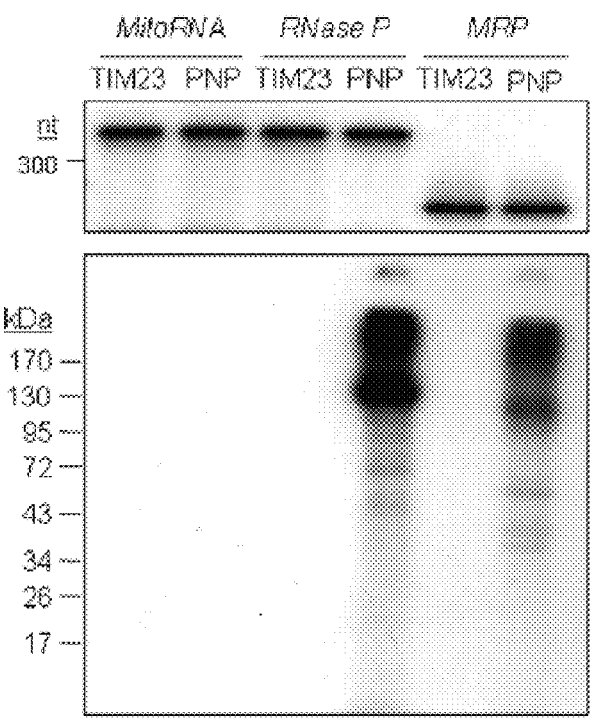
FIGS. 8A-8B show that PNPASE binds RNase P and MRP RNAs and affects the processing of linked tRNAs in vivo.
Figure 8B:
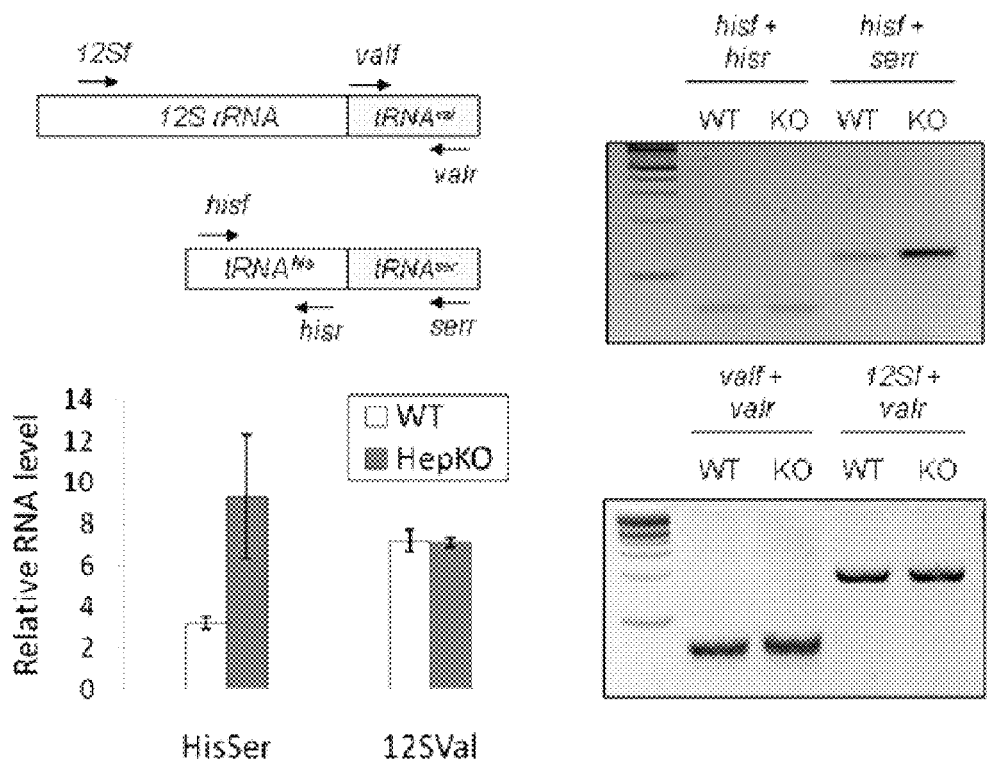
Figure 9A:
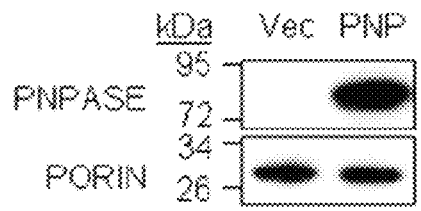
FIGS. 9A-9D show that added human PNPASE does not alter yeast physiology.
Figure 9B:
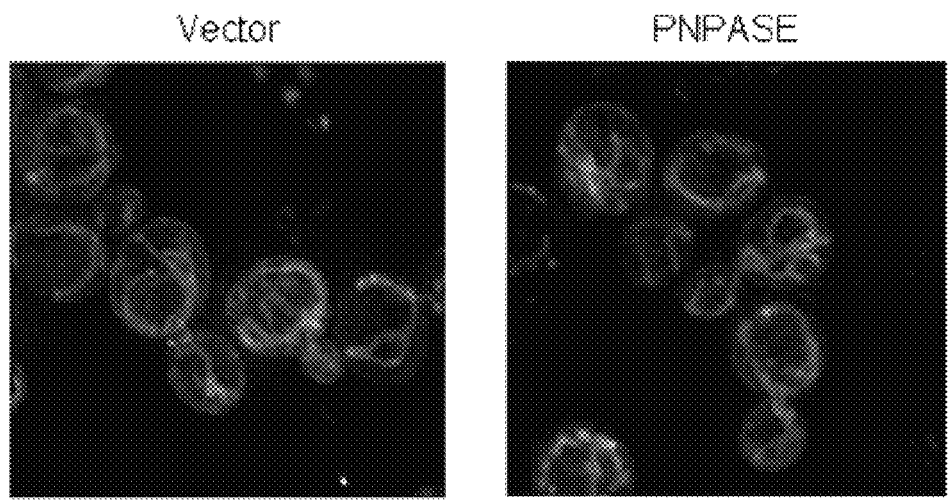
Figures 9C, 9D:
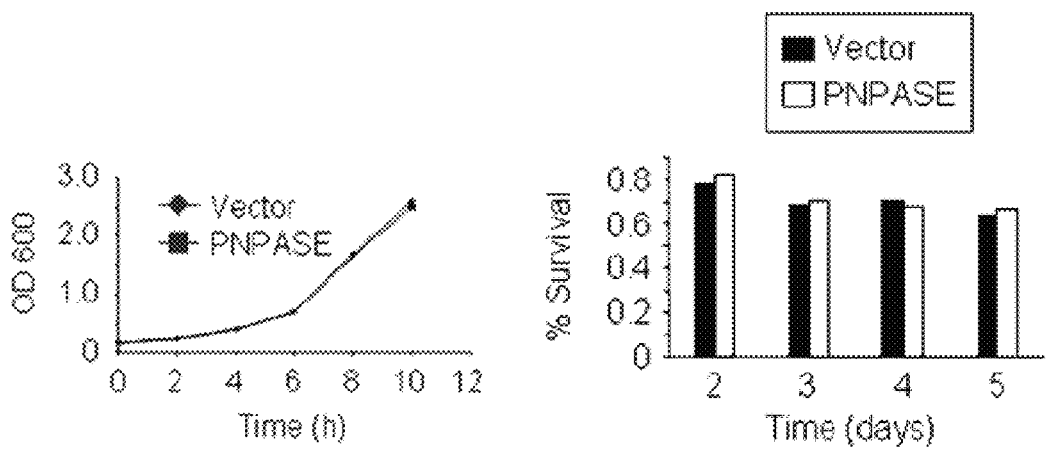

FIG. 8A are gels showing that PNPASE-HisPC, but not TIM23-HisPC, bound in vitro transcribed RNase P and MRP RNAs during import, but not control mitochondrial RNA, in cross-linking IP assays. Isolated mitochondria from HEK293 cells stably expressing IMS-localized PNPASE-HisPC or TIM23-HisPC (control) dual-tagged proteins were incubated with [$^{32}$P]-CTP labeled RNase P, MRP, or a control mitochondrial RNA transcript (MitoRNA, 340 nucleotides that includes tRNA$^{trp}$), followed by UV cross linking, tag-immunoprecipitation, separation by SDS-PAGE, and autoradiography. FIG. 8B are gels showing that the in vivo processing and separation of an endogenous paired tRNA$^{his}$tRNA$^{ser}$ substrate was inhibited in HepKO compared to WT liver mitochondria, whereas a linked 12s rRNA-tRNA$^{val}$ substrate was processed equivalently. Contaminating DNA was removed by DNase I treatment. RT-PCR was performed using primer pairs as shown in the schematic diagrams to detect either the pre-processed linked or processed separated transcripts. Quantification of the RT-PCR results (precursor over single tRNA ratios are plotted as relative RNA abundances) is shown in lower left of the figure.

These results indicate that protein-only and RNase P RNA-containing RNase P complexes coexist in mitochondria and that PNPASE-dependent RNase P RNA provides efficient tRNA processing.

Figure 10A:
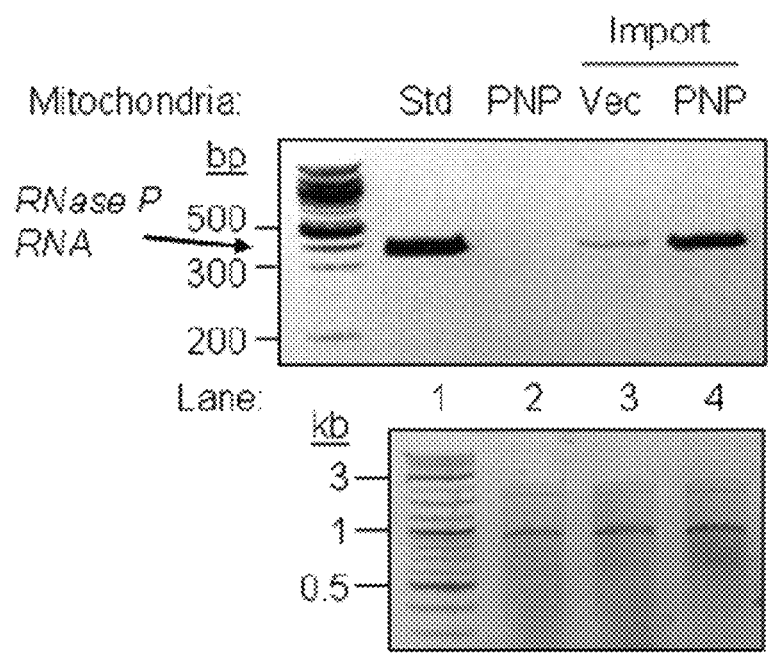
Figure 10B:
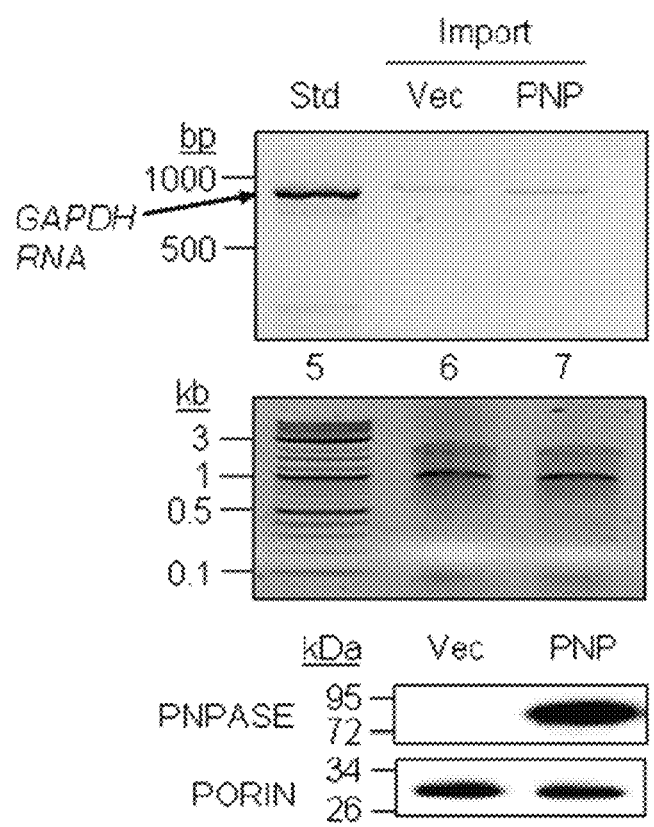

PNPASE Augments the Import of RNase P, 5S rRNA, and MRP RNAs into Yeast Mitochondria As human PNPASE is assembled into similar complexes when expressed in yeast and as in mammalian mitochondria (FIGS. 1A-1D), yeast may be used as a model for studying the import of nuclear-encoded RNAs (Chen et al. (2006) Mol Cell Biol 26:8475-8487). FIGS. 9A-9D show that added human PNPASE did not alter yeast mitochondrial morphology, rate of proliferation, or extent of cell death. Mitochondria isolated from WT yeast or yeast expressing human PNPASE were incubated with in vitro transcribed human RNase P RNA in import buffer (see RNA Import Assay above). The reaction was treated with nuclease to remove non-imported RNA followed by RNA isolation and RT-PCR. FIG. 10A shows that RNase P RNA abundance was increased in mitochondria containing PNPASE compared to WT mitochondria. This RNA increase was specific for certain RNAs because, as shown in FIG. 10B, cytosolic GAPDH RNA was not increased in the same mitochondria. Osmotic shock was used to identify the location of the imported RNase P RNA (Koehler et al. (1998) Science 279:369-373). Mitochondria were incubated in hypotonic buffer to rupture the outer membrane and the mitoplasts (P, pellet fraction that contains the matrix and IM) and the supernatant (S, contains the soluble IMS contents) were separated by centrifugation (FIG. 10C). RNase P RNA was detected by RT-PCR and was localized in the mitochondrial matrix. Detergent exposed the matrix to verify that the nuclease degraded the RNase P RNA. To confirm that osmotic shock did not disrupt the IM, antibodies against cytochrome b$_2$ (cyt b$_2$; IMS) and α-ketoglutarate dehydrogenase (KDH; matrix) showed that cyt b$_2$ was sensitive to protease in the IMS, but KDH was resistant to protease until the IM was lysed with Triton X-100. Thus, RNase P RNA import was augmented, RNase P RNA was stabilized, or both, in the yeast mitochondrial matrix when exogenous PNPASE was present in the IMS.

To confirm the RT-PCR results and assay other imported RNAs, in vitro RNA import assays with yeast mitochondria and radiolabeled human RNAs were performed (FIG. 10D). Two different RNA volumes were used and the imported RNA was isolated and separated on a urea-acrylamide gel followed by autoradiography. FIG. 10D shows that RNase P, 5S rRNA, and MRP RNAs augmented import or stability in mitochondria expressing PNPASE relative to control mitochondria. Again, this increase was RNA-type specific as PNPASE did not augment GAPDH RNA levels. FIG. 10E shows that when the mitochondrial membrane potential was dissipated, the RNase P RNA level was not increased in this assay system.

PNPASE Mutations that Inactivate RNA Processing Do Not Affect RNA Import or Stability To determine whether the RNA import or stabilization activity of PNPASE was separable from its RNA processing activities, RNase P RNA import was studied when different PNPASE mutants were expressed in yeast mitochondria (FIG. 11A). The point mutants generated and tested were based on prior studies (Portnoy et al. (2008) RNA 14: 297-309). Mutants D135G and S484A lacked poly-A polymerase and RNA degradation activities in vitro. Mutant D544G and double mutant R445E/R446E showed enhanced in vitro poly-A polymerase activity but compromised degradation activity. Of the four mutants, PNPASE S484A and R445E/R446E supported the import or stabilization of RNase P RNA, whereas mutants D135G and D544G were defective in this function (FIG. 11A). Based on the prior studies of others, it was expected that mutant D135G would fail to form a trimeric complex from prior studies (Portnoy et al. (2008) RNA 14: 297-309). Surprisingly, however, the abundance of WT and the four mutant PNPASE proteins were similar between yeast strains and all of the PNPASE proteins assembled into about 240 kDa complexes without impairment (FIG. 11A, lower panel). These results evidence that the mitochondrial RNA import or stabilization function of PNPASE is separable from its poly-A polymerase or exoribonuclease activities.

To determine whether PNPASE augmented either RNA import or stabilization in mitochondria, the enzymatic properties of the WT and S484A mutant protein were examined with respect to RNA turnover in vitro and in isolated yeast mitochondria. For in vitro studies, WT and S484A PNPASE were immunoprecipitated from yeast mitochondria and tested in an in vitro degradation assay with radiolabeled RNase P RNA (FIG. 11B). Consistent with prior results, WT PNPASE degraded the RNase P RNA, but the S484A mutant was impaired. As shown in FIG. 11C, radiolabeled RNase P RNA was imported into mitochondria. Following in vitro import of radiolabeled RNase P RNA and nuclease treatment to remove non-imported RNA, mitochondria were incubated for up to 90 min at 25° C. and aliquots removed at the indicated time points. The RNA was then resolved by urea-acrylamide gel electrophoresis. The internalized RNase P RNA was separated on a urea-acyrlamide gel and quantified during this time course using a phosphorimager. The rate of degradation of RNase P RNA was similar for degradation competent WT and incompetent mutant PNPASE proteins, supporting a role for PNPASE in augmenting the import of specific RNAs into the mitochondrial matrix. This result further supports PNPASE localizing to the IMS because a greater amount of WT PNPASE imported into the matrix could cause a relative increase in the rate of turnover of matrix localized RNAse P RNA.

A Predicted Stem-Loop RNA Structure Mediates PNPASE-Dependent RNA Import

Figure 12A:
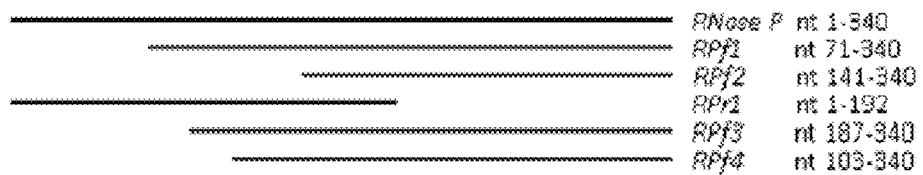
FIGS. 12A-12G show that a stem-loop structure mediates PNPASE-dependent RNA import.
Figure 12B:
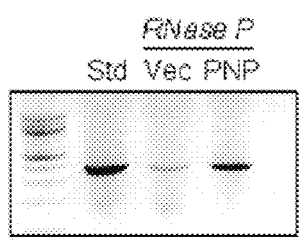
Figure 12C:
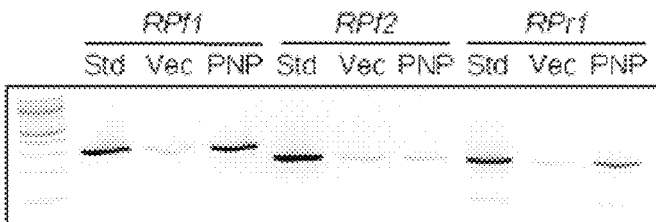
Figure 12D:
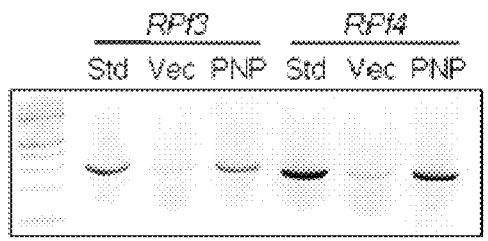
Figure 12E:
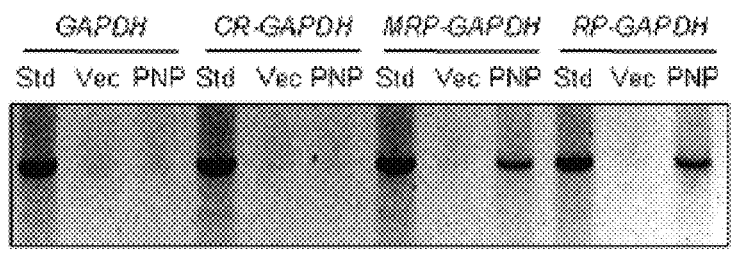
Figure 12F:
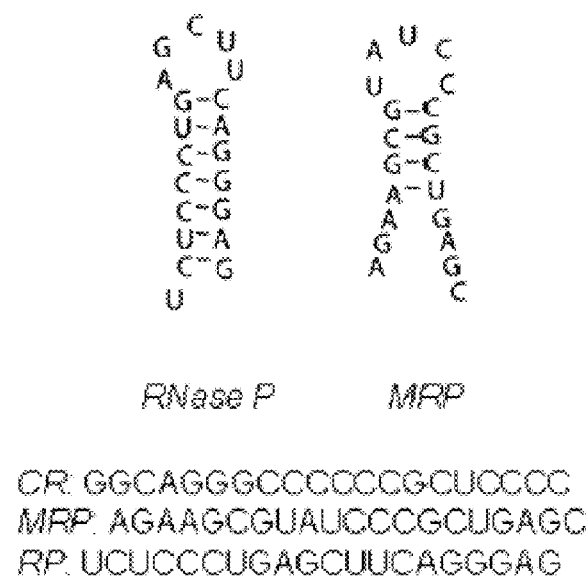

To determine whether PNPASE plays a direct role in RNA import, a systematic search was used to identify PNPASE-dependent RNA import sequences. Primers were designed to generate distinct segments of the 340 nucleotide (nt) RNase P RNA full length sequence. RPf1 lacked the 5' 70 nt, RPf2 lacked the 5' 140 nt, and RPr1 lacked the 3' 148 nt of WT PNPT1 (FIG. 12A). Import assays were performed using full length or truncated in vitro transcribed RNase P RNAs (FIGS. 12B, 12C). Augmented RPf1 and RPr1 import into yeast mitochondria depended upon PNPASE, as did the full length RNase P RNA. In striking contrast, RPf2 was not efficiently imported into yeast mitochondria, implicating the sequence between nt 71 and 140 in PNPASE-augmented RNA import. To further refine this import signal, RNA sequences lacking the 5' 86 (RPf3) or 102 (RPf4) nts were generated (FIG. 12A). Augmented RPf3 and RPf4 import into yeast mitochondria was PNPASE-dependent (FIG. 12D), further implicating an import signal between nt 103 and 140. The most likely, predicted secondary structure of RNase P RNA in this region was a 20 nt stem-loop (FIG. 12F). Interestingly, a similarly-predicted stem-loop structure was also identified in MRP RNA.

Figure 12G:
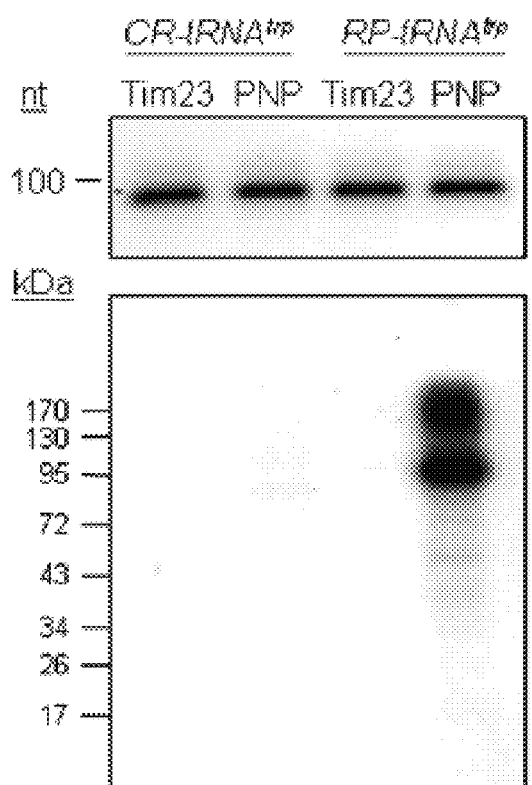
Figure 13A:
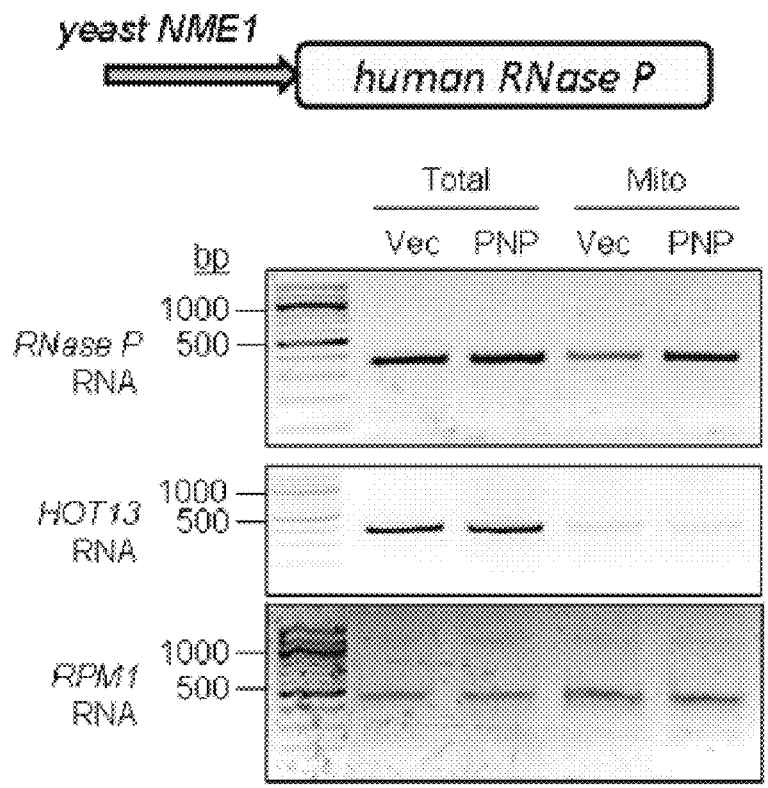
FIGS. 13A-13D show that PNPASE augments RNA import into yeast and mammalian mitochondria in vitro.
Figure 13B:
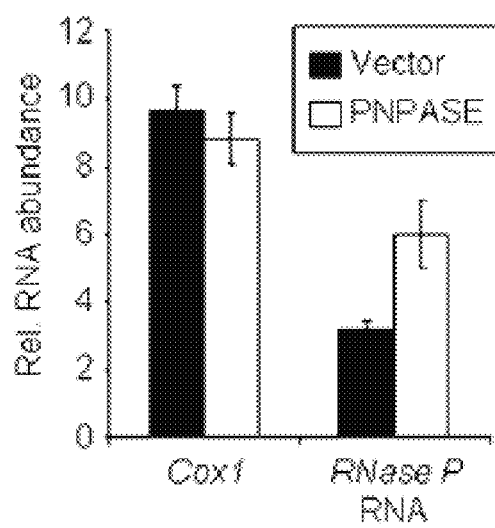
Figure 13C:
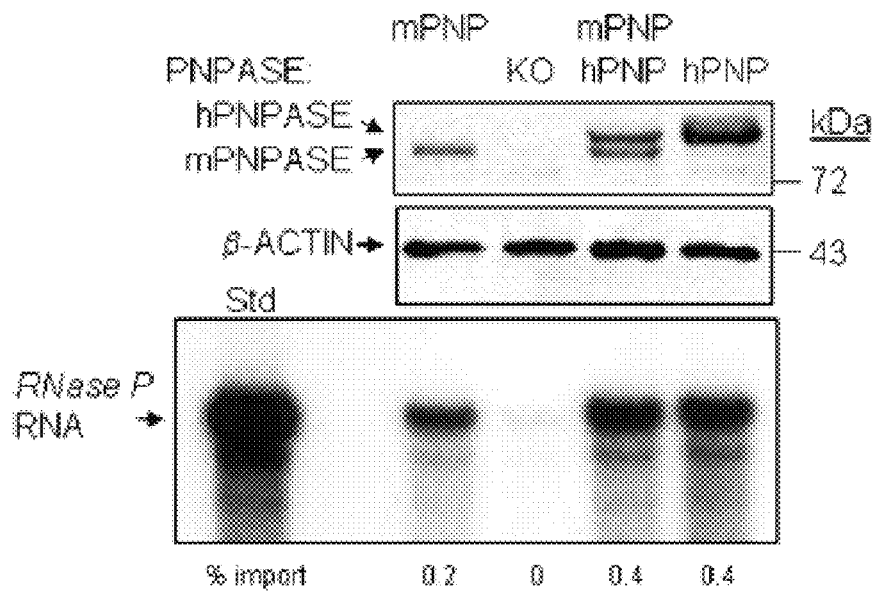
Figure 13D:
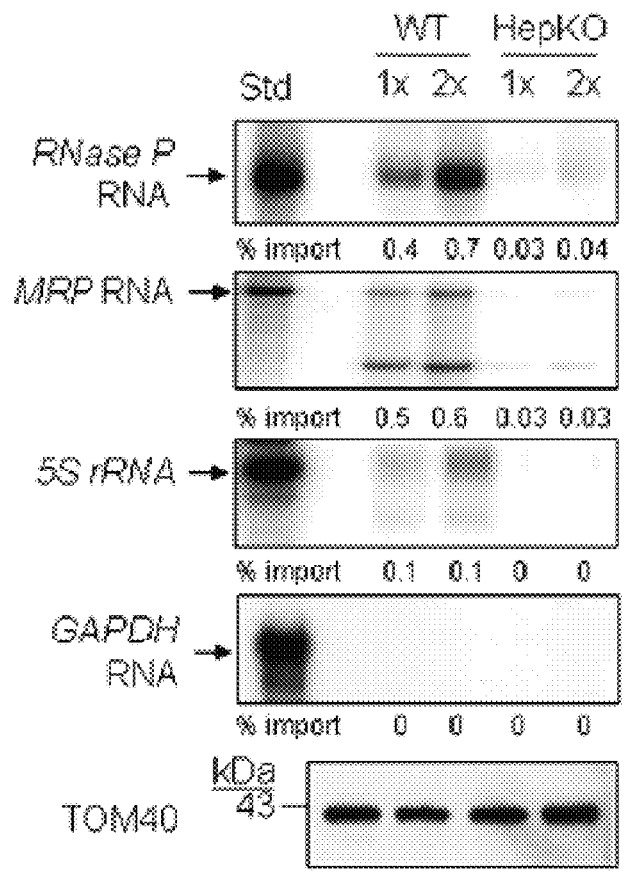
Figure 14A:
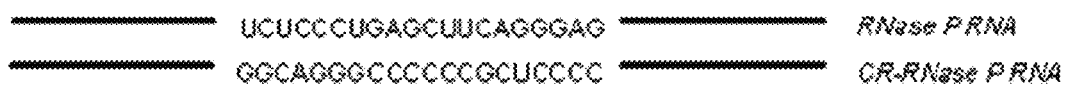
FIGS. 14A-14E show that the stem-loop of RNase P RNA is involved in in vivo import into mitochondria and in vitro transcribed MRP RNA undergoes a PNPASE-dependent import and processing in MEF mitochondria.
Figure 14B:
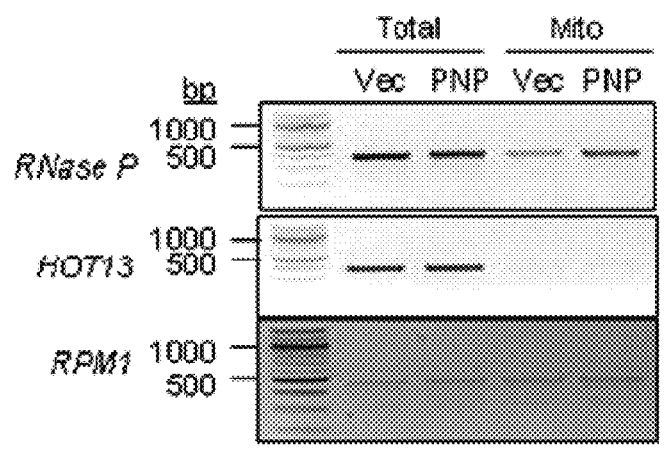
Figure 14C:
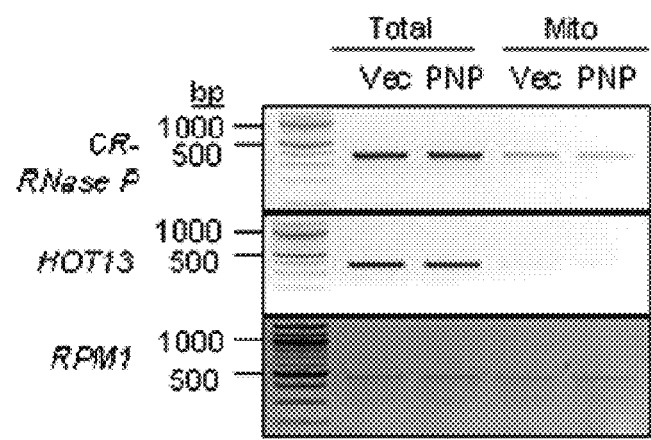
Figure 14D:
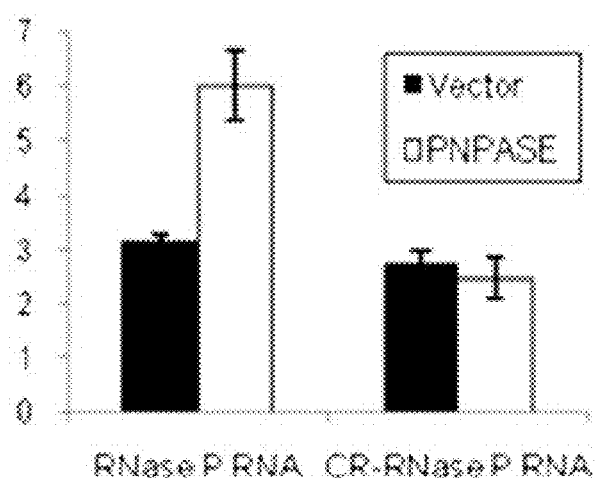
Figure 14E:
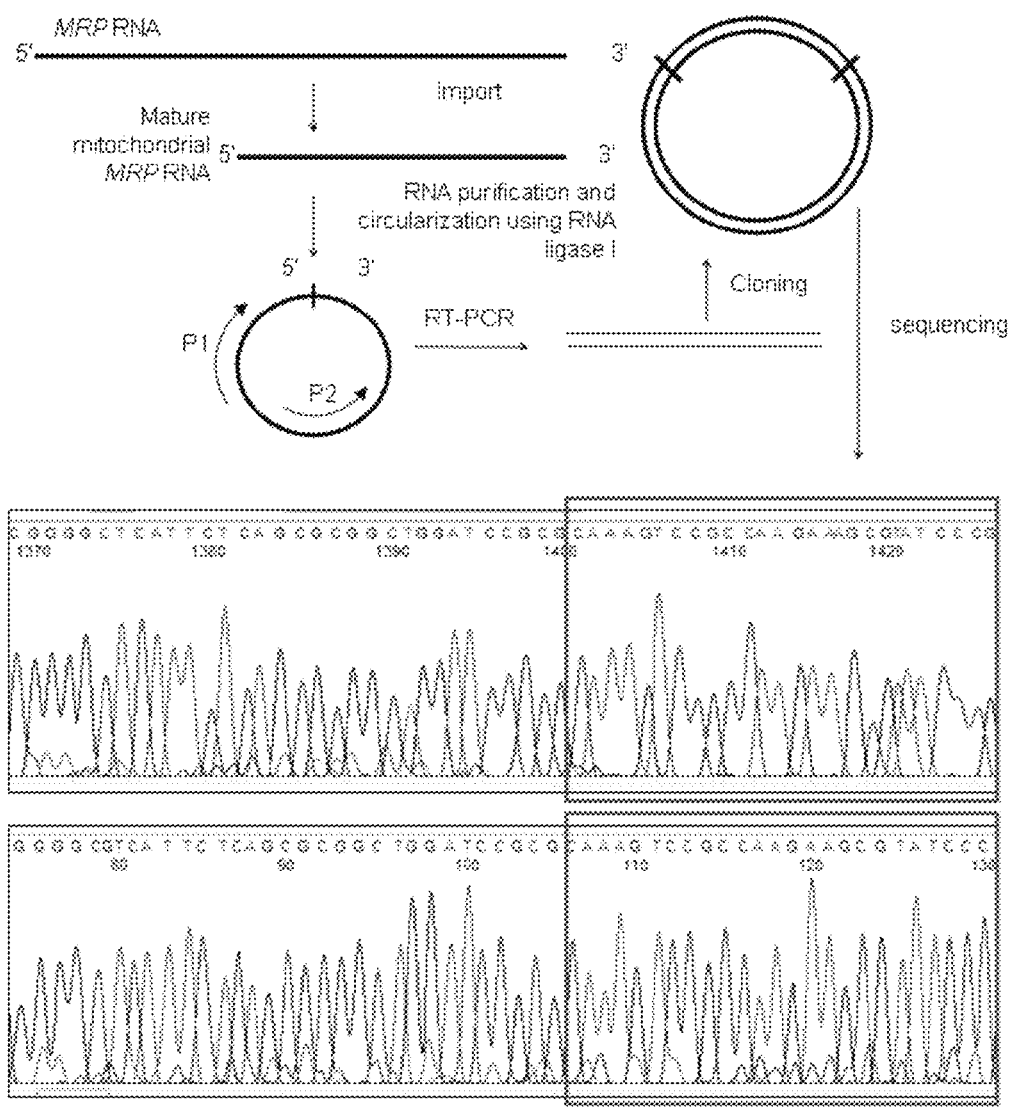

To determine whether one or both stem-loop structures could mediate mitochondrial targeting of non-imported GAPDH RNA, each 20 nt stem-loop sequence was fused to the 5'-terminus of the GAPDH RNA, which is not imported (FIGS. 10D and 13D). Strikingly, the RNase P and MRP stem-loop structures enabled the PNPASE-dependent import of GAPDH RNA into yeast mitochondria (FIG. 12E). By contrast, a control random 20 nt sequence could not mediate this import. Human mitochondrial tRNA$^{trp}$ with the RNase P RNA step-loop structure, but not tRNA$^{trp}$ itself, was imported into isolated mouse liver mitochondria, with the tRNA$^{trp}$-PNPASE interaction captured using UV-cross linking (FIG. 12G). These results strongly implicate the structural specificity of mitochondrial RNA import (FIG. 12F) and the direct involvement of PNPASE in this process.

PNPASE Augments RNA Import into Yeast Mitochondria In Vivo

To explore in vivo RNA import into mitochondria, a construct was generated in which the human RNase P RNA was expressed from the yeast NME1 promoter. See FIG. 13A (upper). When expressed in control yeast, RNase P RNA localized to mitochondria. This is consistent with nuclear-encoded RNA import by a PNPASE-independent mechanism since yeast normally lack PNPASE. By contrast, as shown in FIGS. 13A (lower) and FIG. 13B, RNase P RNA import increased by about 2-fold in mitochondria from yeast expressing PNPASE compared with control cells. Importantly, a RNA similar in size to RNase P RNA (340 nt), HOT13, that is translated in the cytosol and imported as a protein into mitochondria, was not localized to mitochondria. Also, mitochondrial-encoded RPM1, which codes for the yeast homologue of RNase P RNA, was sequestered in the mitochondrion at a level equivalent to control yeast mitochondria, as expected. These data indicate that PNPASE augments the import of RNase P RNA into yeast mitochondria in vivo.

Finally, as shown in FIGS. 14A-14E, replacement of the human RNase P RNA stem-loop sequence with the 20 nt random sequence blocked augmented RNase P RNA import into yeast mitochondria in vivo, thereby confirming the role of the stem-loop in PNPASE-regulated import.

PNPASE Augmented Import of RNase P RNA into Mammalian Mitochondria

To examine PNPASE dependent mitochondrial RNA import in a more physiologically relevant system, WT, PNPASE KO, WT expressing human PNPASE, and PNPASE KO expressing human PNPASE MEFs were developed for import assays. SV40 large T-antigen immortalized MEFs were generated from day 14 Pnpt1$^{neo-flox/neo-flox}$ C57BL/6 embryos by standard methods. MEFs and HEK293 fibroblasts were maintained in growth medium supplemented with 10% fetal bovine serum, 2% L-glutamine, and antibiotics. A retroviral expression construct containing a 3'-flag tagged human PNPT1 cDNA, MSCV-PNPT1-IRES-PURO (Chen et al. (2006) Mol Cell Biol 26: 8475-8487), was generated by standard methods. Retroviral supernatants were produced by transient transfection of the 293T Phoenix packaging cell line, after which MEFs were bulk infected and selected in puromycin. PNPASE abundance in each MEF line was confirmed by immunoblot (FIG. 13C). Radiolabeled RNase P RNA was not imported into mitochondria from the PNPASE KO MEFs, but was imported into mitochondria that contained mouse and/or human PNPASE. The in vitro import of RNase P, MRP, 5S rRNA, and GAPDH RNAs was also tested in liver mitochondria isolated from the HepKO mouse and WT littermates. Again, as shown in FIG. 13D, RNase P, 5S rRNA, and MRP RNAs were imported into mitochondria expressing PNPASE, whereas cytosolic GAPDH RNA was not imported. More than half of the imported MRP RNA was processed into the mature ~130 nt form (FIGS. 13D and 14A-14E). By contrast, however, mitochondrial RNA import was severely compromised in HepKO liver mitochondria.

B. RNA Import Sequence, Mitochondria Localization Sequence, and mtRNA Stem-Loop Modification/Extension The experiments below show that an RNA import sequence (RP import sequence, a 20-ribonucleotide stem-loop sequence from the H1 RNA, the RNA component of the human RNase P enzyme) appended to a non-imported RNA directs the import of the resultant RNA fusion transcript into human mitochondria. The RNA import sequence effectively transports both non-coding RNAs, such as tRNAs, and mRNAs into mitochondria in vitro. In vivo, additional targeting sequence and modification may be required for import of nucleus-encoded RNAs into mitochondria. For mRNAs such as COX2, RP import sequence is sufficient for mitochondrial import in vivo when encoded in the nucleus. For nucleus-encoded tRNAs, in vivo mitochondrial import requires an extended tRNA stem which enables the precursor's escape from the nucleus and 3'-UTR mitochondrial targeting sequence from mRNA of human mitochondrial ribosomal protein S12 (MRPS12) which targets the precursor to the vicinity of mitochondria where the RP stem-loop can function to have the precursor imported into mitochondrial matrix and processed into mature and functional tRNA.

Materials and Methods

Cell Culture, Transfection, and Transduction

Mammalian cell lines were maintained in DMEM growth medium supplemented with 10% fetal bovine serum and 2% L-glutamine. MERRF and MELAS cybrid lines (kindly provided by Dr. Carlos Moraes, University of Miami Miller School of Medicine) were maintained in DMEM growth medium supplemented with 10% fetal bovine serum, 2% L-glutamine, and 0.5 mg/ml uridine. Transient transfections were performed using the Bio-T reagent (Bioland Scientific LLC, Paramount, Calif.). In transfections with COX2 constructs, the calcium phosphate uptake method was used. Retroviral supernatants were produced by transient transfection of the 293T Phoenix packaging cell line (GenHunter Corp., Nashville, Tenn.), after which the cells were bulk infected and selected in puromycin.

Plasmid Construction

To generate mCOX2 and RP-mCOX2 constructs, the mCOX2 cDNA was PCR amplified from mouse mtDNA using the forward primers:

```
                                                                (SEQ ID NO: 16)
5'GAGAAGATCTATGGCCTAACCCATTCCAAC 3'
or (SEQ ID NO: 17)
5'GAGAAGATCTATGTCTCCCTGAGCTTCAGGGAGGATGGCCTAACCCATTCCAAC 3', respectively,
``` and the reverse primer:

```
                                                                (SEQ ID NO: 18)
5'CCGCCGCTCGAGTTAAATTATTGAAGCAGATCAGTTTTCGA 3',
``` and then inserted into the PQsuper expression vector.

To generate hCOX2 and RP-hCOX2 constructs, hCOX2 cDNA was PCR amplified from human mtDNA using the forward primers:

```
                                                                (SEQ ID NO: 19)
5'CGGCCGCACCGGTATGGCACATGCAGCGC 3'
or (SEQ ID NO: 20)
5'CGGCCGCACCGGTATGTCTCCCTGAGCTTCAGGGAGGATGGCACATGCAGCGC 3', respectively,
``` and the reverse primer:

```
                                                                (SEQ ID NO: 21)
      5'CGCGGATCCCTATAGGGTAAATACGGGC 3',
``` and then inserted into the PQCXIP expression vector.

To generate Leu and RPLeu constructs, tRNAUUR Leu with 5' and 3' presequences was PCR amplified from human mtDNA using the forward primers:

```
                                                                (SEQ ID NO: 22)
5'CGGCCGCACCGGTATGGAGAAATAAGGCCTACTTCAC 3'
or (SEQ ID NO: 23)
5'CGGCCGCACCGGTATGTCTCCCTGAGCTTCAGGGAGGGAGAAATAAGGCCTACTTCAC 3', respectively,
``` and the reverse primer:

```
                                                                (SEQ ID NO: 24)
      5'CGCGGATCCCGTTCGGTAAGCATTAGG 3',
``` and then inserted into the PQCXIP expression vector.

To generate Lys and RPLys constructs, tRNA$_{AAA}^{Lys}$ with 5' and 3' presequences was PCR amplified from human mtDNA using the forward primers:

```
                                                                (SEQ ID NO: 25)
5'CGGCCGCACCGGTATGCATGCATGCCCATCGTCCTAG 3'
or (SEQ ID NO: 26)
5'CGGCCGCACCGGTATGTCTCCCTGAGCTTCAGGGAGGCATGCCCATCGTCCTAG 3', respectively,
``` and the reverse primer:

```
                                                                (SEQ ID NO: 27)
            5'CGCGGATCCGGGTGATGAGGAATAGTG 3',
``` and then inserted into the PQCXIP expression vector.

To make LeuA and RPLeuA constructs, the reverse primer for Leu and RPLeu was replaced with:

```
                                                                (SEQ ID NO: 28)
      5'CCGCCGCTCGAGGGGTTTGTTAAGAAGAGGAATTGAACC 3'.
```

To make LysA and RPLysA constructs, the reverse primer for Lys and RPLys was replaced with:

```
                                                                (SEQ ID NO: 29)
      5'CCGCCGCTCGAGAGAGCCCACTGTAAAGAGGTGTTG 3'.
```

To make LeuM, RPLeuM, LeuAM, RPLeuAM, LysM, RPLysM, LysAM, and RPLysAM constructs the 3'-UTR of MRPS12 was PCR amplified from human gDNA with primers:

```
                                         (SEQ ID NO: 30)
  Forward: 5'CGCGGATCCCATCAGAAGAAGTGACGGCTG 3'
  and (SEQ ID NO: 31)
  Reverse: 5'CCGGAATTCTAGTGGTCCTGATGGAA 3',
``` and then inserted into Leu, RPLeu, LeuA, RPLeuA, Lys, RPLys, LysA, RPLysA constructs, respectively.

The relevant sequences are as follows (Underline: Mitochondria importing stem-loop; Bold: elongated tRNA stem; Italics: mitochondrial targeting UTR):

```
DNA sequence for H1 RNA stem-loop:
                                         (SEQ ID NO: 32)
TCTCCCTGAGCTTCAGGGAG DNA sequence for MRP RNA stem-loop:
                                         (SEQ ID NO: 33)
AGAAGCGTATCCCGCTGAGC DNA sequence for Mitochondrial ribosomal protein
S12 (MRPS12) 3'-UTR:
                                         (SEQ ID NO: 34)
CAGAAGAAGTGACGGCTGGGGGCACAGTGGGCTGGGCGCCCTGCAGAAC

ATGAACCTTCCGCTCCTGGCTGCCACAGGGTCCTCCGATGCTGGCCTTTG

CGCCTCTAGAGGCAGCCACTCATGGATTCAAGTCCTGGCTCCGCCTCTTC

CATCAGGACCACT

DNA sequence for RPLeuAM:
                                         (SEQ ID NO: 35)
ATGTCTCCCTGAGCTTCAGGGAGGGAGAAATAAGGCCTACTTCACaaagc gccttcccccgtaaatgatatcatctcaacttagtattatacccacaccc acccaagaacagggtttgttaagatggcagagcccggtaatcgcataaaa cttaaaactttacagtcagaggttcaattcctcttcttaacaaaccctc

GGATCCCAGAAGAAGTGACGGCTGGGGGCACAGTGGGCTGGGCGCCCCTG

CAGAACATGAACCTTCCGCTCCTGGCTGCCACAGGGTCCTCCGATGCTGG

CCTTTGCGCCTCTAGAGGCAGCCACTCATGGATTCAAGTCCTGGCTCCGC

CTCTTCCATCAGGACCACT

DNA sequence for RPLysAM:
                                         (SEQ ID NO: 36)
ATGTCTCCCTGAGCTTCAGGGAGGGCATGCCCATCGTCCTAGAattaatt cccctaaaaatctttgaaatagggcccgtatttaccctatagcacccct ctacccctctagagcccactgtaaagctaacttagcattaaccttttaa gttaaagattaagagaaccaacacctctttacagtgggctctGGATCCCA

GAAGAAGTGACGGCTGGGGGCACAGTGGGCTGGGCGCCCCTGCAGAACAT

GAACCTTCCGCTCCTGGCTGCCACAGGGTCCTCCGATGCTGGCCTTTGCG

CCTCTAGAGGCAGGCACTCATGGATTCAAGTCCTGGCTCCGCCTCTTCCA

TCAGGACCACT

DNA sequence for RP-hCOX2:
                                         (SEQ ID NO: 37)
ATGTCTCCCTGAGCTTCAGGGAGGATGGCACATGCAGCGCAAGTAGGTCT

ACAAGACGCTACTTCCCCTATCATAGAAGAGCTTATCACCTTTCATGATC

ACGCCCTCATAATCATTTTCCTTATCTGCTTCCTAGTCCTGTATGCCCTT

TTCCTAACACTCACAACAAAACTAACTAATACTAACATCTCAGACGCTCA

GGAAATAGAAACCGTCTGAACTATCCTGCCCGCCATCATCCTAGTCCTCA

TCGCCCTCCCATCCCTACGCATCCTTTACATAACAGACGAGGTCAACGAT

CCCTCCCTTACCATCAAATCAATTGGCCACCAATGGTACTGAACCTACGA

GTACACCGACTACGGCGGACTAATCTTCAACTCCTACATACTTCCCCCAT

TATTCCTAGAACCAGGCGACCTGCGACTCCTTGACGTTGACAATCGAGTA

GTACTCCCGATTGAAGCCCCCATTCGTATAATAATTACATCACAAGACGT

CTTGCACTCATGAGCTGTCCCCACATTAGGCTTAAAAACAGATGCAATTC

CCGGACGTCTAAACCAAACCACTTTCACCGCTACACGACCGGGGGTATAC

TACGGTCAATGCTCTGAAATCTGTGGAGCAAACCACAGTTTCATGCCCAT

CGTCCTAGAATTAATTCCCCTAAAAATCTTTGAAATAGGGCCCGTATTTA

CCCTATAG
```

Isolation of mtRNA and mtDNA

Mitochondria (1 mg/ml) were isolated using mannitol-sucrose buffer (0.225 M mannitol, 75 mM sucrose, 5 mM HEPES pH 7.4). Mitochondria were treated with 25 µg/ml of micrococcal nuclease S7 in nuclease buffer (0.6 M sorbitol, 20 mM $MgCl_2$, 5 mM $CaCl_2$, 20 mM Tris pH 8.0) supplemented with digitonin (0.1 mg/mg protein) for 30 min at 27° C. The reaction was stopped by addition of 20 mM EGTA. Mitochondria were collected and solubilized in SDS buffer (100 mM NaCl, 1% SDS, 20 mM Tris pH 7.4) at 65° C. for 5 min. RNA was purified using TRIzol reagent, and treated with RNase-free DNase I (Roche) for 1 h at 37° C. DNase I was inactivated by heating at 65° C. for 10 min. Phenol-chloroform extractions were used for DNA purification from the mitochondrial lysates.

RT-PCR

RNA was extracted using TRIzol and first strand cDNA synthesized using the AccessQuick™ RT-PCR kit (Promega Corporation, Madison, Wis.) and a specific reverse primer. AMV reverse transcriptase was denatured at 95° C. for 5 min. Specific forward primers were added and PCR amplifications were carried out in the same tubes.

Western Blot

Mitochondrial lysates (50 µg) were resolved by SDS-PAGE, transferred to nitrocellulose membranes, and incubated for 1 h with 5% milk TBST and 1 h with primary antibodies in 5% milk TBS-T. Antibodies included α-PNPASE (1:5000) (Rainey et al. (2006) Mol Cell Biol 26: 8488-8497; and Chen et al. (2006) Mol Cell Biol 26: 8475-8487), α-COX2 (1:1000) (Santa Cruz Biotechnology, Inc., Santa Cruz, Calif.), α-ND6 (1:1000) (Santa Cruz Biotechnology), and α-TOMM40 (1:1000). Amersham ECL™ Western Blotting Detection Reagent (G.E. Healthcare Biosciences, Pittsburg, Pa.) was used for chemiluminescent detection.

In Vitro Transcription

RNAs were synthesized using the Megascript® SP6 kit (Ambion brand by Life Technologies). For radiolabeled RNA synthesis, [$^{32}$P]-CTP (MP Biomedical) was incorporated. The RNAs were purified using TRIzol reagent.

RNA Import Assay

In vitro RNA import assays were performed as previously described (Wang et al. (2010) Cell 142: 456-467) in a 200-µl volume containing 0.5 µg RNA, 100 µg mitochondria, 0.225

M mannitol, 0.075 M sucrose, 2 mM $KH_2PO_4$, 50 mM KCl, 10 mM $MgCl_2$, 2.5 mM EDTA, 5 mM L-methionine, 1 mg/ml BSA, 5 mM ATP, 2 mM DTT, 20 mM succinate, 50 mM HEPES, pH 7.1, at RT for 10 min. Mitochondria were pelleted at 11,000×g for 5 min and washed once with wash buffer (0.225 M mannitol, 0.075 M sucrose, 20 mM Tris, pH 8.0). Mitochondria were spun again and resuspended in 200 μl nuclease buffer containing 25 μg/ml of micrococcal nuclease S7 and incubated for 30 min at 27° C. Mitochondria were collected and solubilized in SDS buffer at 65° C. for 5 min. RNA was purified using TRIzol reagent, and analyzed by SDS-PAGE and autoradiography.

In Organello Translation

Following a 2 min incubation at RT with the in vitro synthesized tRNAs in the in vitro RNA import buffer, 250 μg/ml of rNTP was added and the samples were incubated at RT for an extra 5 min. RNase A was added to digest the non-imported RNA at 27° C. for 20 min. The mitochondria were then pelleted at 11,000×g for 5 min and resuspended in translation buffer containing 0.225 M mannitol, 0.075 M sucrose, 100 mM KCl, 1 mM $MgCl_2$, 0.05 mM EDTA, 10 mM Tris, 10 mM $K_2HPO_4$ pH 7.4, 10 mM glutamate, 2.5 mM malate, 1 mM ADP, 1 mg/ml fatty acid free BSA, 100 μg/memetine, 10 μM of each amino acid and 100 μCi of PRO-MIX™ L-[$^{35}$S] methionine and cysteine (MP Biomedical), and incubated at 37° C. for 30 min. Translation products were analyzed by 14% SDS-PAGE and autoradiography.

In Vivo Mitochondrial Translation

In vivo mitochondrial translation assays were performed as previously described (Hao & Moraes (1996) J Biol Chem 271: 2347-2352). Semi-confluent cells (0.5×10$^6$) were incubated in DMEM with 10% dialyzed FCS lacking methionine and cysteine and supplemented with 0.2 mg/ml emetine for 5 min at 37° C. 200 μCi/ml of PRO-MIX™ L-[$^{35}$S] methionine and cysteine (MP Biomedical) was added followed by a 30 min incubation at 37° C. Cells were PBS-washed, lysed, and analyzed by 14% SDS-PAGE and autoradiography.

Oxygen Consumption

Cells were seeded at 50,000 cells/well in a XF24 Extracellular Flux Analyzer cell culture plate (Seahorse Bioscience, North Billerica, Mass.) and incubated in the 37° C. incubator with 5% $CO_2$ for 24 h. The oxygen consumption rate was measured using the XF24 Extracellular Flux Analyzer using protocols supplied by the manufacturer.

Results

H1 RNA Import Sequence Regulates Mitochondrial Import of mt-tRNA Precursors

Figure 15A:
FIGS. 15A-15B show that the H1 RNA import sequence regulates mitochondrial import of mt-tRNA precursors.
Figure 15B:
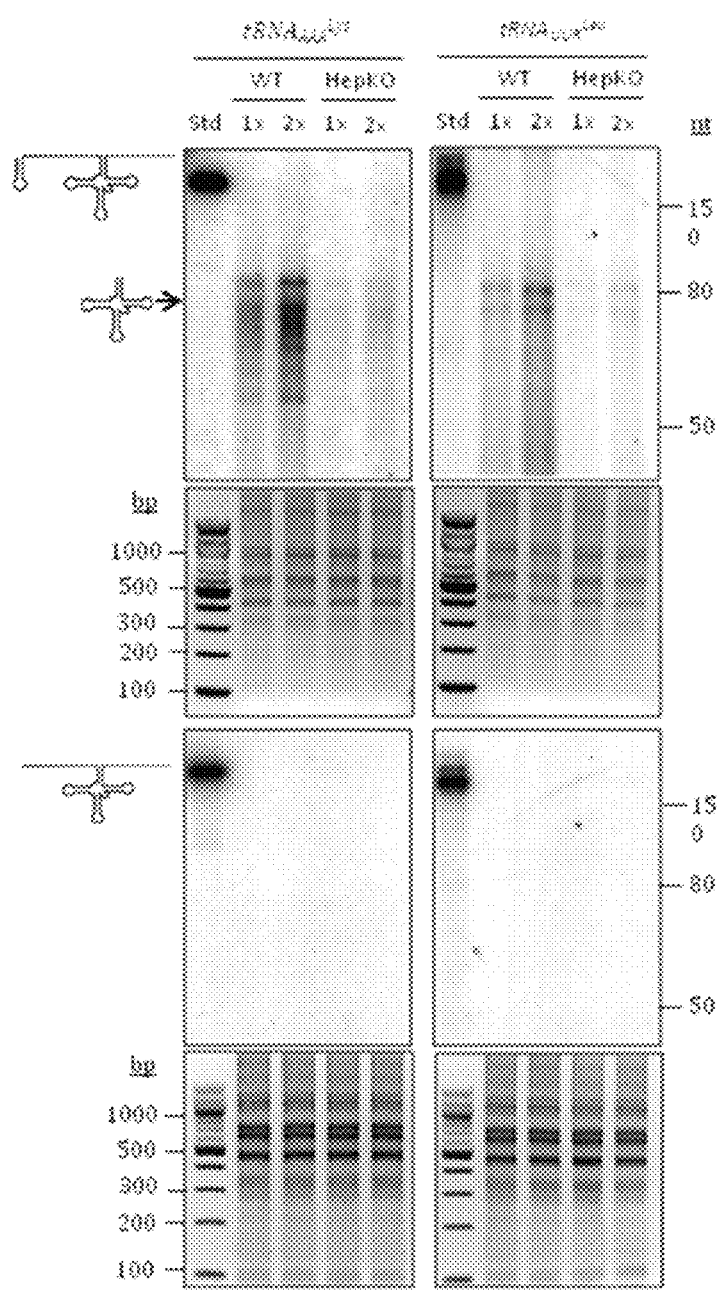

Initially, it was determined whether corrective, in vitro synthesized mitochondrial tRNA (mt-tRNA) precursors could be imported into isolated mitochondria and, if so, whether they were processed into mature mt-tRNAs. The mt-tRNA$_{AAA}^{Lys}$ precursor contains 67 and 74 ribonucleotides, and the mt-tRNA$_{UUU}^{Leu}$ precursor contains 93 and 76 ribonucleotides that are cleaved from the 5' and 3' transcript ends, respectively, during mt-tRNA maturation (Anderson et al. (1981) Nature 290: 457-465). In engineering the imported mt-tRNAs, the 5' end of each mt-tRNA precursor contained or lacked the 20-nucleotide stem loop sequence of H1 RNA that directs the import of this RNA component of the RNase P enzyme; this sequence is designated the RP import sequence (Wang et al. (2010) Cell 142: 456-467). Engineered tRNAs were then added to import assays that utilized mouse liver mitochondria isolated from wild-type or a liver-specific "knockout" (designated HepKO) of Pnpt1, the gene encoding for PNPASE (Wang et al. (2010) Cell 142: 456-467) (FIG. 15A). Only mt-tRNA precursors with the appended RP import sequence were efficiently imported into isolated mitochondria, and import was markedly impaired in mitochondria with reduced PNPASE expression (FIGS. 15A-15B). Importantly, the 5' and 3' mt-tRNA precursor sequences were removed inside the mitochondria to yield mature 60-80 ribonucleotide mt-tRNAs (FIG. 15B).

Figure 16A:
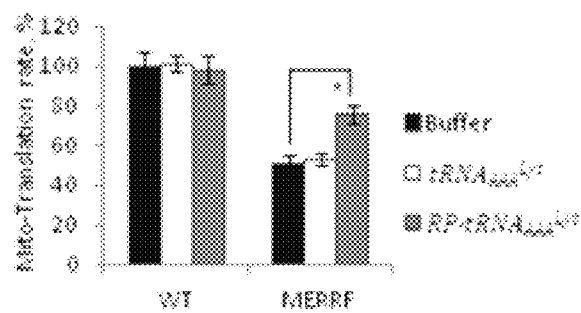
FIGS. 16A-16B are graphs showing that import mt-tRNA precursors with the RP import sequence partially rescues the translation defect of isolated MERRF and MELAS mutant mitochondria. mt-tRNA precursors with or without RP were imported into isolated WT or MERRF (FIG. 16A) or MELAS (FIG. 16B) mitochondria from cybrid lines for 2 min. Following RNase A digestion of the non-imported mt-tRNA, mitochondria were pelleted and resuspended in an in organello translation buffer with radiolabeled methionine and cysteine for 30 min. Total $^{35}$S incorporation was quantified by autoradiography.
Figure 16B:
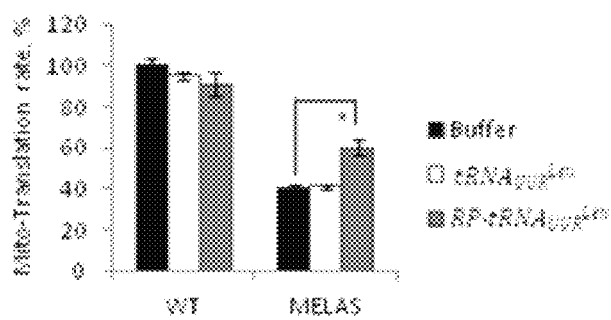

To examine whether the imported mt-tRNAs could rescue defective mtRNA translation, in vitro import was combined with mitochondrial in organello protein synthesis studies. The A8344G mutation (mt-tRNA$_{AAA}^{Lys}$) in MERRF and the A3243G mutation (mt-tRNA$_{UUR}^{Leu}$) in MELAS cause a substantial reduction in mtRNA translation (Masucci et al. (1995) Mol Cell Biol 15: 2872-2881; and Schon et al. (1992) Biochim Biophys Acta 1101: 206-209). As shown in FIGS. 16A and 16B, a statistically significant increase in the steady-state abundance of total translated mitochondrial polypeptides was observed in both MERRF and MELAS cells following incubation with the mt-tRNA precursors containing the RP import sequence, but not with mt-tRNA precursors lacking RP. These data indicate that the RP import sequence enabled PNPASE-dependent mt-tRNA precursor import into isolated mitochondria and that the imported mt-tRNA precursors were processed and functioned in at least partially correcting defective mtRNA translation.

The RP Import Sequence Directs Import of mt-tRNAS into Mitochondria In Vivo

Figure 17A:
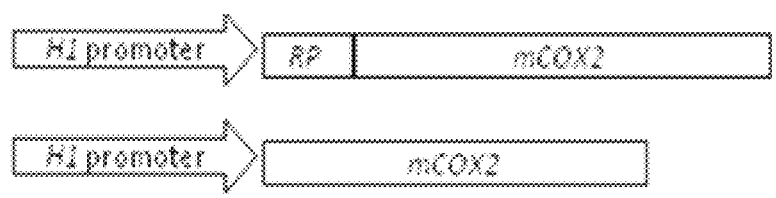
FIGS. 17A-17C show that in vivo import of mitochondrial-coded-COX2 into mitochondria using the RP import sequence.
Figure 17B:
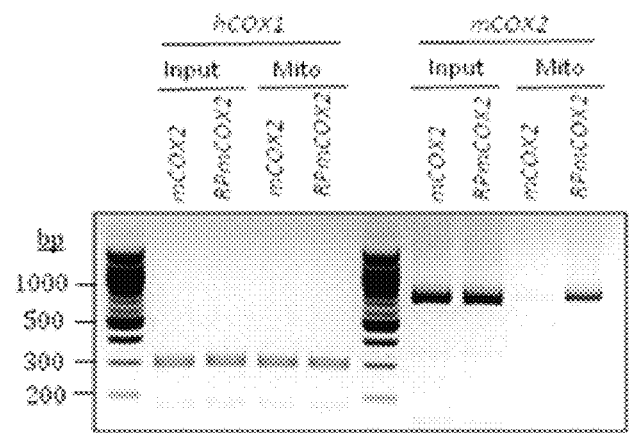

To determine whether the RP import sequence functions in vivo, a mouse cytochrome oxidase 2 (mCOX2) mRNA was used for import into human cells, since the sequence of mCOX2 differs significantly from human COX2 (hCOX2) (Bibb et al. (1981) Cell 26: 167-180; and Anderson et al. (1981) Nature 290: 457-465). The mCOX2 gene, with or without the added 5' RP import sequence, was placed under the control of the H1 promoter (FIG. 17A) and constructs were introduced into HeLa cells via transient transfection. Two days after transfection, mitochondria were isolated and subjected to digitonin treatment (100 μg/1 mg of mitochondrial protein) in the presence of nuclease to generate mitoplasts as a means to determine whether the mCOX2 RNA was indeed imported into the mitochondrial matrix. The presence of the mCOX2 RNA in the mitochondrial matrix was examined by RT-PCR. As shown in FIG. 17B, only the mtRNA fusion transcript containing the RP import sequence directed the mCOX2 transcript into the mitochondrial matrix, indicating that the RP import sequence is required and functions in vivo.

Figure 17C:
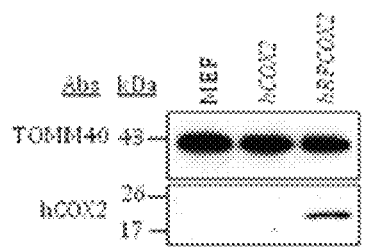
Figure 18:
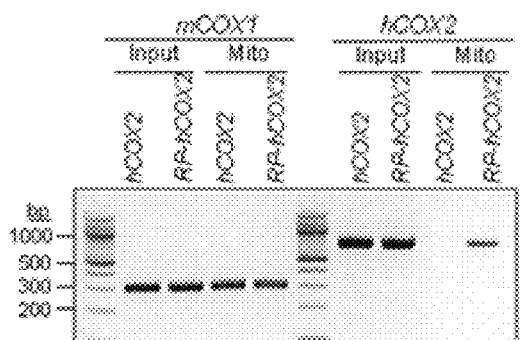
FIG. 18 shows that the RP-hCOX2 transcript but not hCOX2 transcript is imported into mitochondria when stably expressed in MEFs. Mitochondria were isolated from MEFs stably expressing hCOX2 or RP-hCOX2. Mitoplasts were generated by digitonin treatment, followed by nuclease addition to degrade RNA localized outside of the matrix. RNA was then isolated from total cell lysates (Input, without nuclease treatment) or from nuclease-treated mitoplasts (Mito) and analyzed by primer-specific RT-PCR. mCOX1 is a primer set for the mouse COX2 transcript and is included as a control for total and mitochondria-isolated RNAs.

To examine whether the imported mtRNA is translated, hCOX2 expression constructs, with or without the RP import sequence, were generated and stably introduced into mouse embryonic fibroblasts, because the monoclonal COX2 antibody is specific for human COX2 protein. Cells expressing RP-hCOX2, but not hCOX2, nucleus-encoded mtRNA showed mitochondrial transcript import (FIG. 18) and hCOX2 protein translation within mitochondria (FIG. 17C), indicating that the RP import sequence also is required and functions with coding mtRNAs in vivo. The data also show that the RP import sequence enables mitochondrial import and processing of RNAs much larger (683 ribonucleotides) than tRNAs (60-80 ribonucleotides), providing a broader therapeutic potential. Thus, the RP import sequence can potentially be utilized in general strategies to target large RNAs for import into mitochondria.

Functional Rescue of Mitochondrial tRNA Mutants

Figure 19A:
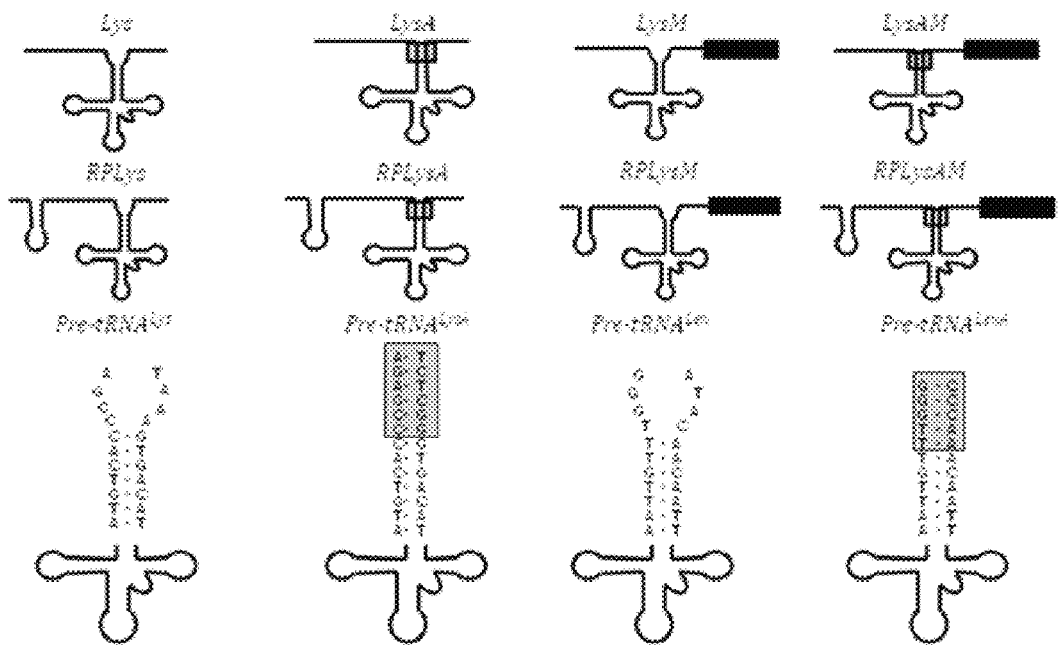
FIGS. 19A-19C show that three elements, i.e. the extended stem, the RP import sequence, and MRPS12 3'-UTR, resulted in the rescue of mt-tRNA respiratory defects in vivo by the mt-tRNA precursors encoded in the nucleus.
Figure 19B:
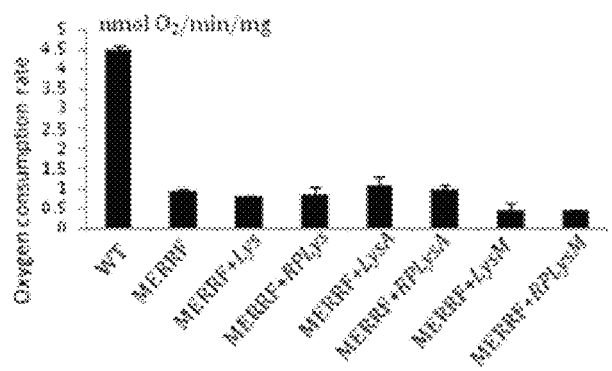
Figures 20A, 20B, 20C:
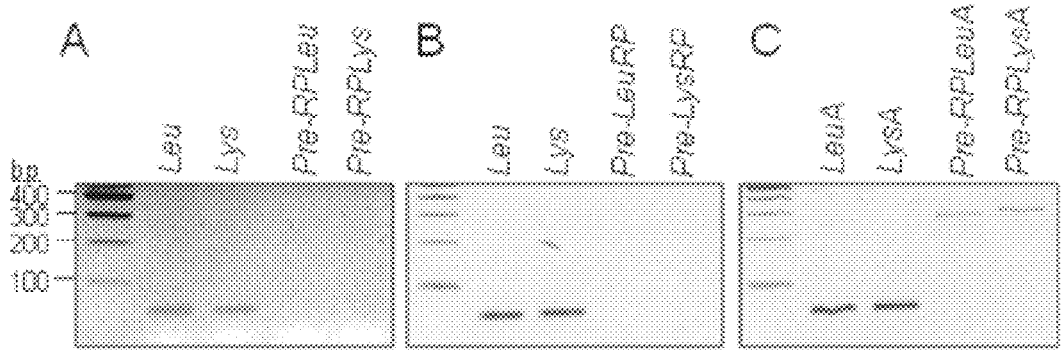
FIGS. 20A-20C show the analysis of tRNA expression in the cytosol in control experiments for FIGS. 19A-19C. tRNAs were stably expressed in wild-type cells to analyze the export requirements to shuttle the tRNA from the nucleus to the cytosol. RNA was isolated from the cytosol fraction of the wild-type cells stably expressing tRNAs for Pre-RPLeu and Pre-RPLys (FIG. 20A) and for Pre-LeuRP and Pre-LysRP (FIG. 20B). Export was analyzed by RT-PCR using primers for processed tRNAs and their precursors or for precursors only. Controls include mature tRNAs for Leu and Lys, which were exported to the cytosol.

The usual processing of nucleus-encoded tRNA precursors occurs inside the nucleus (Ceballos & Vioque (2007) Prot Peptide Lett 14: 137-145; and Frank & Pace (1998) Ann Rev Biochem 67: 153-180). However, when stably expressed from inside the nucleus, mt-tRNA precursors fused to the RP import sequence did not rescue the respiratory defect of MERRF or MELAS cells (FIGS. 19A-19B). Instead, the RP 5' mt-tRNA pre-sequences (RP 5' pre-sequences, RNA sequences having the RP import sequence fused to their 5' ends) were cleaved inside the nucleus (FIG. 20A). Moving the RP import signal to the 3' end of the mt-tRNA pre-sequence (RP 3' pre-sequences, RNA sequences having the RP import sequence fused to their 3' ends) was also ineffective as RP pre-sequences (RP 5' pre-sequences and RP 3' pre-sequences) were cleaved in the nucleus (FIG. 20B). To stop the cleavage of mt-tRNA sequences fused to the RP import sequence inside the nucleus, several ribonucleotides adjacent to the aminoacyl stem of the mt-tRNA were replaced, thereby creating mt-tRNA precursors: LysA, RPLysA, LeuA and RPLeuA (FIG. 19A). When LysA, RPLysA, LeuA and RPLeuA were expressed in mammalian cells, an increase in unprocessed mt-tRNA precursors was detected (FIG. 20C). However, these nucleus-encoded mt-tRNA precursors still failed to effectively rescue the MERRF or MELAS respiration defect (FIG. 19B).

Thus, it was hypothesized that the mt-tRNA precursors might not localize near the mitochondria and, therefore, the RP import sequence could not function as an import signal, as it does with isolated mitochondria in vitro. To determine whether localizing the mt-tRNA precursors to mitochondrion will assist in their import in vivo, the 3'-UTR of the mRNA of human mitochondrial ribosomal protein S12 (MRPS12) (Russo et al. (2008) Biochim Biophys Acta 1779: 820-829) was fused to the to the 3' end of the tRNA precursors to give the following 8 expression constructs: LysM (mt-tRNA$_{AAA}^{Lys}$ precursor with MRPS12 3'-UTR), RPLysM (mt-tRNA$_{AAA}^{Lys}$ precursor with RP and MRPS12 3'-UTR), LysAM (mt-tRNA$_{AAA}^{Lys}$ precursor with the extended stem and MRPS12 3'-UTR), RPLysAM (mt-tRNA$_{AAA}^{Lys}$ precursor with RP, the extended stem, and MRPS12 3'-UTR), LeuM (mt-tRNA$_{UUR}^{Leu}$ precursor with MRPS12 3'-UTR), RPLeuM (mt-tRNA$_{UUR}^{Leu}$ precursor with RP and MRPS12 3'-UTR), LeuAM (mt-tRNA$_{UUR}^{Leu}$ precursor with the extended stem and MRPS12 3'-UTR), and RPLeuAM (mt-tRNA$_{UUR}^{Leu}$ precursor with RP, the extended stem, and MRPS12 3'-UTR) (FIG. 19A).

Figure 19C:
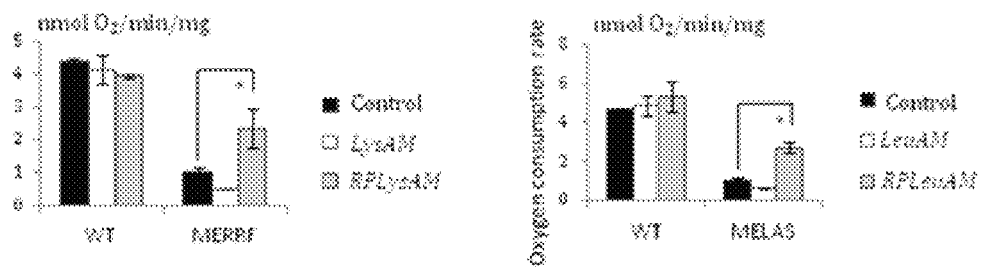

Stable polyclonal transfectants with above mentioned tRNA chimeras in MERRF and MELAS cells were made and cell respiration was measured with a XF24 Extracellular Flux Analyzer (Seahorse Biosciences, North Billerica, Mass.). As shown in FIG. 19C, when all three elements, i.e. the extended stem, the RP import sequence, and the MRPS12 3'-UTR, were present, the mt-tRNA precursors rescued MELAS and MERFF respiration defects (about a 2.5-fold increase); otherwise, no rescue was detected. FIG. 19C also shows that expression of mt-tRNA precursors in vivo did not have any significant effect on the respiration of wild-type cybrid cells (i.e. the mitochondrial genome is wild-type (as compared to the mutants)), suggesting little perturbation of other cellular functions.

Figure 21A:
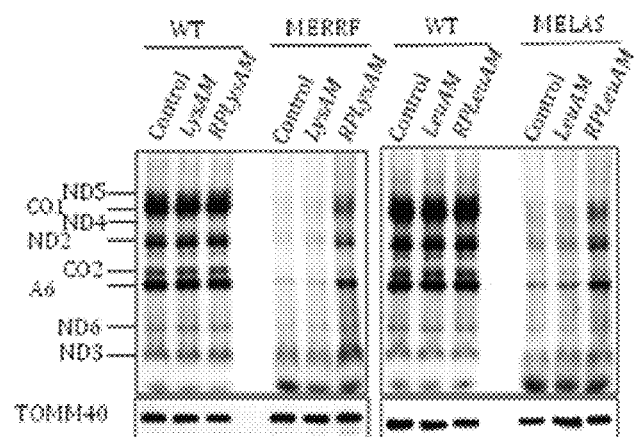
FIGS. 21A-21C show that the rescue of respiration is due to restoration of mitochondrial translation.
Figure 21B:
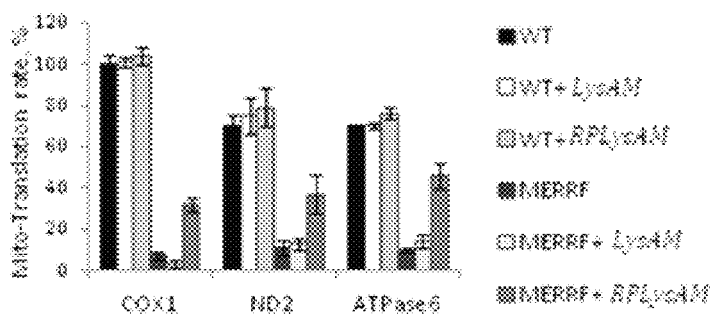
Figure 21B:
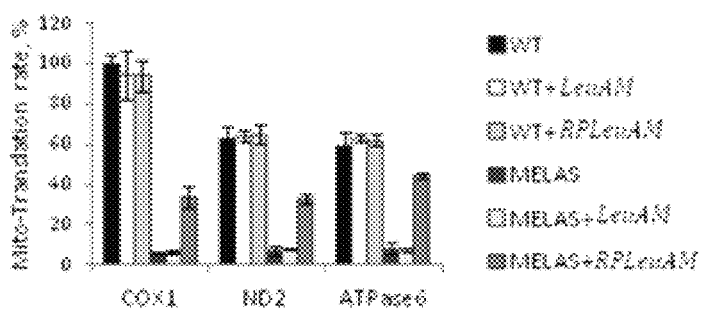
Figure 21C:
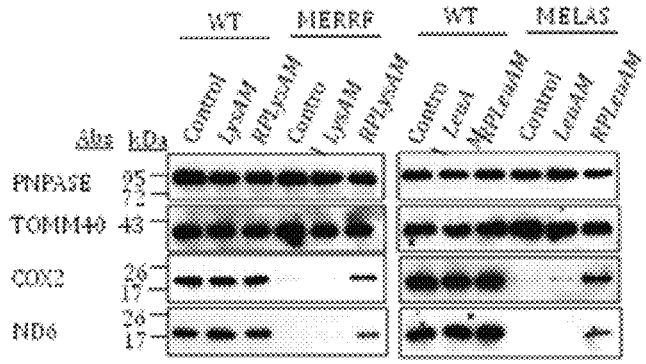

To evaluate whether the rescue of respiration is from a correction in mtRNA translation by imported wild-type mt-tRNAs, an in vivo mitochondrial translation assay was performed with MERRF and MELAS cells expressing different versions of the mt-tRNA precursors. Consistent with the respiration results, MERRF and MELAS cells showed a substantial reduction in the synthesis of mitochondrion-encoded proteins compared to the wild-type cybrid cells. Only when the mt-tRNA precursors with all three elements were expressed, did mitochondrial protein synthesis recover (about 3 to about 6 times increase) as shown in FIGS. 21A and 21B. A complete recovery was not expected, as the mutant mt-tRNAs were still present in the mitochondria and likely compete with the imported wild-type mt-tRNAs during mtRNA translation. Stable mitochondrial protein levels in MERRF and MELAS cells were also examined. Consistent with the increase in respiration and in vivo translation results in the mutant cells expressing the mt-tRNA precursors containing all three elements, as shown in FIG. 21C, the levels of mitochondrial-encoded COX2 and ND6 proteins were markedly increased.

These results show that (1) an extended stem allows some nucleus-encoded mt-tRNA precursors to escape the nucleus, (2) a mitochondria localization sequence (such as MRPS12 3'-UTR) may be used to localize RNA sequences (such as nucleus-encoded mt-tRNA precursors that have escaped the nucleus) to be in the proximity of a mitochondrion, and (3) an RNA import sequence (such as RP import sequence) may fused to an RNA sequence to cause it to be internalized by mitochondria. Thus, where a nucleus-encoded mt-tRNA precursor fails to escape the nucleus, its aminoacyl stem may be modified and/or extended to enable its escape from the nucleus. In cases where a nucleus-encoded mt-tRNA precursor escapes the nucleus but is not further processed, a mitochondria localization sequence may be used to localize the nucleus-encoded mt-tRNA precursor to be in the proximity of mitochondria. And finally, in cases where an RNA sequence is in the proximity of mitochondria but is not internalized by the mitochondria, an RNA import sequence may be used to enable its internalization by mitochondria. In some embodiments, one or more of these inventive targeting methods, i.e. use of a modified and/or extended stem, use of a mitochondria localization sequence, and use of an RNA import sequence, may be used.

RNA import sequences according to the present invention include: RP import sequence (SEQ ID NO:7) and MRP import sequence (SEQ ID NO:6) and sequences having about 15-30 nucleotides and about 80-99%, preferably about 85-99%, more preferably about 90-99%, most preferably about 95-99% sequence identity to RP import sequence (SEQ ID NO:7) or MRP import sequence (SEQ ID NO:6) yet are still capable of forming a single stem-loop such as: GUC-CCUGAGCUUCAGGGAC (SEQ ID NO:38). In some embodiments, RNA import sequences according to the present invention are about 15-30, preferably about 20-25, nucleotides long and comprise the following sequence CCCUGAGCUUCAGGG (SEQ ID NO:39). In these embodiments, one or more nucleotides may flank one or both ends of SEQ ID NO:39.

According to the present invention, a variety of modifications in the stem of a tRNA may be made in order to prevent cleavage and enable export out of the nucleus. Normally, in nuclear tRNA precursors, the first or more nucleotides preceding the mature 5' end are unpaired, which creates a bubble and facilitates processing of the 5' presequence by nuclear RNase P RNase. Extending and/or modifying the tRNA aminoacyl stem by turning the mismatched nucleotides into pairs significantly reduces the efficiency of tRNA processing. See e.g. FIG. 19A.

C. Therapeutic Embodiments

As provided above, the experiments with cytoplasmic hybrids (cybrids) evidence that the methods and sequences of the present invention may be used to treat mitochondrial genetic disorders in subjects. Cybrid lines derived from MERRF (myoclonic epilepsy with ragged red fibers) and MELAS (mitochondrial encephalomyopathy, lactic acidosis and stroke-like episodes) patient samples (Masucci et al. (1995) Mol Cell Biol 15: 2872-2881; Schon et al. (1992) Biochim Biophys Acta 1101: 206-209; Kishnani et al. (1996)

Eur Journal Pediat 155: 898-903; and Shoffner et al. (1990) Cell 61: 931-937) are longstanding models of human mtDNA disease. Mutant cybrid lines harboring an A8344G (mt-tRNA$_{AAA}^{Lys}$) mutation for MERRF and an A3243G (mt-tRNA$_{UUR}^{Leu}$) mutation for MELAS exhibit defective cell respiration resulting from inefficient mtRNA translation. The experiments herein demonstrate that mitochondrial defects in these mutant cybrid cells can be partially rescued by targeted import of allotopically-encoded wild-type tRNAs using an RNA import signal according to the present invention and, for corrective tRNAs, a mitochondrial localization signal according to the present invention, such as that derived from the 3' untranslated region (UTR) of human mitochondrial ribosomal protein S12 (MRPS12), which targets the mRNA to the mitochondrial outer membrane (Russo et al. (2008) Biochim Biophys Acta 1779: 820-829). The experiments herein also show that the RP import sequences according to the present invention are capable of importing much larger, mitochondrial protein-encoding mRNAs in vivo. Consequently, the methods and compositions of the present invention may be used to treat a variety of mitochondrial genetic disorders which are not limited by the size of the relevant mtDNA gene.

In some embodiments, the RNA import sequences of the present invention are used to rationally engineer tRNAs and mRNAs that are internalized by mitochondria such as human mitochondria. In some embodiments, the stems of nucleus-encoded tRNAs are modified and/or extended in order to prevent their cleavage inside of the nucleus and enable their transport out of the nucleus. In some embodiments, a mitochondria localization sequence of the present invention may be fused to a given nucleic acid molecule, e.g. an RNA sequence, in order to localize the nucleic acid molecule to be in proximity to mitochondria.

Thus, the present invention also provides wild-type or altered nucleic acid molecules, which may be RNA or ssDNA, that are recombinantly modified to have fused thereto an RNA import sequence, a mitochondria localization sequence, or a combination thereof. In addition, the present invention may be used treat mtDNA mutations in mt-tRNAs, mt-rRNAs, and protein-encoding mtRNAs by importing wild type tRNAs, rRNAs and mRNAs into mitochondria to thereby complement the mutations in the genes. The present invention may also be used to treat heteroplasmic mtDNA populations, in which ribozymes are targeted by importing enzymatic RNAs or other noncoding RNAs that can be used to manipulate the levels of mitochondrial encoded RNAs.

As provided herein, rationally designed RNAs of the present invention do not appear to have any negative effect on other cellular processes, as wild-type cell metabolism is not affected. Therefore, the methods and compositions of the present invention may be used to treat a wide range of diseases and disorders caused by mutations in the mitochondrial genome. Examples of diseases and disorders resulting from mitochondrial dysfunction include Diabetes mellitus and deafness (DAD), Leber's hereditary optic neuropathy (LHON), Leigh syndrome, Neuropathy, ataxia, retinitis pigmentosa and ptosis (NARP), Myoneurogenic gastrointestinal encephalopathy (MNGIE), Myoclonic epilepsy with ragged red fibers (MERRF), Mitochondrial myopathy, encephalomyopathy, lactic acidosis, stroke-like symptoms (MELAS), mitochondrial myopathy, cardiomyopathy, Type II diabetes, Alzheimer's disease, Parkinson's disease, and the like.

For example, once the disease causing mutation in the mtDNA is determined, a nucleic acid molecule having a sequence that corresponds to the correct mtDNA sequence is fused to an RNA import sequence of the present invention and administered to the mitochondria having the mtDNA mutation. Tables 1 and 2 set forth various mutations (nucleotide changes) in the mitochondrial genome and the mitochondrial diseases caused thereby. Thus, in some embodiments, after a subject is diagnosed as having one of these mitochondrial diseases, the subject may be administered a recombinant nucleic acid molecule which comprises a first nucleic acid molecule which is a wild-type sequence or an altered sequence of a gene or fragment thereof or its complement, fused directly or indirectly to another nucleic acid molecule(s) which is an RNA import sequence, a mitochondria localization sequence, or a combination thereof. The first nucleic acid molecule may be RNA or ssDNA. Thus, in some embodiments, the recombinant nucleic acid molecule is a entirely composed of ribonucleotides and in other embodiments, the recombinant nucleic acid molecule is a DNA:RNA hybrid, i.e. composed of both ribonucleotides and deoxyribonucleotides.

TABLE 1

Known Mitochondrial DNA Base Substitutions Causing Diseases: Coding and Control Region Point Mutations

| Locus | Disease | Allele | Nucleotide Position | Nucleotide Change | Amino Acid Change | Homo-plasmy | Hetero-plasmy | Status |
|---|---|---|---|---|---|---|---|---|
| MT-DLOOP | BD-associated | C114T | 114 | C-T | noncoding | + | − | Reported |
| MT-DLOOP | Longevity/Cervical Carcinoma risk | C150T | 150 | C-T | noncoding | + | + | Conflicting reports |
| MT-DLOOP | BD-associated | T195C | 195 | T-C | noncoding | + | − | Reported |
| MT-DLOOP | AD-weakly associated | C309CC | 309 | C-CCins(n) | noncoding | . | . | Reported |
| MT-ND1 | MELAS/DEAF enhancer/hypertension | T3308C | 3308 | T-C | M-T | − | + | P.M.-possibly synergistic |
| MT-ND1 | Sudden Infant Death | T3308G | 3308 | T-G | M1X | + | + | Reported |
| MT-ND1 | NIDDM/HCM | C3310T | 3310 | C-T | P-S | + | + | Reported |
| MT-ND1 | NIDDM/LHON/PEO | G3316A | 3316 | G-A | A-T | + | − | Unclear |
| MT-ND1 | Cardiomyopathy | G3337A | 3337 | G-A | V-M | + | − | Possibly synergistic |
| MT-ND1 | Encephaloneuromyopathy | C3340T | 3340 | C-T | P-S | + | − | Reported |
| MT-ND1 | LHON MELAS overlap | G3376A | 3376 | G-A | E-K | + | + | Reported |
| MT-ND1 | MELAS | G3380A | 3380 | G-A | R-Q | − | + | Reported |
| MT-ND1 | LHON/NIDDM/CPTdeficiency | T3394C | 3394 | T-C | Y-H | + | − | Reported/Unclear |
| MT-ND1 | HCM with hearing loss | A3395G | 3395 | A-G | Y-C | − | + | Reported |
| MT-ND1 | NSHL/MIDD | T3396C | 3396 | T-C | syn | + | − | Warrants further study |
| MT-ND1 | ADPD/Possibly LVNC-cardiomyopathy associated | A3397G | 3397 | A-G | M-V | + | − | Reported |

TABLE 1-continued

Known Mitochondrial DNA Base Substitutions Causing Diseases: Coding and Control Region Point Mutations

| Locus | Disease | Allele | Nucleotide Position | Nucleotide Change | Amino Acid Change | Homo-plasmy | Hetero-plasmy | Status |
|---|---|---|---|---|---|---|---|---|
| MT-ND1 | DMDF + HCM/GDM/possibly LVNC cardiomyopathy-associated | T3398C | 3398 | T-C | M-T | + | − | Reported |
| MT-ND1 | Gestational Diabetes (GDM) | A3399T | 3399 | A-T | M-I | + | − | Warrants further study |
| MT-ND1 | found in 1 HCM patient | G3407A | 3407 | G-A | R-H | + | − | Reported |
| MT-ND1 | AMegL | A3418G | 3418 | A-G | N-D | + | − | Reported |
| MT-ND1 | MIDD | G3421A | 3421 | G-A | V-I | + | − | Reported |
| MT-ND1 | LHON | G3460A | 3460 | G-A | A-T | + | + | Cfrm |
| MT-ND1 | MELAS | G3481A | 3481 | G-A | E-K | − | + | Reported |
| MT-ND1 | Progressive Encephalomyopathy | G3481A | 3481 | G-A | E-K | − | + | Reported |
| MT-ND1 | LHON | G3496T | 3496 | G-T | A-S | + | − | Reported/Secondary |
| MT-ND1 | LHON | C3497T | 3497 | C-T | A-V | + | − | Reported/Secondary |
| MT-ND1 | LHON | G3635A | 3635 | G-A | S-N | + | − | Cfrm |
| MT-ND1 | BD-associated | T3644C | 3644 | T-C | V-A | . | . | Reported |
| MT-ND1 | Leigh Syndrome | G3688A | 3688 | G-A | A-T | + | − | Reported |
| MT-ND1 | MELAS/LS/LDYT | G3697A | 3697 | G-A | G-S | − | + | Cfrm |
| MT-ND1 | LHON | G3700A | 3700 | G-A | A-T | + | − | Reported |
| MT-ND1 | LHON | G3733A | 3733 | G-A | E-K | + | + | Reported |
| MT-ND1 | LHON | G3736A | 3736 | G-A | V-I | . | . | Reported |
| MT-ND1 | Adult-Onset Dystonia | A3796G | 3796 | A-G | T-A | − | + | Reported |
| MT-ND1 | PEG | T3833A | 3833 | T-A | L-Q | + | − | Reported |
| MT-ND1 | LHON + limb claudication | T3866C | 3866 | T-C | I-T | . | . | Reported |
| MT-ND1 | Progressive Encephalomyopathy/LS | G3890A | 3890 | G-A | R-Q | − | + | Reported |
| MT-ND1 | MELAS | G3946A | 3946 | G-A | E-K | + | + | Reported |
| MT-ND1 | MELAS | T3949C | 3949 | T-C | Y-H | − | + | Reported |
| MT-ND1 | NAION-assoicated | G4132A | 4132 | G-A | A-T | + | − | Warrants further study |
| MT-ND1 | LHON | A4136G | 4136 | A-G | Y-C | + | − | Possibly synergistic |
| MT-ND1 | LHON | T4160C | 4160 | T-C | L-P | + | − | Reported |
| MT-ND1 | LHON | C4171A | 4171 | C-A | L-M | + | + | Cfrm |
| MT-ND1 | LHON/Insulin Resistance | T4216C | 4216 | T-C | Y-H | + | − | P.M.-haplogroup J/T marker |
| MT-ND1 | LHON candidate | C4633G | 4633 | C-G | A-G | + | − | Reported |
| MT-ND2 | LHON | C4640A | 4640 | C-A | I-M | + | − | Reported |
| MT-ND2 | PEG | T4648C | 4648 | T-C | F-S | + | − | Reported |
| MT-ND2 | possible PD risk factor | G4659A | 4659 | G-A | A-T | + | − | Reported |
| MT-ND2 | Leigh Syndrome | T4681C | 4681 | T-C | L-P | − | + | Reported |
| MT-ND2 | SZ-associated | A4769A | 4769 | A-A | syn | + | − | Reported |
| MT-ND2 | NIDDM helper mutation; AD, PD | A4833G | 4833 | A-G | T-A | + | − | Reported; haplogroup G marker |
| MT-ND2 | LHON | T4852A | 4852 | T-A | L-Q | + | − | Reported |
| MT-ND2 | LHON/Insulin Resistance/AMD/NRTI-PN | A4917G | 4917 | A-G | N-D | + | − | Reported; haplogroup T marker |
| MT-ND2 | Longevity; Extraversion MI/AMS protection; blood iron metabolism | C5178A | 5178 | C-A | L-M | + | − | Reported; haplogroup D marker |
| MT-ND2 | LHON | G5244A | 5244 | G-A | G-S | − | + | Reported |
| MT-ND2 | Progressive Encephalomyopathy | C5452T | 5452 | C-T | T-M | + | − | Reported |
| MT-ND2 | AD/PD | G5460A | 5460 | G-A | A-T | + | + | P.M. |
| MT-ND2 | AD | G5460T | 5460 | G-T | A-S | + | + | Reported |
| MT-CO1 | Prostate Cancer | C5911T | 5911 | C-T | A-V | + | − | Reported |
| MT-CO1 | Prostate Cancer | G5913A | 5913 | G-A | D-N | + | − | Reported |
| MT-CO1 | Myoglobinuria/EXIT | G5920A | 5920 | G-A | W-Ter | − | + | Reported |
| MT-CO1 | Prostate Cancer | A5935G | 5935 | A-G | N-S | + | − | Reported |
| MT-CO1 | Prostate Cancer | G5973A | 5973 | G-A | A-T | + | − | Reported |
| MT-CO1 | Motor Neuron Disease | 6020del5 | 6020 | CGAGC-del | AELGQ-AGPATer | − | + | Reported |
| MT-CO1 | Prostate Cancer | G6081A | 6081 | G-A | A-T | + | − | Reported |
| MT-CO1 | Prostate Cancer | G6150A | 6150 | G-A | V-I | + | − | Reported |
| MT-CO1 | Prostate Cancer | T6253C | 6253 | T-C | M-T | + | − | Reported |
| MT-CO1 | Prostate Cancer/LHON | G6261A | 6261 | G-A | A-T | + | − | Reported |
| MT-CO1 | Prostate Cancer | G6267A | 6267 | G-A | A-T | + | − | Reported |
| MT-CO1 | Prostate Cancer | G6285A | 6285 | G-A | V-I | + | − | Reported |
| MT-CO1 | EXIT (Exercise Intolerance) | C6328T | 6328 | C-T | S-F | + | − | Reported |
| MT-CO1 | Prostate Cancer | C6340T | 6340 | C-T | T-I | + | − | Reported |
| MT-CO1 | Prostate Cancer | G6480A | 6480 | G-A | V-I | + | − | Reported |
| MT-CO1 | Therapy-Resistant Epilepsy | C6489A | 6489 | C-A | L-I | − | + | Reported |
| MT-CO1 | Prostate Cancer | A6663G | 6663 | A-G | I-V | + | − | Reported |
| MT-CO1 | Myopathy | A6698del | 6698 | A-del | K-fs-Ter | − | + | Reported |

TABLE 1-continued

Known Mitochondrial DNA Base Substitutions Causing Diseases: Coding and Control Region Point Mutations

| Locus | Disease | Allele | Nucleotide Position | Nucleotide Change | Amino Acid Change | Homo-plasmy | Hetero-plasmy | Status |
|---|---|---|---|---|---|---|---|---|
| MT-CO1 | MM & Rhabdomyolysis | G6708A | 6708 | G-A | G-Ter | − | + | Reported |
| MT-CO1 | Acquired Idiopathic Sideroblastic Anemia | T6721C | 6721 | T-C | M-T | − | + | Reported |
| MT-CO1 | Acquired Idiopathic Sideroblastic Anemia | T6742C | 6742 | T-C | I-T | − | + | Reported |
| MT-CO1 | Multisystem Disorder | G6930A | 6930 | G-A | G-Ter | − | + | Reported |
| MT-CO1 | Mild EXIT and MR | G6955A | 6955 | G-A | G-D | + | + | Reported |
| MT-CO1 | MELAS-like syndrome | G7023A | 7023 | G-A | V-M | − | + | Reported |
| MT-CO1 | Prostate Cancer | G7041A | 7041 | G-A | V-I | + | − | Reported |
| MT-CO1 | Prostate Cancer | T7080C | 7080 | T-C | F-L | + | − | Reported |
| MT-CO1 | Prostate Cancer | A7083G | 7083 | A-G | I-V | + | − | Reported |
| MT-CO1 | Prostate Cancer | A7158G | 7158 | A-G | I-V | + | − | Reported |
| MT-CO1 | Prostate Cancer | A7305C | 7305 | A-C | M-L | + | − | Reported |
| MT-CO1 | DEAF | A7443G | 7443 | A-G | Ter-G | + | − | Reported |
| MT-CO1 | LHON/SNHL/DEAF | G7444A | 7444 | G-A | Ter-K | + | − | Reported |
| MT-CO1 | DEAF | A7445C | 7445 | A-C | Ter-S | + | − | Reported |
| MT-CO1 | SNHL | A7445G | 7445 | A-G | Ter-Ter | + | + | Cfrm |
| MT-CO2 | Mitochondrial Encephalomyopathy | T7587C | 7587 | T-C | M-T | − | + | Reported |
| MT-CO2 | LHON | C7623T | 7623 | C-T | T-I | + | − | Reported |
| MT-CO2 | PD risk factor | G7637A | 7637 | G-A | E-K | − | + | Reported |
| MT-CO2 | MM | T7671A | 7671 | T-A | M-K | − | + | Reported |
| MT-CO2 | possible HCM susceptibility | G7697A | 7697 | G-A | V-I | + | − | Reported |
| MT-CO2 | Alpers-Huttennlocher-like | G7706A | 7706 | G-A | A41T | + | | Reported |
| MT-CO2 | Progressive Encephalomyopathy | G7859A | 7859 | G-A | D-N | + | − | Reported |
| MT-CO2 | LHON | C7868T | 7868 | C-T | L-F | + | − | Possibly synergistic |
| MT-CO2 | PEG glaucoma | A7877C | 7877 | A-C | K-Q | + | − | Reported |
| MT-CO2 | Multisystem Disorder | G7896A | 7896 | G-A | W-Ter | − | + | Reported |
| MT-CO2 | Encephalopathy | G7970T | 7970 | G-T | E-Ter | − | + | Reported |
| MT-CO2 | Rhabdomyolysis | T7989C | 7989 | T-C | L-P | − | + | Reported |
| MT-CO2 | Lactic Acidosis | 8042del2 | 8042 | AT-del | M-Ter | − | + | Reported |
| MT-CO2 | DEAF | G8078A | 8078 | G-A | V-I | + | − | Reported |
| MT-CO2 | SNHL | A8108G | 8108 | A-G | I-V | + | − | Reported |
| MT-ATP8 | MIDD/LVNC cardiomyopathy-assoc. | A8381G | 8381 | A-G | T-A | + | − | Reported |
| MT-ATP8 | Reversible Brain Pseudoatrophy | C8393T | 8393 | C-T | P-S | − | + | Reported |
| MT-ATP8 | Severe mitochondrial disorder | A8411G | 8411 | A-G | M-V | + | − | Reported |
| MT-ATP8 | Longevity | C8414T | 8414 | C-T | L-F | + | − | Reported |
| MT-ATP8/6? | Infantile cardiomyopathy | T8528C | 8528 | T-C | W-R (ATP8); M(start)-T (ATP6) | + | + | Reported |
| MT-ATP8/6? | Apical HCM | G8529A | 8529 | G-A | W-X (ATP8); M-M (ATP6) | + | − | Reported |
| MT-ATP8/6? | Possibly LVNC cardiomyopathy-associated | C8558T | 8558 | C-T | P-S (ATP8); A-V (ATP6) | + | − | Reported |
| MT-ATP6 | LHON | T8668C | 8668 | T-C | W-R | + | − | Reported |
| MT-ATP6 | MILS protective factor | T8741G | 8741 | T-G | L-R | − | + | Reported |
| MT-ATP6 | Exercise Endurance/Coronary Atherosclerosis risk | C8794T | 8794 | C-T | H-Y | + | − | Reported |
| MT-ATP6 | MILS protective factor | A8795G | 8795 | A-G | H-R | − | + | Reported |
| MT-ATP6 | LHON | A8836G | 8836 | A-G | M-V | + | − | Reported |
| MT-ATP6 | BSN | T8851C | 8851 | T-C | W-R | + | + | Reported |
| MT-ATP6 | Prostate Cancer | C8932T | 8932 | C-T | P-S | + | − | Reported |
| MT-ATP6 | LDYT | G8950A | 8950 | G-A | V-I | + | − | Reported |
| MT-ATP6 | NARP/Leigh Disease/MILS/other | T8993C | 8993 | T-C | L-P | − | + | Cfrm |
| MT-ATP6 | NARP/Leigh Disease/MILS/other | T8993G | 8993 | T-G | L-R | − | + | Cfrm |
| MT-ATP6 | LHON | A9016G | 9016 | A-G | I-V | − | + | Reported |
| MT-ATP6 | Progressive ataxia | T9035C | 9035 | T-C | L-P | + | − | Reported |
| MT-ATP6 | PD protective factor | G9055A | 9055 | G-A | A-T | + | − | Reported |
| MT-ATP6 | Possibly LVNC cardiomyopathy-associated | A9058G | 9058 | A-G | T-A | + | − | Reported |
| MT-ATP6 | Predisposition to anti-retroviral mito disease | T9098C | 9098 | T-C | I-T | + | − | Reported |
| MT-ATP6 | LHON | T9101C | 9101 | T-C | I-T | + | − | Reported |
| MT-ATP6 | LHON | G9139A | 9139 | G-A | A-T | + | − | Reported-possibly synergistic |
| MT-ATP6 | FBSN/Leigh Disease | T9176C | 9176 | T-C | L-P | + | + | Cfrm |
| MT-ATP6 | Leigh Disease/Spastic Paraplegia | T9176G | 9176 | T-G | L-R | − | + | Cfrm |
| MT-ATP6 | Leigh Disease/Ataxia/NARP-like disease | T9185C | 9185 | T-C | L-P | + | + | Cfrm |
| MT-ATP6 | Leigh Disease | T9191C | 9191 | T-C | L-P | − | + | Reported |

TABLE 1-continued

Known Mitochondrial DNA Base Substitutions Causing Diseases: Coding and Control Region Point Mutations

| Locus | Disease | Allele | Nucleotide Position | Nucleotide Change | Amino Acid Change | Homo-plasmy | Hetero-plasmy | Status |
|---|---|---|---|---|---|---|---|---|
| MT-ATP6 | Seizures/Lacticacidemia | 9205de12 | 9205 | TA-del | Ter-M | + | − | Reported |
| MT-CO3 | MM w lactic acidosis | G9379A | 9379 | G-A | W-Ter | − | + | Reported |
| MT-CO3 | LHON | G9438A | 9438 | G-A | G-S | + | − | Conflicting reports |
| MT-CO3 | Leigh Disease | T9478C | 9478 | T-C | V-A | − | + | Reported |
| MT-CO3 | Myoglobinuria | 9480del15 | 9479 | TTTTTCTT-CGCAGGA-del | FFFAG-del | − | + | Reported |
| MT-CO3 | Leigh Disease | C9537insC | 9537 | C-CC | Q-frameshift | + | − | Reported |
| MT-CO3 | Sporadic bilateral optic neuropathy | G9544A | 9544 | G-A | G-E | . | . | Reported |
| MT-CO3 | LHON | A9660C | 9660 | A-C | M-L | + | − | Reported |
| MT-CO3 | LHON | G9738T | 9738 | G-T | A-S | + | − | Reported |
| MT-CO3 | Myopathy | T9789C | 9789 | T-C | S-P | − | + | Reported |
| MT-CO3 | LHON | G9804A | 9804 | G-A | A-T | + | − | Reported |
| MT-CO3 | AD | T9861C | 9861 | T-C | F-L | + | − | Reported |
| MT-CO3 | Mitochondrial Encephalopathy | G9952A | 9952 | G-A | W-Ter | − | + | Reported |
| MT-CO3 | PEM/MELAS/NAION | T9957C | 9957 | T-C | F-L | − | + | Reported |
| MT-CO3 | EXIT & APS2-possible link | A9972C | 9972 | A-C | I-L | − | + | Warrants further study |
| MT-ND3 | Leigh Disease | T10158C | 10158 | T-C | S-P | + | + | Cfrm |
| MT-ND3 | Leigh Disease/Leigh-like Disease/ESOC | T10191C | 10191 | T-C | S-P | − | + | Cfrm |
| MT-ND3 | Leigh Disease/Dystonia/Stroke/LDYT | G10197A | 10197 | G-A | A-T | + | + | Cfrm |
| MT-ND3 | LHON | T10237C | 10237 | T-C | I-T | + | − | Reported |
| MT-ND3 | Invasive Breast Cancer risk factor; AD; PD; BD lithium response; Type 2 DM | A10398A | 10398 | A-A | T-T | + | − | Reported; haplogroup HNTUVWXK2 marker |
| MT-CYB | DEAF | G15077A | 15077 | G-A | E-K | + | − | Reported |
| MT-ND3 | PD protective factor/longevity/altered cell pH/metabolic syndrome/breast cancer risk | A10398G | 10398 | A-G | T-A | + | − | Reported; haplogroup IJK marker |
| MT-ND4L | LHON | A10543G | 10543 | A-G | H-R | − | + | Reported |
| MT-ND4L | LHON | T10591G | 10591 | T-G | F-C | − | + | Reported |
| MT-ND4L | BD/MDD-associated | T10652C | 10652 | T-C | syn | − | + | Reported |
| MT-ND4L | LHON | T10663C | 10663 | T-C | V-A | + | − | Cfrm |
| MT-ND4L | LHON | G10680A | 10680 | G-A | A-T | + | − | Reported-possibly synergistic |
| MT-ND4 | AD, PD; MELAS | A11084G | 11084 | A-G | T-A | + | + | Reported; P.M. |
| MT-ND4 | CPEO | T11232C | 11232 | T-C | L-P | − | + | Reported |
| MT-ND4 | LHON; PD | T11253C | 11253 | T-C | I-T | + | − | Reported |
| MT-ND4 | found in 1 HCM patient | T11365C | 11365 | T-C | syn | + | − | Reported |
| MT-ND4 | Altered brain pH | A11467G | 11467 | A-G | syn | + | − | Reported |
| MT-ND4 | LHON/LDYT/DEAF/hypertension helper mut. | G11696A | 11696 | G-A | V-I | | | |

Notes:
LHON Leber Hereditary Optic Neuropathy
AD Alzeimer's Disease
ADPD Alzeimer's Disease and Parkinsons's Disease
NARP Neurogenic muscle weakness, Ataxia, and Retinitis Pigmentosa; alternate phenotype at this locus is reported as Leigh Disease
MELAS Mitochondrial Encephalomyopathy, Lactic Acidosis, and Stroke-like episodes
MERRF Myoclonic Epilepsy and Ragged Red Muscle Fibers
CPEO Chronic Progressive External Ophthalmoplegia
DM Diabetes Mellitus
CIPO Chronic Intestinal Pseudoobstruction with myopathy and Ophthalmoplegia
PEM Progressive encephalopathy
MM Mitochondrial Myopathy
LIMM Lethal Infantile Mitochondrial Myopathy
MMC Maternal Myopathy and Cardiomyopathy
FICP Fatal Infantile Cardiomyopathy Plus, a MELAS-associated cardiomyopathy
LDYT Leber's hereditary optic neuropathy and DYsTonia
MHCM Maternally inherited Hypertrophic CardioMyopathy
KSS Kearns Sayre Syndrome
DMDF Diabetes Mellitus + DeaFness
DEAF Maternally inherited DEAFness or aminoglycoside-induced DEAFness
SNHL SensoriNeural Hearing Loss
Homoplasmy = pure mutant mtDNAs.

TABLE 1-continued

Known Mitochondrial DNA Base Substitutions Causing Diseases: Coding and Control Region Point Mutations

| Locus | Disease | Allele | Nucleotide Position | Nucleotide Change | Amino Acid Change | Homo-plasmy | Hetero-plasmy | Status |
|---|---|---|---|---|---|---|---|---|

Heteroplasmy = mixture of mutant and normal mtDNAs.
nd = not determined.
"Reported" status indicates that one or more publications have considered the mutation as possibly pathologic. This is not an assignment of pathogenicity by MITOMAP but is a report of literature. Previously, mutations with this status were termed "Prov" (provisional).
"Cfrm"(confirmed) status indicates that at least two or more independent laboratories have published reports on the pathogenicity of a specific mutation. These mutations are generally accepted by the mitochondrial research community as being pathogenic. A status of "Cfrm" is not an assignment of pathogenicity by MITOMAP but is a report of published literature. Researchers and clinicians are cautioned that additional data and/or analysis may still be necessary to confirm the pathological significance of some of these mutations.
"P.M." (point mutation/polymorphism) status indicates that some published reports have determined the mutation to be a non-pathogenic polymorphism.

TABLE 2

Known Mitochondrial DNA Base Substitution Causing Diseases: rNA/tRNA mutations

| Locus | Disease | Allele | RNA | Homo-plasmy | Hetero-Plasmy | Status |
|---|---|---|---|---|---|---|
| MT-TF | Mitochondrial myopathy | T582C | tRNA Phe | − | + | Reported |
| MT-TF | MELAS/MM & EXIT | G583A | tRNA Phe | − | + | Cfrm |
| MT-TF | Extrapyramidal disorder with akinesia-rigidity, psychosis and SNHL | G586A | tRNA Phe | − | + | Reported |
| MT-TF | Axial myopathy with encephalopathy | C602T | tRNA Phe | − | + | Reported |
| MT-TF | Myoglobinuria | A606G | tRNA Phe | + | + | Unclear |
| MT-TF | Tubulointerstitial nephritis | A608G | tRNA Phe | + | − | Reported |
| MT-TF | MERRF | G611A | tRNA Phe | − | + | Reported |
| MT-TF | Maternally inherited epilepsy | T616C/G | tRNA Phe | + | + | Reported |
| MT-TF | MM | T618C | tRNA Phe | − | + | Reported |
| MT-TF | EXIT & Deafness | G622A | tRNA Phe | − | + | Reported |
| MT-TF | DEAF | A636G | tRNA Phe | + | − | Reported |
| MT-TF | Ataxia, PEO, deafness | T642C | tRNA Phe | − | + | Reported |
| MT-RNR1 | Coronary Atherosclerosis risk | A663G | 12S rRNA | + | − | Reported |
| MT-RNR1 | DEAF | T669C | 12S rRNA | + | − | Reported |
| MT-RNR1 | Possibly LVNC-associated | T721C | 12S rRNA | + | − | Reported |
| MT-RNR1 | DEAF | A735G | 12S rRNA | . | . | Reported |
| MT-RNR1 | DEAF-associated | A745G | 12S rRNA | + | − | Reported |
| MT-RNR1 | SZ-associated | A750A | 12S rRNA | + | − | Reported |
| MT-RNR1 | Increased risk of nonsyndromic deafness | C792T | 12S rRNA | + | − | Reported |
| MT-RNR1 | DEAF-associated | A801G | 12S rRNA | + | − | Reported |
| MT-RNR1 | DEAF | A827G | 12S rRNA | + | − | Conflicting reports-B4b'd marker |
| MT-RNR1 | DEAF-associated | A839G | 12S rRNA | + | − | Reported |
| MT-RNR1 | Possibly LVNC-associated | T850C | 12S rRNA | + | − | Reported |
| MT-RNR1 | LHON helper/AD/DEAF-associated | A856G | 12S rRNA | + | − | Reported |
| MT-RNR1 | found in 1 HCM patient | C869T | 12S rRNA | + | − | Reported |
| MT-RNR1 | Possibly LVNC-associated | T921C | 12S rRNA | + | − | Reported |
| MT-RNR1 | Possibly DEAF-associated | C960CC | 12S rRNA | + | − | Reported |
| MT-RNR1 | Possibly DEAF-associated | C960del | 12S rRNA | + | − | Reported |
| MT-RNR1 | DEAF, possibly LVNC-associated | T961C | 12S rRNA | + | − | Unclear |
| MT-RNR1 | DEAF/AD-associated | T961delT +/− C(n)ins | 12S rRNA | + | + | Unclear |
| MT-RNR1 | Possibly DEAF-associated | T961G | 12S rRNA | + | − | Reported |
| MT-RNR1 | DEAF | T961insC | 12S rRNA | + | − | Unclear |
| MT-RNR1 | Possible DEAF risk factor | G988A | 12S rRNA | . | . | Reported |
| MT-RNR1 | DEAF | T990C | 12S rRNA | + | − | Reported |
| MT-RNR1 | DEAF | T1005C | 12S rRNA | + | − | Unclear |
| MT-RNR1 | DEAF-associated | A1027G | 12S rRNA | + | − | Reported |
| MT-RNR1 | SNHL | T1095C | 12S rRNA | + | + | Unclear |
| MT-RNR1 | DEAF | A1116G | 12S rRNA | + | − | Reported |
| MT-RNR1 | Possibly DEAF-associated | C1226G | 12S rRNA | + | − | Reported |
| MT-RNR1 | Possibly DEAF-associated | T1180G | 12S rRNA | + | − | Reported |
| MT-RNR1 | DEAF-associated | C1192A | 12S rRNA | + | − | Reported |
| MT-RNR1 | DEAF-associated | C1192T | 12S rRNA | + | − | Reported |
| MT-RNR1 | DEAF | T1291C | 12S rRNA | + | − | Unclear |
| MT-RNR1 | DEAF-associated | C1310T | 12S rRNA | + | − | Reported |
| MT-RNR1 | DEAF-associated | A1331G | 12S rRNA | + | − | Reported |
| MT-RNR1 | DEAF-associated | A1374G | 12S rRNA | + | − | Reported |
| MT-RNR1 | found in 1 HCM patient | T1391C | 12S rRNA | + | − | Reported |
| MT-RNR1 | SZ-associated | A1438A | 12S rRNA | + | − | Reported |
| MT-RNR1 | DEAF-associated | T1452C | 12S rRNA | + | − | Reported |
| MT-RNR1 | Possible DEAF risk factor | A1453G | 12S rRNA | . | . | Reported |
| MT-RNR1 | DEAF | A1491G = A1555G | 12S rRNA | . | . | See 1555G |
| MT-RNR1 | DEAF | C1494T | 12S rRNA | + | − | Cfrm |
| MT-RNR1 | DEAF | A1517C | 12S rRNA | − | + | Reported |
| MT-RNR1 | DEAF | C1537T | 12S rRNA | + | − | Reported |
| MT-RNR1 | DEAF | A1555G | 12S rRNA | + | − | Cfrm |

TABLE 2-continued

Known Mitochondrial DNA Base Substitution Causing Diseases: rNA/tRNA mutations

| Locus | Disease | Allele | RNA | Homo-plasmy | Hetero-Plasmy | Status |
|---|---|---|---|---|---|---|
| MT-RNR1 | found in 1 HCM patient | C1556T | 12S rRNA | + | − | Reported |
| MT-TV | AMDF | G1606A | tRNA Val | − | + | Cfrm |
| MT-TV | Leigh Syndrome | C1624T | tRNA Val | + | − | Reported |
| MT-TV | MNGIE-like disease/MELAS | A1630G | tRNA Val | − | + | Reported |
| MT-TV | MELAS | G1642A | tRNA Val | − | + | Reported |
| MT-TV | Adult Leigh Syndrome | G1644T | tRNA Val | − | + | Reported |
| MT-TV | HCM + MELAS | G1644A | tRNA Val | − | + | Reported |
| MT-TV | Movement Disorder | T1659C | tRNA Val | − | + | Reported |
| MT-RNR2 | Possibly LVNC-associated | T2352C | 16S rRNA | + | − | Reported |
| MT-RNR2 | Possibly LVNC-associated | G2361A | 16S rRNA | + | − | Reported |
| MT-RNR2 | Possibly LVNC-associated | A2755G | 16S rRNA | + | − | Reported |
| MT-RNR2 | Rett Syndrome | C2835T | 16S rRNA | − | + | Reported |
| MT-RNR2 | Cyclic Vomiting Syndrome with Migraine | G3010A | 16S rRNA | + | − | Reported |
| MT-RNR2 | Myopathy | G3090A | 16S rRNA | − | + | Reported |
| MT-RNR2 | MELAS | C3093G | 16S rRNA | − | + | Reported |
| MT-RNR2 | ADPD | G3196A | 16S rRNA | + | + | Reported |
| MT-TL1 | Sporadic bilateral optic neuropathy | A3236G | tRNA Leu (UUR) | . | . | Reported |
| MT-TL1 | MM | G3242A | tRNA Leu (UUR) | + | − | Reported |
| MT-TL1 | MELAS/LS | A3243G | tRNA Leu (UUR) | − | + | Cfrm |
| MT-TL1 | DMDF/MIDD/SNHL/FSGS/Cardiac + multi-organ dysfunction | A3243G | tRNA Leu (UUR) | − | + | Cfrm |
| MT-TL1 | CPEO/MM | A3243G | tRNA Leu (UUR) | − | + | Cfrm |
| MT-TL1 | MM/MELAS/SNHL/CPEO | A3243T | tRNA Leu (UUR) | − | + | Reported |
| MT-TL1 | MELAS | G3244A | tRNA Leu (UUR) | − | + | Reported |
| MT-TL1 | KSS | G3249A | tRNA Leu(UUR) | − | + | Reported |
| MT-TL1 | MM/CPEO | T3250C | tRNA Leu (UUR) | − | + | Reported |
| MT-TL1 | MM | A3251G | tRNA Leu (UUR) | − | + | Reported |
| MT-TL1 | MELAS | A3252G | tRNA Leu (UUR) | − | + | Reported |
| MT-TL1 | Gestational Diabetes (GDM) | C3254A | tRNA Leu (UUR) | − | + | Warrants further study |
| MT-TL1 | MM | C3254G | tRNA Leu (UUR) | − | + | Reported |
| MT-TL1 | CPEO/poss. hypertension factor | C3254T | tRNA Leu (UUR) | + | − | Reported |
| MT-TL1 | MERRF/KSS overlap | G3255A | tRNA Leu (UUR) | − | + | Reported |
| MT-TL1 | MELAS | C3256T | tRNA Leu (UUR) | − | + | Cfrm |
| MT-TL1 | MELAS/Myopathy | T3258C | tRNA Leu (UUR) | − | + | Reported |
| MT-TL1 | MMC | A3260G | tRNA Leu (UUR) | − | + | Cfrm |
| MT-TL1 | DM | T3264C | tRNA Leu (UUR) | − | + | Reported |
| MT-TL1 | MELAS | T3271C | tRNA Leu (UUR) | − | + | Cfrm |
| MT-TL1 | DM | T3271C | tRNA Leu (UUR) | − | + | Reported |
| MT-TL1 | PEM | T3271delT | tRNA Leu (UUR) | − | + | Reported |
| MT-TL1 | Ocular myopathy | T3273C | tRNA Leu (UUR) | − | + | Reported |
| MT-TL1 | Neuropsychiatric syndrome + cataract | A3274G | tRNA Leu (UUR) | − | + | Reported |
| MT-TL1 | LHON | C3275A | tRNA Leu (UUR) | + | − | Reported |
| MT-TL1 | Poss. hypertension factor | G3277A | tRNA Leu (UUR) | + | − | Reported |
| MT-TL1 | Poss. hypertension factor | T3278C | tRNA Leu (UUR) | + | − | Reported |
| MT-TL1 | Myopathy | A3280G | tRNA Leu (UUR) | − | + | Reported |
| MT-TL1 | Encephalomyopathy | C3287A | tRNA Leu (UUR) | − | + | Reported |

TABLE 2-continued

Known Mitochondrial DNA Base Substitution Causing Diseases: rNA/tRNA mutations

| Locus | Disease | Allele | RNA | Homo-plasmy | Hetero-Plasmy | Status |
|---|---|---|---|---|---|---|
| MT-TL1 | Myopathy | A3288G | tRNA Leu (UUR) | − | + | Reported |
| MT-TL1 | Poss. hypertension factor | T3290C | tRNA Leu (UUR) | + | − | Reported |
| MT-TL1 | MELAS/Myopathy/Deafness + Cognitive Impairment | T3291C | tRNA Leu (UUR) | − | + | Cfrm |
| MT-TL1 | MM | A3302G | tRNA Leu (UUR) | − | + | Cfrm |
| MT-TL1 | MMC | C3303T | tRNA Leu (UUR) | + | + | Cfrm |
| MT-TI | Maternally inherited essential hypertension | A4263G | tRNA Ile | + | − | Reported |
| MT-TI | MM/CPEO | A4267G | tRNA Ile | − | + | Reported |
| MT-TI | FICP | A4269G | tRNA Ile | − | + | Reported |
| MT-TI | CPEO/Motor Neuron Disease | T4274C | tRNA Ile | − | + | Reported |
| MT-TI | Poss. hypertension factor | T4277C | tRNA Ile | + | − | Reported |
| MT-TI | Recurrent Myoglobinuria | A4281G | tRNA Ile | − | + | Reported |
| MT-TI | Varied familial presentation/spastic paraparesis | G4284A | tRNA Ile | − | + | Reported |
| MT-TI | CPEO | T4285C | tRNA Ile | − | + | Reported |
| MT-TI | Progressive Encephalopathy/PEO, myopathy | T4290C | tRNA Ile | + | + | Reported |
| MT-TI | Hypomagnesemic Metabolic Syndrome | T4291C | tRNA Ile | + | − | Reported |
| MT-TI | MHCM/Maternally inherited hypertension | A4295G | tRNA Ile | + | + | Reported |
| MT-TI | CPEO/MS | G4298A | tRNA Ile | − | + | Cfrm |
| MT-TI | MICM | A4300G | tRNA Ile | + | + | Cfrm |
| MT-TI | CPEO | A4302G | tRNA Ile | − | + | Reported |
| MT-TI | CPEO | G4308A | tRNA Ile | − | + | Reported |
| MT-TI | CPEO | G4309A | tRNA Ile | − | + | Reported |
| MT-TI | Poss. hypertension factor | T4314C | tRNA Ile | + | − | Reported |
| MT-TI | HCM with hearing loss/poss. hypertension factor | A4316G | tRNA Ile | + | + | Reported |
| MT-TI | FICP/poss. hypertension factor | A4317G | tRNA Ile | + | − | Reported |
| MT-TI | Mitochondrial Encephalocardiomyopathy | C4320T | tRNA Ile | − | + | Reported |
| MT-TQ | Encephalopathy/MELAS | G4332A | tRNA Gln | − | + | Cfrm |
| MT-TQ | ADPD/Hearing Loss & Migraine | T4336C | tRNA Gln | + | + | Unclear |
| MT-TQ | Poss. hypertension factor | A4343G | tRNA Gln | + | − | Reported |
| MT-TQ | Poss. hypertension factor | C4345T | tRNA Gln | + | − | Reported |
| MT-TQ | Poss. hypertension factor | T4353C | tRNA Gln | + | − | Reported |
| MT-TQ | Possibly associated w DEAF + RP + dev delay/hypertension | T4363C | tRNA Gln | + | − | Reported |
| MT-TQ | Myopathy | T4370AT | tRNA Gln | − | + | Reported |
| MT-TQ | Possibly LVNC-associated | T4373C | tRNA Gln | + | − | Reported |
| MT-TQ | LHON | A4381G | tRNA Gln | + | − | Reported |
| MT-TQ | Poss. hypertension factor | C4387A | tRNA Gln | + | − | Reported |
| MT-TQ | Poss. hypertension factor | A4388G | tRNA Gln | + | − | Reported |
| MT-TQ | Poss. hypertension factor | C4392T | tRNA Gln | + | − | Reported |
| MT-TQ | Poss. hypertension factor | A4395G | tRNA Gln | + | − | Reported |
| MT-NC2 | Hypertension | A4401G | NC2 Gln-Met spacer | + | − | Reported |
| MT-TM | MM | T4409C | tRNA Met | − | + | Reported |
| MT-TM | Poss. hypertension factor | C4410A | tRNA Met | + | − | Reported |
| MT-TM | EXIT & APS2 | A4415G | tRNA Met | − | + | Reported |
| MT-TM | LHON modulator/poss. hypertension factor | A4435G | tRNA Met | + | − | Reported |
| MT-TM | Myopathy | G4450A | tRNA Met | − | + | Reported |
| MT-TM | Possible contributor to mito dysfunction/hypertension | T4454C | tRNA Met | + | − | Reported |
| MT-TM | Poss. hypertension factor | C4456T | tRNA Met | − | + | Reported |
| MT-TW | MM | G5521A | tRNA Trp | − | + | Reported |
| MT-TW | Leigh Syndrome | T5523G | tRNA Trp | − | + | Reported |
| MT-TW | Gastrointestinal Syndrome | G5532A | tRNA Trp | − | + | Reported |
| MT-TW | Leigh Syndrome | A5537insT | tRNA Trp | − | + | Cfrm |
| MT-TW | Encephalomyopathy/DEAF | G5540A | tRNA Trp | − | + | Reported |
| MT-TW | MM | T5543C | tRNA Trp | − | + | Reported |
| MT-TW | HCM severe multisystem disorder | C5545T | tRNA Trp | − | + | Reported |
| MT-TW | DEMCHO | G5549A | tRNA Trp | − | + | Reported |
| MT-TW | Leigh Syndrome | A5559G | tRNA Trp | − | + | Reported |
| MT-TW | Myopathy | T5567C | tRNA Trp | − | + | Reported |
| MT-TW | DEAF | A5568G | tRNA Trp | + | − | Reported |
| MT-TA | Possible DEAF modifier | T5587C | tRNA Ala | + | − | Reported |
| MT-TA | Myopathy | G5591A | tRNA Ala | − | + | Reported |
| MT-TA | CPEO/DEAF enhancer | T5628C | tRNA Ala | − | + | Reported |
| MT-TA | PEO | T5636C | tRNA Ala | − | + | Reported |
| MT-TA | Myopathy | G5650A | tRNA Ala | − | + | Reported |
| MT-TA | DEAF enhancer | T5655C | tRNA Ala | + | − | Reported |
| MT-TN | CPEO/MM | T5692C | tRNA Asn | − | + | Reported |
| MT-TN | Encephalomyopathy | T5693C | tRNA Asn | + | − | Reported |
| MT-TN | CPEO/MM | G5698A | tRNA Asn | − | + | Reported |
| MT-TN | CPEO/MM | G5703A | tRNA Asn | − | + | Cfrm |

TABLE 2-continued

Known Mitochondrial DNA Base Substitution Causing Diseases: rNA/tRNA mutations

| Locus | Disease | Allele | RNA | Homo-plasmy | Hetero-Plasmy | Status |
|---|---|---|---|---|---|---|
| MT-TN | Multiorgan failure | T5728C | tRNA Asn | − | + | Reported |
| MT-TC | SNHL | G5780A | tRNA Cys | − | + | Reported |
| MT-TC | Myopathy deafness | G5783A | tRNA Cys | − | + | Reported |
| MT-TC | DEAF1555 increased penetrance | T5802C | tRNA Cys | + | − | Reported |
| MT-TC | Mitochondrial Encephalopathy | T5814C | tRNA Cys | − | + | L2b marker |
| MT-TC | Progressive Dystonia | A5816G | tRNA Cys | + | − | Reported |
| MT-TC | DEAF helper mut. | G5821A | tRNA Cys | + | − | Reported |
| MT-TY | FSGS/Mitochondrial Cytopathy | A5843G | tRNA Tyr | + | − | Reported |
| MT-TY | EXIT | T5874G | tRNA Tyr | − | + | Reported |
| MT-TS1 precursor? | DEAF | A7445C | tRNA Ser (UCN) precursor | + | − | Reported |
| MT-TS1 precursor? | SNHL | A7445G | tRNA Ser (UCN) precursor | + | + | Cfrm |
| MT-TS1 precursor? | SNHL | A7445T | tRNA Ser (UCN) precursor | + | − | Reported |
| MT-TS1 | DEAF | A7456G | tRNA Ser (UCN) | + | − | Unclear |
| MT-TS1 | PEO | G7458A | tRNA Ser (UCN) | − | + | Reported |
| MT-TS1 | DEAF | C7462T | tRNA Ser (UCN) | + | − | Reported |
| MT-TS1 | PEM/AMDF/Motor neuron disease-like | C7471CC (='7472insC') | tRNA Ser (UCN) | + | + | Cfrm |
| MT-TS1 | MM/DMDF modulator | A7472C | tRNA Ser (UCN) | + | − | Reported |
| MT-TS1 | MM | T7480G | tRNA Ser (UCN) | − | + | Reported |
| MT-TS1 | MM/EXIT | G7497A | tRNA Ser (UCN) | + | + | Cfrm |
| MT-TS1 | Maternally inherited hearing loss | T7505C | tRNA Ser (UCN) | + | − | Reported |
| MT-TS1 | PEO with hearing loss | G7506A | tRNA Ser (UCN) | − | + | Reported |
| MT-TS1 | SNHL | T7510C | tRNA Ser (UCN) | − | + | Reported |
| MT-TS1 | SNHL | T7511C | tRNA Ser (UCN) | + | + | Cfrm |
| MT-TS1 | PEM/MERME | T7512C | tRNA Ser (UCN) | + | + | Reported |
| MT-TD | Sporadic bilateral optic neuropathy | G7520A | tRNA Asp | . | . | Reported |
| MT-TD | Mitochondrial Myopathy | A7526G | tRNA Asp | − | + | Reported |
| MT-TD | MEPR | A7543G | tRNA Asp | − | + | Reported |
| MT-TK | DMDF/MERRF/HCM/epilepsy | A8296G | tRNA Lys | + | + | Reported |
| MT-TK | Encephalopathy | A8302T | tRNA Lys | + | − | Unclear |
| MT-TK | Poss. hypertension factor | T8311C | tRNA Lys | + | − | Reported |
| MT-TK | MNGIE/Progressive mito cytopathy | G8313A | tRNA Lys | − | + | Reported |
| MT-TK | MELAS | T8316C | tRNA Lys | − | + | Reported |
| MT-TK | Mitochondrial Cytopathy | A8326G | tRNA Lys | − | + | Reported |
| MT-TK | Mito Encephalopathy/EXIT with myopathy and ptosis | G8328A | tRNA Lys | − | + | Reported |
| MT-TK | Dystonia and stroke-like episodes | A8332G | tRNA Lys | + | − | Reported |
| MT-TK | Poss. hypertension factor | T8337C | tRNA Lys | + | − | Reported |
| MT-TK | Exercise Intolerance | G8340A | tRNA Lys | . | . | Reported |
| MT-TK | PEO and Myoclonus | G8342A | tRNA Lys | − | + | Reported |
| MT-TK | Possible PD risk factor | A8343G | tRNA Lys | + | − | Reported |
| MT-TK | MERRF | A8344G | tRNA Lys | − | + | Cfrm |
| MT-TK | Other-Depressive mood disorder/leukoencephalopathy/HiCM/LD | A8344G | tRNA Lys | − | + | Reported |
| MT-TK | Poss. hypertension factor | A8347G | tRNA Lys | + | − | Reported |
| MT-TK | Cardiomyopathy/SNHL/poss. hypertension factor | A8348G | tRNA Lys | + | + | Reported |
| MT-TK | Myopathy | T8355C | tRNA Lys | − | + | Reported |
| MT-TK | MERRF | T8356C | tRNA Lys | − | + | Cfrm |
| MT-TK | MERRF | G8361A | tRNA Lys | − | + | Reported |
| MT-TK | Myopathy | T8362G | tRNA Lys | − | + | Reported |
| MT-TK | MICM + DEAF/MERRF/Autism/LS/Ataxia + Lipomas | G8363A | tRNA Lys | − | + | Cfrm |
| MT-TG | MHCM | T9997C | tRNA Gly | nd | + | Reported |
| MT-TG | CIPO/Encephalopathy | A10006G | tRNA Gly | + | − | Unclear |
| MT-TG | PEM | T10010C | tRNA Gly | − | + | Cfrm |
| MT-TG | Myopathy | G10014A | tRNA Gly | + | − | Unclear |
| MT-TG | SIDS | A10044G | tRNA Gly | − | + | Unclear |

TABLE 2-continued

Known Mitochondrial DNA Base Substitution Causing Diseases: rNA/tRNA mutations

| Locus | Disease | Allele | RNA | Homo-plasmy | Hetero-Plasmy | Status |
|---|---|---|---|---|---|---|
| MT-TR | Mitochondrial Myopathy | G10406A | tRNA Arg | − | + | Reported |
| MT-TR | Progressive Encephalopathy | A10438G | tRNA Arg | − | + | Reported |
| MT-TR | DEAF helper mut. | T10454C | tRNA Arg | + | − | Reported |
| MT-TH | MERRF-MELAS/Cerebral edema | G12147A | tRNA His | − | + | Cfrm |
| MT-TH | RP + DEAF | G12183A | tRNA His | − | + | Reported |
| MT-TH | MICM | G12192A | tRNA His | + | − | Reported |
| MT-TS2 | Myopathy/Encephalopathy | G12207A | tRNA Ser (AGY) | − | + | Reported |
| MT-TS2 | DEAF helper mut. | C12224T | tRNA Ser (AGY) | + | − | Reported |
| MT-TS2 | DEAF | G12236A | tRNA Ser (AGY) | + | − | Reported |
| MT-TS2 | CIPO | C12246A | tRNA Ser (AGY) | nd | nd | Reported |
| MT-TS2 | DMDF/RP + SNHL | C12258A | tRNA Ser (AGY) | − | + | Reported |
| MT-TS2 | CPEO | G12276A | tRNA Ser (AGY) | − | + | Reported |
| MT-TS2 | CPEO | G12283A | tRNA Ser (AGY) | − | + | Reported |
| MT-TL2 | CPEO | G12294A | tRNA Leu (CUN) | − | + | Reported |
| MT-TL2 | Dilated Cardiomyopathy/LS | T12297C | tRNA Leu (CUN) | + | + | Reported |
| MT-TL2 | MELAS | A12299C | tRNA Leu (CUN) | − | + | Reported |
| MT-TL2 | 3243 suppressor mutant | G12300A | tRNA Leu (CUN) | − | + | Reported |
| MT-TL2 | CPEO/Stroke/CM/Breast & Renal & Prostate Cancer Risk/Altered brain pH | A12308G | tRNA Leu (CUN) | + | + | Haplogroup U marker |
| MT-TL2 | CPEO | T12311C | tRNA Leu (CUN) | + | + | Reported |
| MT-TL2 | FSHD | T12313C | tRNA Leu (CUN) | − | + | Reported |
| MT-TL2 | CPEO/KSS | G12315A | tRNA Leu (CUN) | − | + | Cfrm |
| MT-TL2 | CPEO | G12316A | tRNA Leu (CUN) | − | + | Reported |
| MT-TL2 | MM | A12320G | tRNA Leu (CUN) | − | + | Reported |
| MT-TE | Reversible COX deficiency myopathy | T14674C | tRNA Glu | + | − | Cfrm |
| MT-TE | Reversible COX deficiency myopathy | T14674G | tRNA Glu | + | − | Reported |
| MT-TE | Mitochondrial encephalomyopathy | C14680A | tRNA Glu | − | + | Reported |
| MT-TE | Mito myopathy w respiratory failure | A14687G | tRNA Glu | + | − | Reported |
| MT-TE | LHON helper mut. | A14692G | tRNA Glu | + | − | Reported |
| MT-TE | MELAS/LHON/DEAF/hypertension helper | A14693G | tRNA Glu | + | + | Reported |
| MT-TE | Progressive Encephalopathy | A14696G | tRNA Glu | − | + | Reported |
| MT-TE | MM + DMDF/Encephalomyopathy | T14709C | tRNA Glu | + | + | Cfrm |
| MT-TE | Encephalomyopathy + Retinopathy | G14740A | tRNA Glu | − | + | Reported |
| MT-TE | CPEO + Myopathy | T14723C | tRNA Glu | − | + | Reported |
| MT-TE | Mito Leukoencephalopathy | G14724A | tRNA Glu | − | + | Reported |
| MT-TE | EXIT | G14739A | tRNA Glu | − | + | Reported |
| MT-TT | DEAF helper mut. | T15908C | tRNA Thr | + | − | Reported |
| MT-TT | Encephalomyopathy | G15915A | tRNA Thr | − | + | Reported |
| MT-TT | LIMM | A15923G | tRNA Thr | nd | − | Reported |
| MT-TT | LIMM | A15924G | tRNA Thr | nd | − | P.M. |
| MT-TT | Multiple Sclerosis/DEAF1555 increased penetrance | G15927A | tRNA Thr | + | − | P.M./possible helper mutation |
| MT-TT | Multiple Sclerosis | G15928A | tRNA Thr | + | − | P.M. |
| MT-TT | MM | T15940delT | tRNA Thr | + | − | P.M. |
| MT-TT | Possibly LVNC-associated | T15942C | tRNA Thr | + | − | Reported |
| MT-TT | Dopaminergic nerve cell death (PD) | G15950A | tRNA Thr | + | − | Reported |
| MT-TT | LHON modulator | A15951G | tRNA Thr | + | − | Reported |
| MT-TP | Dopaminergic nerve cell death (PD) | A15965G | tRNA Pro | + | − | Reported |
| MT-TP | MERRF-like disease | G15967A | tRNA Pro | − | + | Reported |
| MT-TP | Ataxia + RP + deafness | C15975T | tRNA Pro | − | + | Reported |
| MT-TP | MM | C15990T | tRNA Pro | − | + | Reported |
| MT-TP | Mitochondrial cytopathy | G15995A | tRNA Pro | − | + | Reported |
| MT-TP | Mitochondrial cytopathy | T16002C | tRNA Pro | − | + | Reported |

Notes:
LHON Leber Hereditary Optic Neuropathy
AD Alzheimer's Disease
ADPD Alzheimer's Disease and Parkinsons's Disease
NARP Neurogenic muscle weakness, Ataxia, and Retinitis Pigmentosa; alternate phenotype at this locus is reported as Leigh Disease TABLE 2-continued Known Mitochondrial DNA Base Substitution Causing Diseases: rNA/tRNA mutations

| Locus | Disease | Allele | RNA | Homo-plasmy | Hetero-Plasmy | Status |
|---|---|---|---|---|---|---|

MELAS Mitochondrial Encephalomyopathy, Lactic Acidosis, and Stroke-like episodes
MERRF Myoclonic Epilepsy and Ragged Red Muscle Fibers
CPEO Chronic Progressive External Ophthalmoplegia
DM Diabetes Mellitus
CIPO Chronic Intestinal Pseudoobstruction with myopathy and Ophthalmoplegia
PEM Progressive encephalopathy
MM Mitochondrial Myopathy
LIMM Lethal Infantile Mitochondrial Myopathy
MMC Maternal Myopathy and Cardiomyopathy
FICP Fatal Infantile Cardiomyopathy Plus, a MELAS-associated cardiomyopathy
LDYT Leber's hereditary optic neuropathy and DYsTonia
MHCM Maternally inherited Hypertrophic CardioMyopathy
KSS Kearns Sayre Syndrome
DMDF Diabetes Mellitus + DeaFness
DEAF Maternally inherited DEAFness or aminoglycoside-induced DEAFness
SNHL SensoriNeural Hearing Loss
Homoplasmy = pure mutant mtDNAs.
Heteroplasmy = mixture of mutant and normal mtDNAs.
nd = not determined.
"Reported" status indicates that one or more publications have considered the mutation as possibly pathologic. This is not an assignment of pathogenicity by MITOMAP but is a report of literature. Previously, mutations with this status were termed "Prov" (provisional).
"Cfrm"(confirmed) status indicates that at least two or more independent laboratories have published reports on the pathogenicity of a specific mutation. These mutations are generally accepted by the mitochondrial research community as being pathogenic. A status of "Cfrm" is not an assignment of pathogenicity by MITOMAP but is a report of published literature. Researchers and clinicians are cautioned that additional data and/or analysis may still be necessary to confirm the pathological significance of some of these mutations.
"P.M." (point mutation/polymorphism) status indicates that some published reports have determined the mutation to be a non-pathogenic polymorphism.

The following examples are intended to illustrate but not to limit the invention.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method of manipulating the processing, targeting, and/or internalization of a nucleic acid molecule which comprises one or more of the following steps providing an altered tRNA aminoacyl stem that is directly or indirectly linked to the nucleic acid molecule to thereby enable the nucleic acid molecule to escape the nucleus of a cell; providing a mitochondria localization sequence that is directly or indirectly linked to the nucleic acid molecule to thereby cause the nucleic acid molecule to localize in the proximity of a mitochondrion; and providing an RNA import sequence that is directly or indirectly linked to the nucleic acid molecule to thereby cause the nucleic acid molecule to be internalized by a mitochondrion, and wherein the RNA import sequence is selected from the group consisting of SEQ ID NO:6, SEQ ID NO:7, SEQ ID NO:38, SEQ ID NO:39, sequences which are about 15-30 nucleotides long and comprise SEQ ID NO:39, and sequences complementary thereto.

2. The method of claim 1, wherein the nucleic acid molecule is a nucleus-encoded non-coding RNA.

3. The method of claim 1, wherein the nucleic acid molecule is a wild-type sequence of a gene a fragment thereof or its complement in the mitochondrial genome of a mammalian subject.

4. The method of claim 1, where the nucleic acid molecule is a RNA:DNA hybrid.

5. The method of claim 1,
wherein the sequences are capable of forming a single stem-loop.

6. The method of claim 1, wherein the mitochondrial localization sequence is mammalian.

7. The method of claim 1, wherein the mitochondrial localization sequence is SEQ ID NO:34 or its complement.

8. The method of claim 1, wherein the nucleic acid sequence is not natively associated with the mitochondria localization sequence or the RNA import sequence.

9. The method of claim 1, wherein the nucleic acid sequence is RNA or ssDNA.

10. The method of claim 1, wherein the nucleic acid molecule is a microRNA.

11. The method of claim 1, wherein the nucleic acid molecule is a riboenzyme.

* * * * *